US010781454B2

(12) United States Patent
Dawson et al.

(10) Patent No.: US 10,781,454 B2
(45) Date of Patent: *Sep. 22, 2020

(54) CITRUS TRISTEZA VIRUS BASED VECTORS FOR FOREIGN GENE/S EXPRESSION

(71) Applicant: University of Florida Research Foundation, Inc., Gainesville, FL (US)

(72) Inventors: William O. Dawson, Winter Haven, FL (US); Svetlana Folimonova, Gainesville, FL (US); Choaa Amine El Mohtar, Lake Alfred, FL (US); Siddarame Gowda, Lakeland, FL (US); Subhas Hajeri, Visalia, CA (US)

(73) Assignee: University of Florida Research Foundation, Incorporated, Gainsville, FL (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/974,315

(22) Filed: May 8, 2018

(65) Prior Publication Data

US 2018/0355325 A1    Dec. 13, 2018

Related U.S. Application Data

(63) Continuation of application No. 14/269,637, filed on May 5, 2014, now Pat. No. 10,017,747, which is a continuation-in-part of application No. 13/624,294, filed on Sep. 21, 2012, now Pat. No. 10,093,939.

(60) Provisional application No. 61/537,154, filed on Sep. 21, 2011, provisional application No. 61/970,975, filed on Mar. 27, 2014.

(51) Int. Cl.
*C12N 15/82* (2006.01)

(52) U.S. Cl.
CPC .................. *C12N 15/8203* (2013.01)

(58) Field of Classification Search
None
See application file for complete search history.

(56) References Cited

U.S. PATENT DOCUMENTS

| 10,017,747 B2* | 7/2018 | Dawson | C12N 15/8203 |
| 2010/0017911 A1* | 1/2010 | Dawson | C12N 15/8203 |
| | | | 800/279 |
| 2011/0119788 A1* | 5/2011 | Rodriguez Baixauli | ............. |
| | | | C12N 9/88 |
| | | | 800/279 |

OTHER PUBLICATIONS

Cowda et al (Infection of Citrus Plants with Virions Generated in *Nicotiana benthamiana* Plants Agroinfiltrated with a Binary Vector Based *Citrus tristeza virus*. Sixteenth IOCV Conference, p. 23-33, 2005). (Year: 2005).*

* cited by examiner

*Primary Examiner* — Medina A Ibrahim
*Assistant Examiner* — Wayne Zhong
(74) *Attorney, Agent, or Firm* — Timothy H. Van Dyke; Beusse, Wolter, Sanks & Maire PLLC

(57) ABSTRACT

Disclosed herein are viral vectors based on modifications of the Citrus Tristeza virus useful for transfecting citrus trees for beneficial purposes. Included in the disclosure are viral vectors including one or more gene cassettes that encode heterologous polypeptides. The gene cassettes are positioned at desirable locations on the viral genome so as to enable expression while preserving functionality of the virus. Also disclosed are methods of transfecting plants and plants transfected with viral vector embodiments.

8 Claims, 31 Drawing Sheets

Specification includes a Sequence Listing.

A- CTV9RΔp33
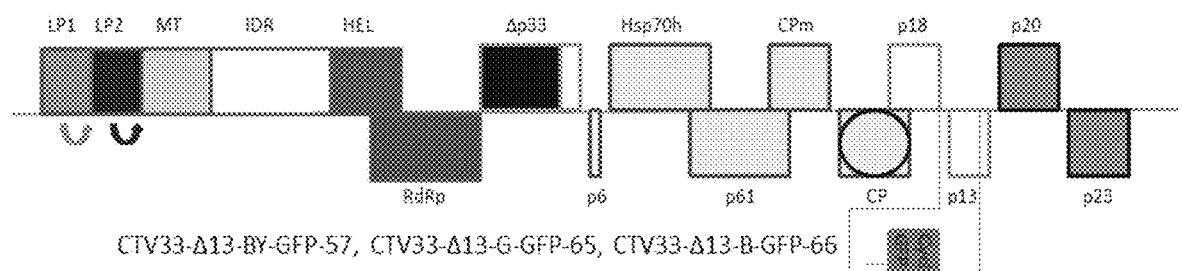
B- Northern Blot Hybridization
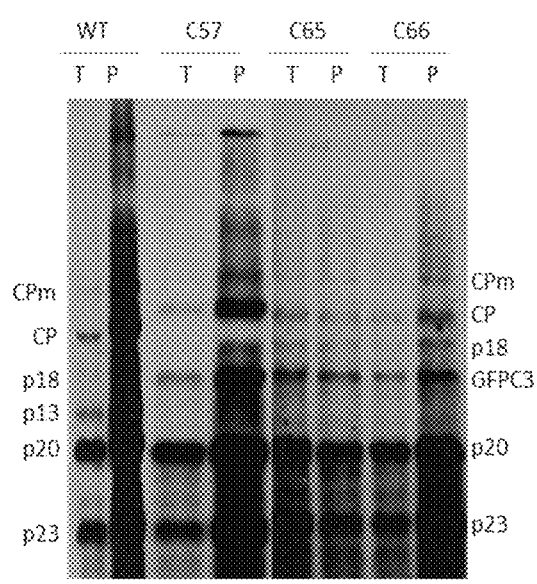
**C- *N. benthamiana***
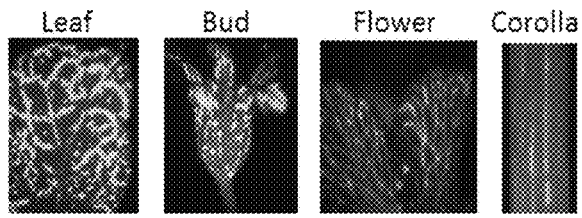
**D- *Citrus macrophylla***
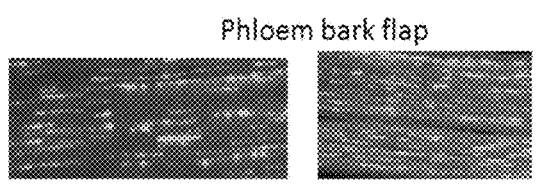
FIG. 1

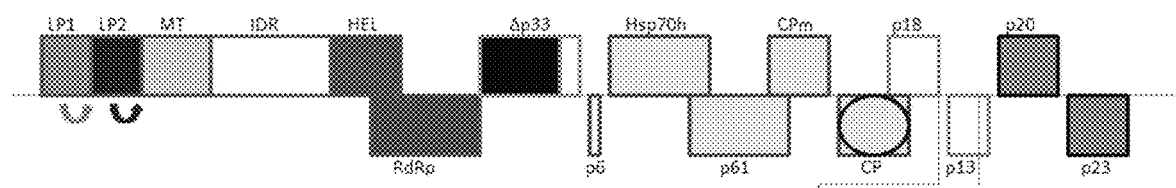
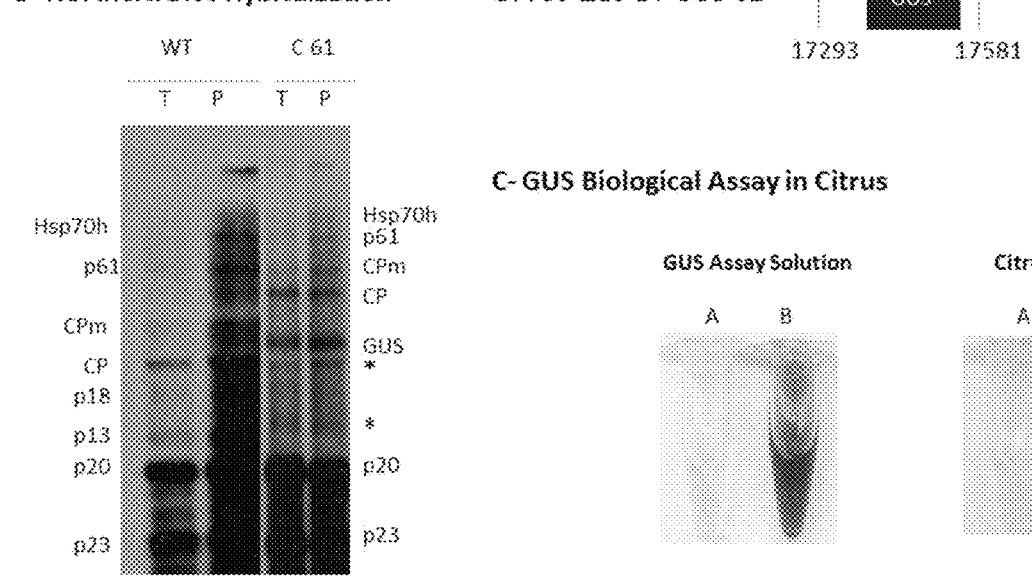
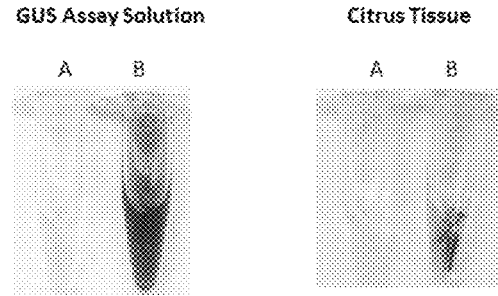
FIG. 2

A- CTV9RΔp33

B- Northern Blot Hybridization

C- N. benthamiana

Leaf    Bud    Flower    Corolla

D- Citrus macrophylla

Phloem bark flap

FIG. 3

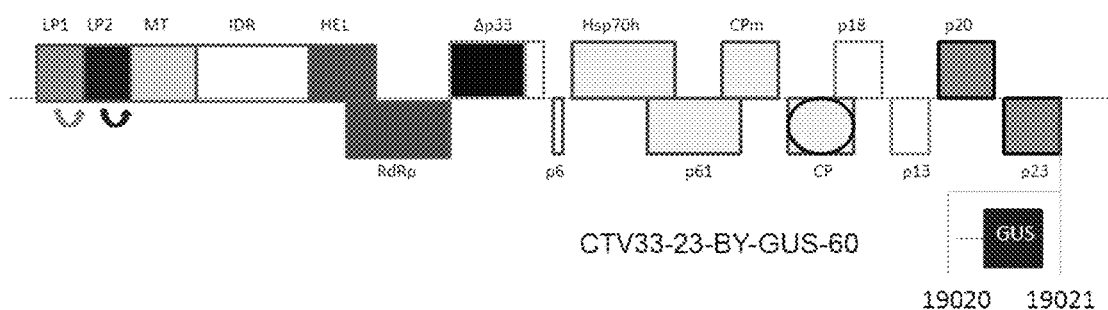
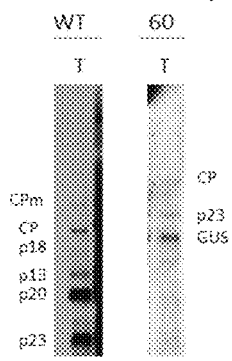
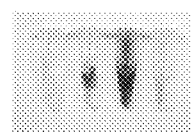
FIG. 6

Internal Ribosome Entry Site Strategy (IRES)
A-CTV9RΔp33
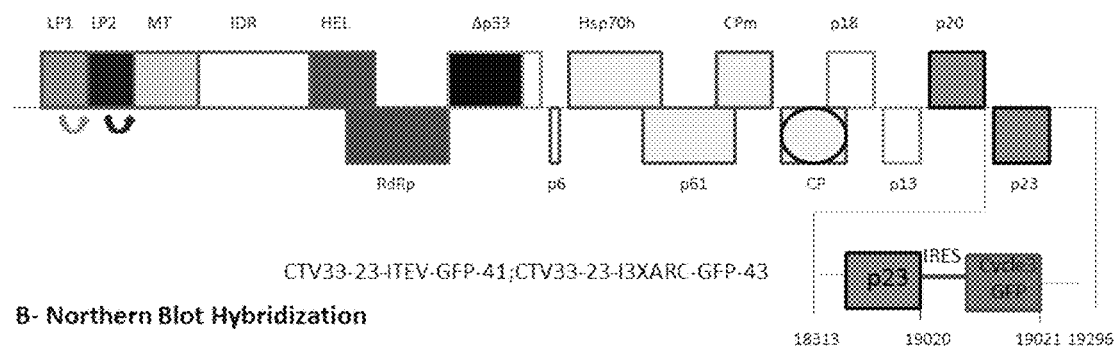
CTV33-23-ITEV-GFP-41;CTV33-23-I3XARC-GFP-43
B- Northern Blot Hybridization
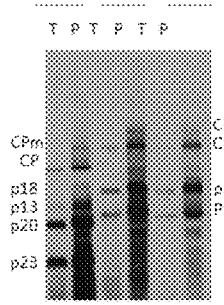
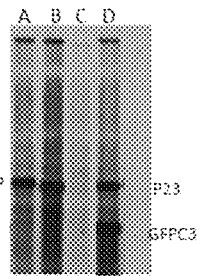
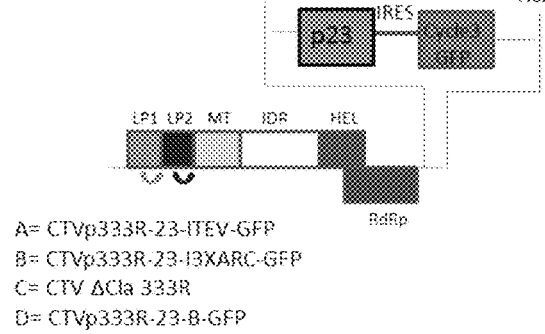
A= CTVp333R-23-ITEV-GFP
B= CTVp333R-23-I3XARC-GFP
C= CTV ΔCla 333R
D= CTVp333R-23-B-GFP
FIG. 7

Poly-Peptide Fusion

A- CTV9RΔp33

FIG. 8

Replacement of p13 gene

CTV33-Δ13-BYGFP-NI

A-  B-
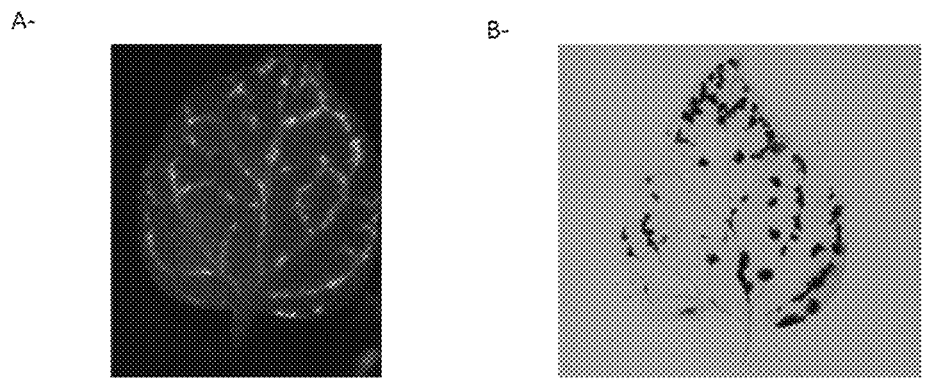
FIG. 12
Insertion between p23 and 3'NTR
A- CTV9RΔp33
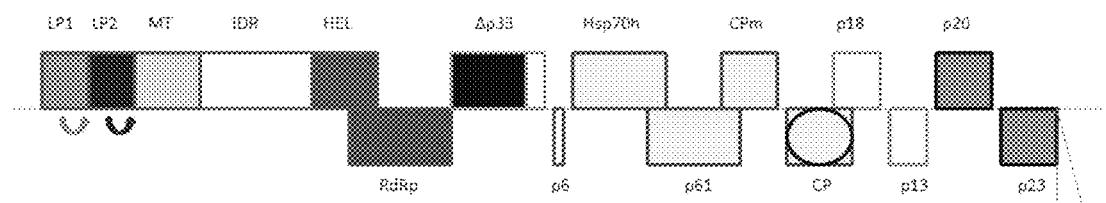
B- Northern Blot Hybrization
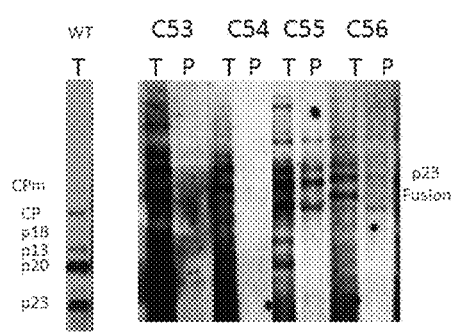
CTV33-23-BY-GFP-HC-GUS-51
CTV33-23-G-GFP-HC-GUS-53
CTV33-23-BY-GFP-HC-GUS-55
CTV33-23-BY-GFP-NIa-GUS-52
CTV33-23-G-GFP-NIa-GUS-54
CTV33-23-BY-GFP-NIa-GUS-56
FIG. 13

*Example 6: Expression of multiple foreign genes simultaneously from different locations*
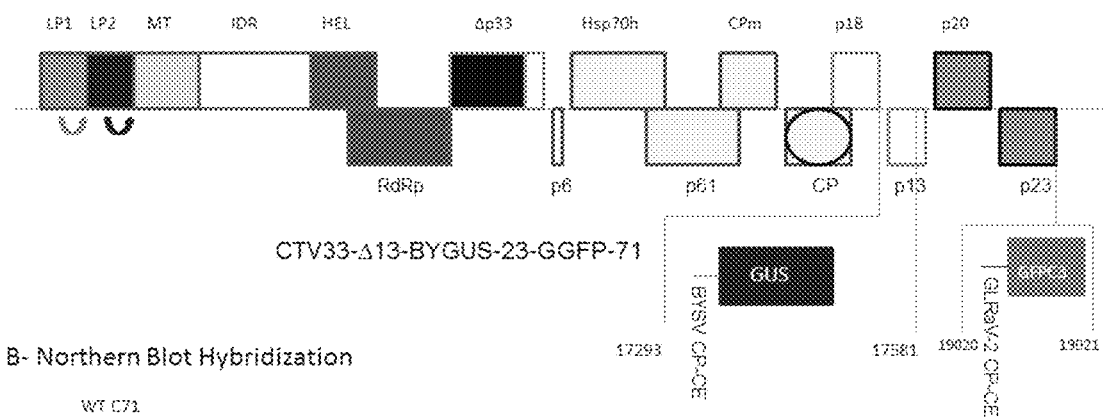
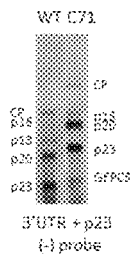
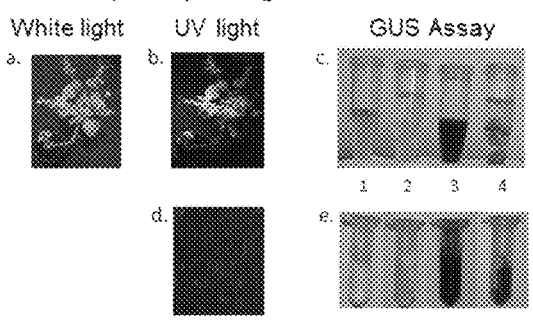
FIG. 18

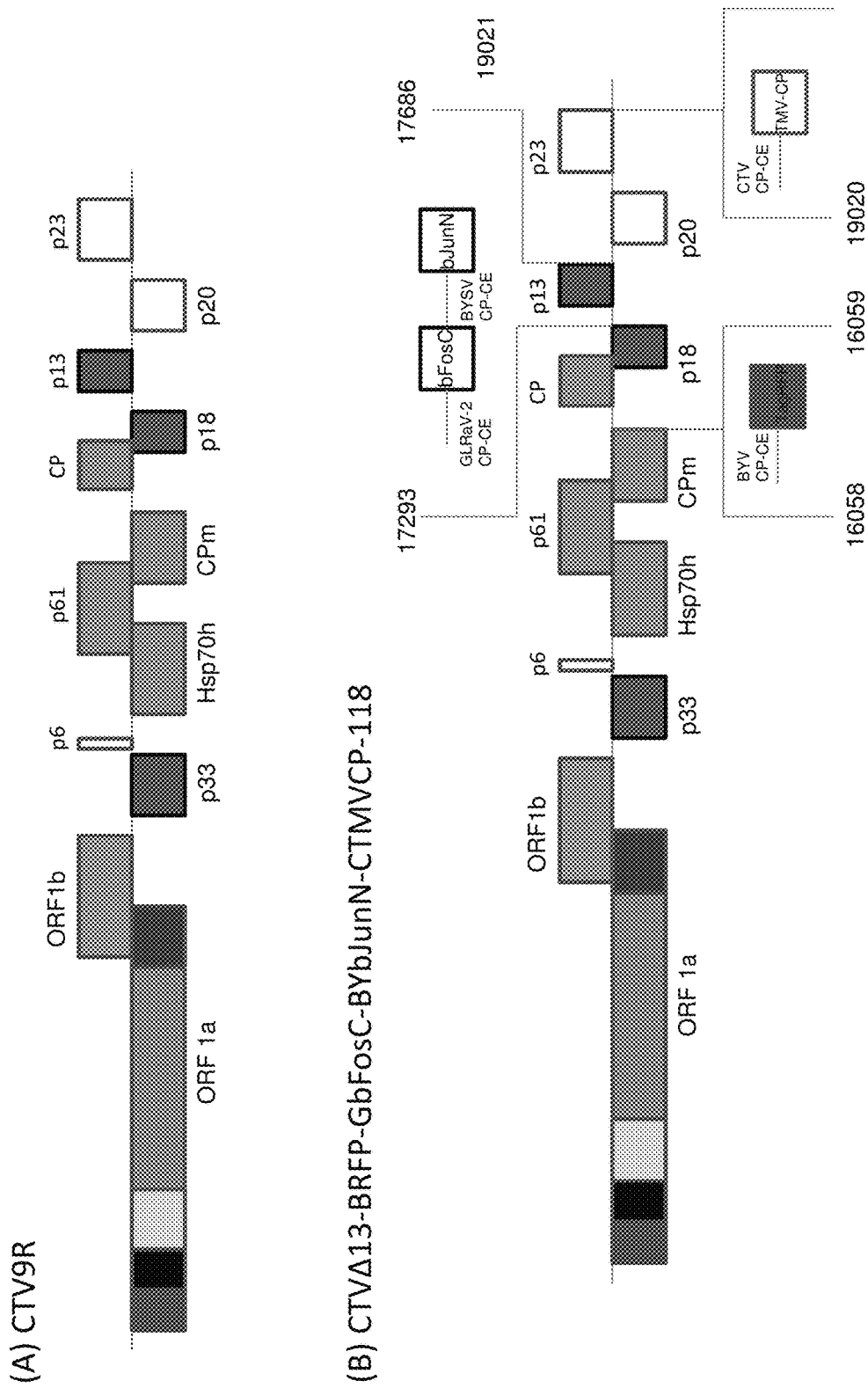

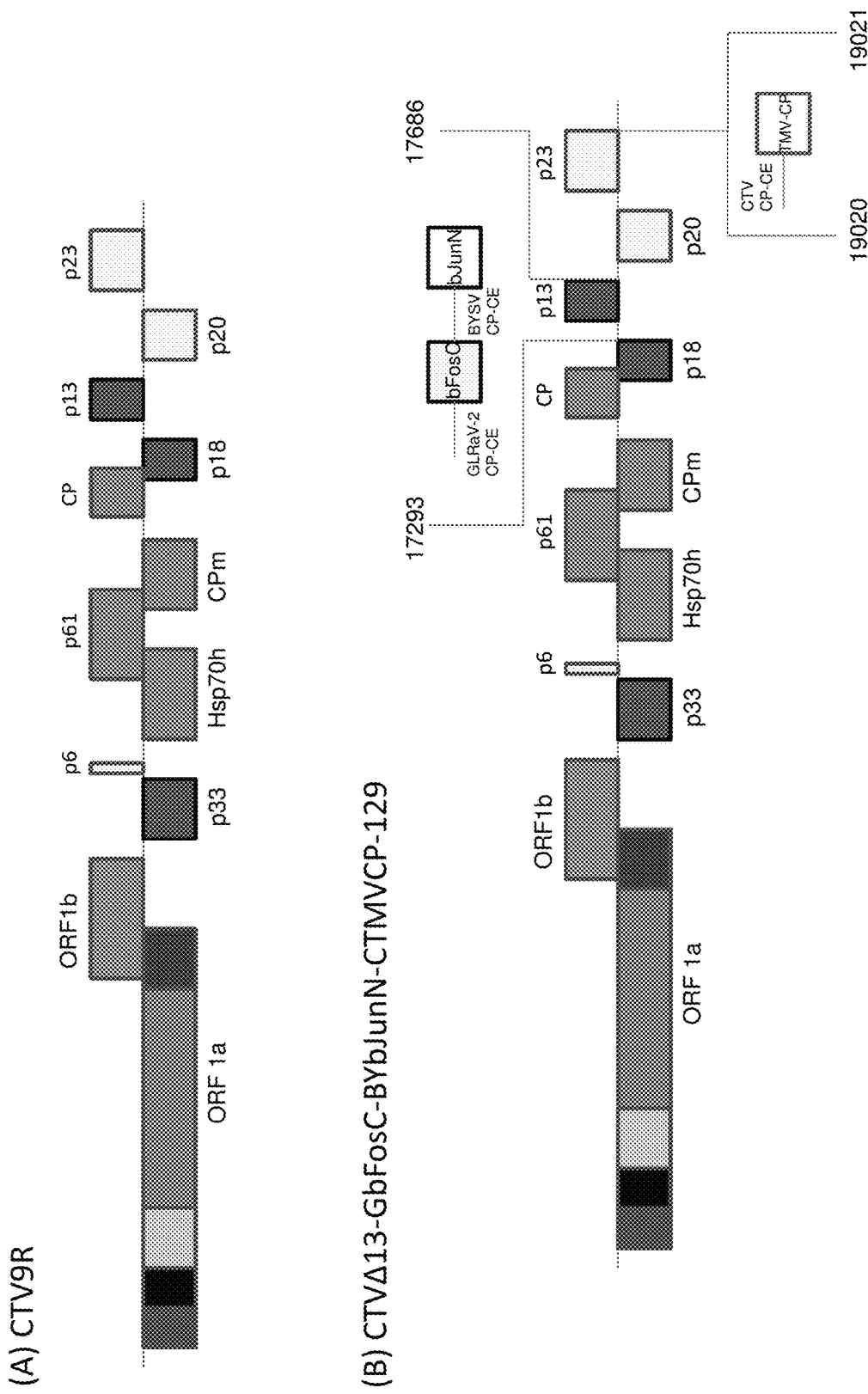
Fig. 21 3 gene vector

Fig. 22 3Gene vector (A) CTV9R (B) CTV-BRFP-BYGFP-CTMVCP-117

Infiltrated into N. benthamiana (partial systemic movement visualised via GFP)

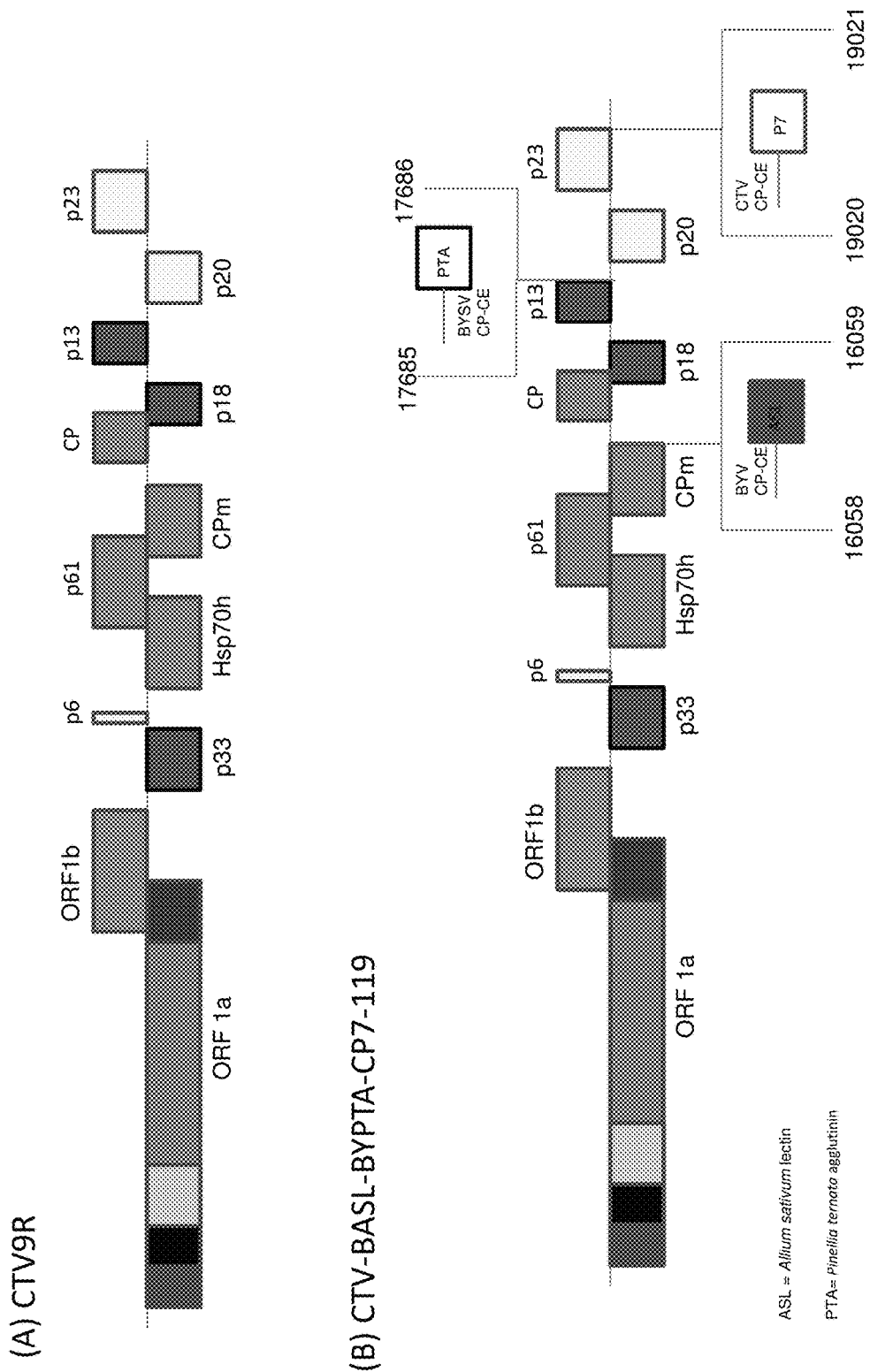

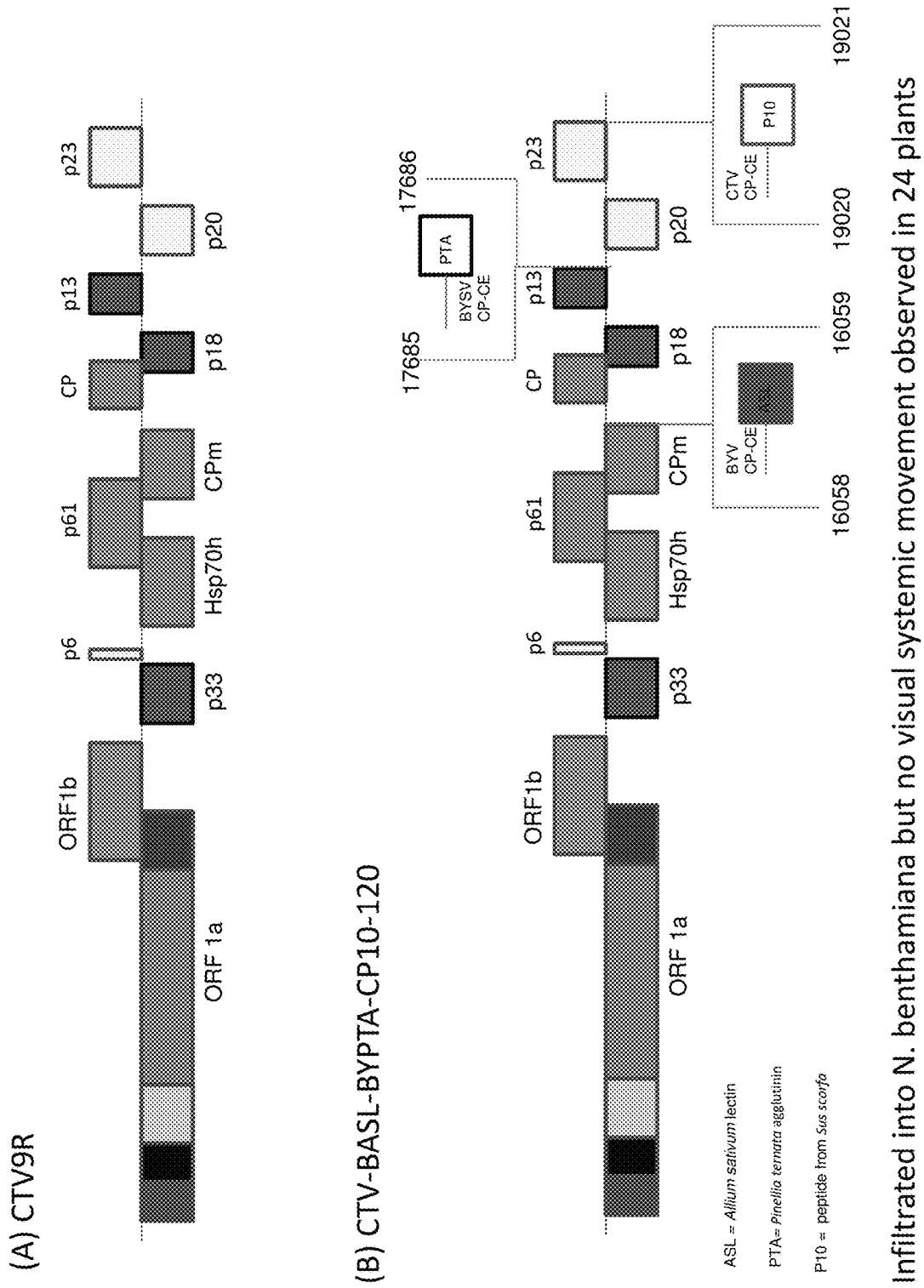
Fig. 24 3Gene vector

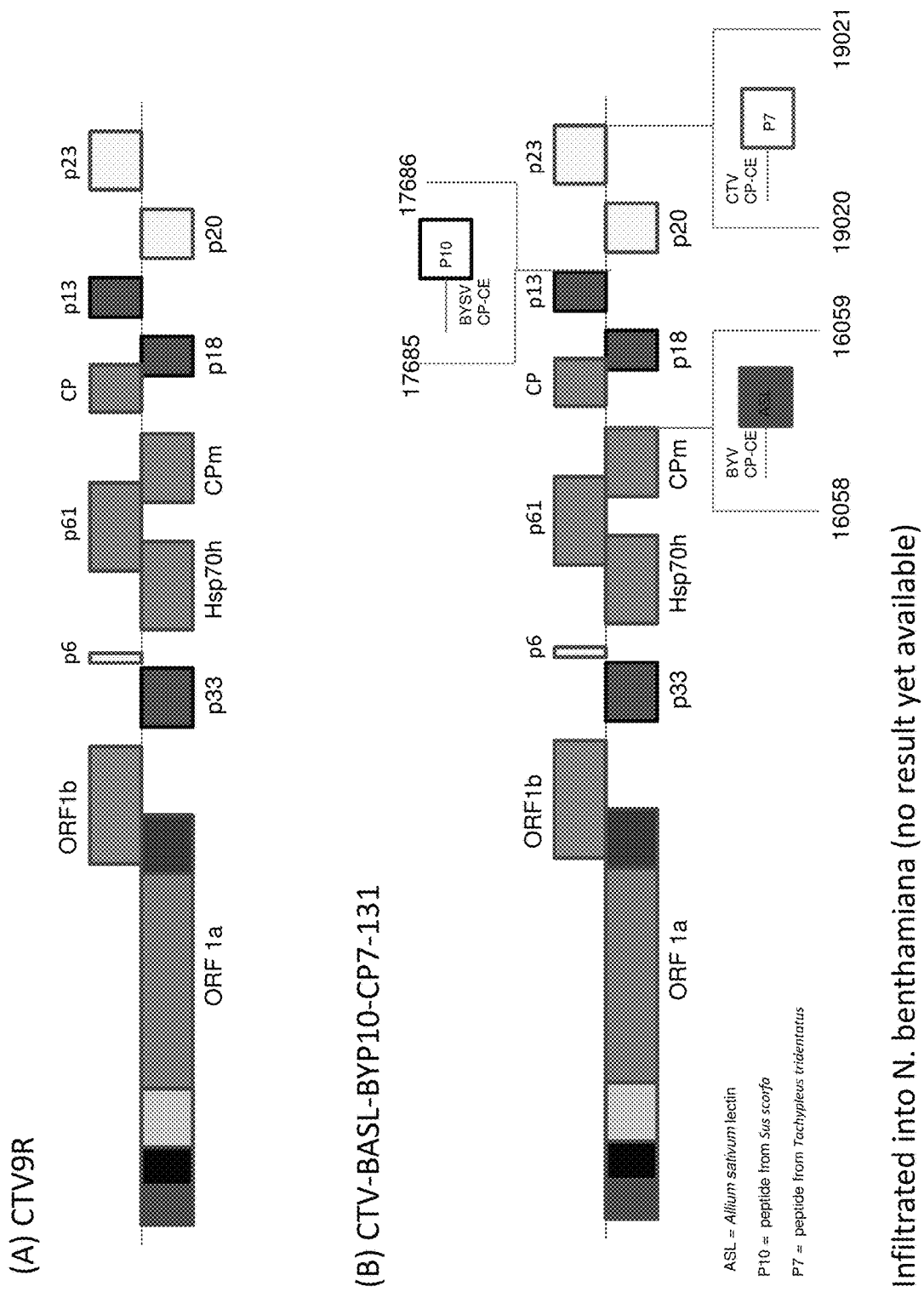

Fig. 26 3Gene vector (A) CTV9RΔp33

(B) CTV33-BGFP-BYGUS-GTMVCP-79

Infiltrated into N. benthamiana leaves and citrus infection attempted from infiltrated leaves
Did not wait for systemic infection in N. benthamiana Fig. 27 3 Gene vector
(A) CTV9RΔp33
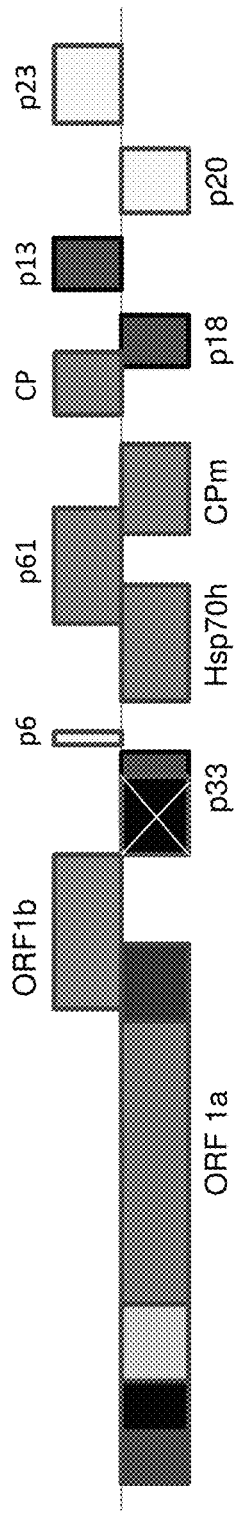
(B) CTV33-BGFP-Gb Fig. 28 3Gene vector
(A) CTV9RΔp33
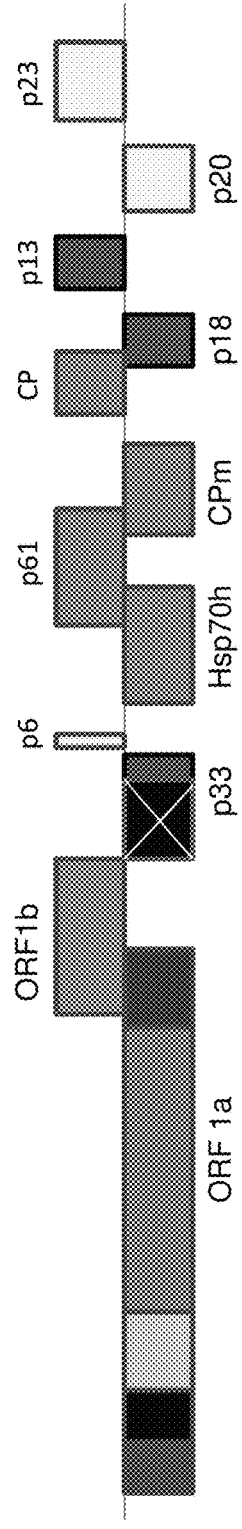
(B) CTV33-Δ13-BGFP-BYb

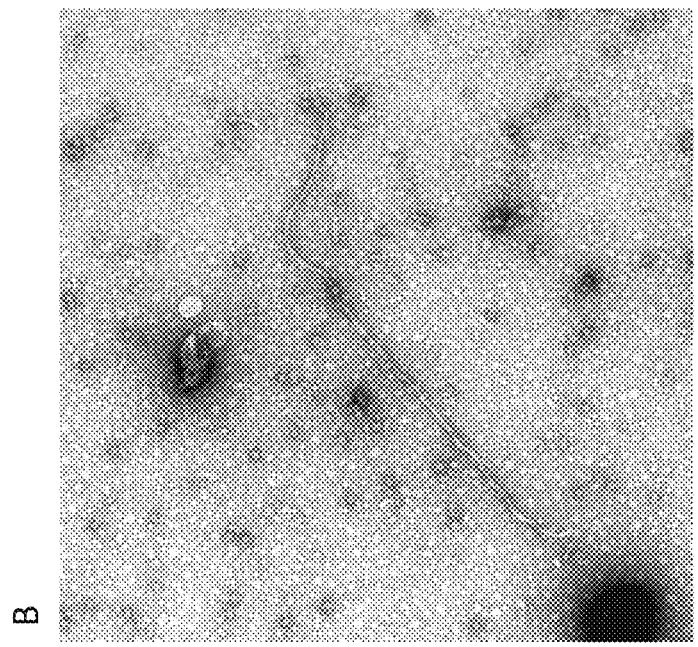
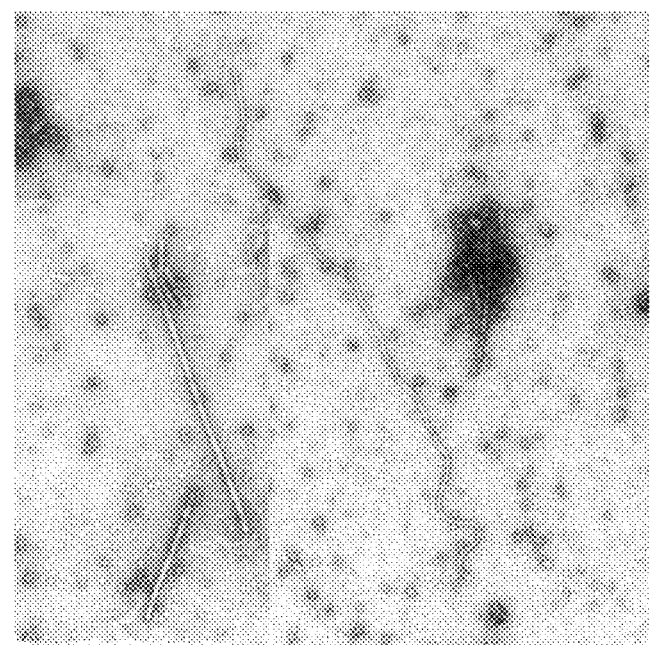
Fig. 29

FIG. 30

SEQUENCE LISTING

<160> NUMBER OF SEQ ID NOS: 87

<210> SEQ ID NO 1

```
<211> LENGTH: 27
<212> TYPE: DNA
<213> ORGANISM: Tobacco etch virus

<400> SEQUENCE: 1
atgaaaactt acaatgttgg agggatg                                        27

<210> SEQ ID NO 2
<211> LENGTH: 9
<212> TYPE: PRT
<213> ORGANISM: Tobacco etch virus

<400> SEQUENCE: 2

Met Lys Thr Tyr Asn Val Gly Gly Met
1               5

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
atgaagacct ataacgtagg tggcatg                                        27

<210> SEQ ID NO 4
<211> LENGTH: 21
<212> TYPE: DNA
<213> ORGANISM: Tobacco etch virus

<400> SEQUENCE: 4
gagaatcttt attttcagag t                                              21

<210> SEQ ID NO 5
<211> LENGTH: 7
<212> TYPE: PRT
<213> ORGANISM: Tobacco etch virus

<400> SEQUENCE: 5

Glu Asn Leu Tyr Phe Gln Ser
1               5

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gaaaacctat acttccaatc g                                              21

<210> SEQ ID NO 7
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agtcctcgag aaccacttag ttgtttagct atc                                 33
```

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ttatgcggcc gcaggccttg gacctatgtt ggccccccat ag                              42

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
taatcgtact tgagttctaa tatggctagc aaaggagaag aa                              42

<210> SEQ ID NO 10
<211> LENGTH: 100
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gccgcactag tatttaaatc ccgtttcgtc ctttagggac tcgtcagtgt actgatataa           60
gtacagactg gacctatgtt ggccccccat agggacagtg                               100

<210> SEQ ID NO 11
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
atggatgagc tctacaaatg attgaagtgg acggaataag ttcc                           44

<210> SEQ ID NO 12
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
ggaacttatt ccgtccactt caatcatttg tagagctcat ccat                           44

<210> SEQ ID NO 13
<211> LENGTH: 84
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcacgttgtg ctatagtacg tgccataata gtgagtgcta gcaaagtata acgctggtg           60 tttagcgcat attaaatact aacg                                           84

<210> SEQ ID NO 14
<211> LENGTH: 101
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagcttgctt ctacctgaca cagttaagaa gcggcataaa tcgaagccaa accctaaatt   60
ttgcaactcg atcaattgta acctagagcg aagtgcaatc a                      101

<210> SEQ ID NO 15
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tttagcgcat attaaatact aacgatggct agcaaaggag aagaa                   45

<210> SEQ ID NO 16
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
actgtgtcag gtagaagcaa gctgtcagat gaagtggtgt tcacg                   45

<210> SEQ ID NO 17
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ttggatttag gtgacactat agtggaccta tgttggcccc ccata                   45

<210> SEQ ID NO 18
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
gtaacctaga gcgaagtgca atcaatggct agcaaaggag aagaa                   45

<210> SEQ ID NO 19
<211> LENGTH: 86
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gcctaagctt acaaatactc ccccacaaca gcttacaata ctcccccaca cagcttacaa    60
atactccccc acaacagctt gtcgac                                        86

<210> SEQ ID NO 20
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ctccgtgaac accacttcat ctgaaaataa caaatctcaa cacaa                   45

<210> SEQ ID NO 21
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ttgtgttgag atttgttatt ttcagatgaa gtggtgttca cggag                   45

<210> SEQ ID NO 22
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggagtatttg taagcttagg ctcagatgaa gtggtgttca cggag                   45

<210> SEQ ID NO 23
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ccccacaaca gcttgtcgac atggctagca aaggagaaga acttt                   45

<210> SEQ ID NO 24
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
cgtgaacacc acttcatctg attcgacctc ggtcgtctta gttaa                   45

<210> SEQ ID NO 25
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
ttaactaaga cgaccgaggt cgaatcagat gaagtggtgt tcacg          45

<210> SEQ ID NO 26
<211> LENGTH: 137
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggcgatcacg acagagccgt gtcaattgtc gcggctaaga atgctgtgga tcgcagcgct    60
ttcactggag gggagagaaa aatagttagt ttgtatgcct taggaaggaa ctaagcacgt   120
tgtgctatag tacgtgc                                                 137

<210> SEQ ID NO 27
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tgacacggct ctgtcgtgat cgcctcagat gaagtggtgt tcacg           45

<210> SEQ ID NO 28
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gccacctacg ttataggtct tcattttgta gagctcatcc atgcc           45

<210> SEQ ID NO 29
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
aagacctata acgtaggtgg catgaaggct caatattcgg atcta           45

<210> SEQ ID NO 30
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
atgaaaactt acaatgttgg agggatgtta cgtcctgtag aaacc           45

<210> SEQ ID NO 31
<211> LENGTH: 45
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 31
ggtttctaca ggacgtaaca tccctccaac attgtaagtt ttcat               45

<210> SEQ ID NO 32
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgcagcagg gaggcaaaca atgattgaag tggacggaat aagtt               45

<210> SEQ ID NO 33
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
aacttattcc gtccacttca atcattgttt gcctccctgc tgcgg               45

<210> SEQ ID NO 34
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cttactctga aaataaagat tctctttgta gagctcatcc atgcc               45

<210> SEQ ID NO 35
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
aaagagaatc tttattttca gagtaaggga ccacgtgatt acaac               45

<210> SEQ ID NO 36
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cgattggaag tataggtttt cttgcgagta caccaattca ctcat               45

<210> SEQ ID NO 37
<211> LENGTH: 45
<212> TYPE: DNA
<213> ORGANISM: Artificial Sequence
<220> FEATURE:
```

<223> OTHER INFORMATION: Description of Artificial Sequence: Synthetic
    primer

<400> SEQUENCE: 37
caagaaaacc tatacttcca atcgatgtta cgtcctgtag aaacc            45

<210> SEQ ID NO 38
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 38
gtcactttgt ttagcgtgac ttagcagctt gcttctacct gacac            45

<210> SEQ ID NO 39
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 39
gtgtcaggta gaagcaagct gctaagtcac gctaaacaaa gtgac            45

<210> SEQ ID NO 40
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 40
ttagtctctc catcttgcgt gtagcagctt gcttctacct gacac            45

<210> SEQ ID NO 41
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 41
gtgtcaggta gaagcaagct gctacacgca agatggagag actaa            45

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
    primer

<400> SEQUENCE: 42
atggatgagc tctacaaatg agtttcagaa attgtcgaat cgcat            45

<210> SEQ ID NO 43
<211> LENGTH: 45
<212> TYPE: DNA
<213> ORGANISM: Artificial Sequence
<220> FEATURE:
<223> OTHER INFORMATION: Description of Artificial Sequence: Synthetic

```
      primer

<400> SEQUENCE: 43
atgcgattcg acaatttctg aaactcattt gtagagctca tccat                45

<210> SEQ ID NO 44
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
atggatgagc tctacaaatg agttaatacg cttctcagaa cgtgt                45

<210> SEQ ID NO 45
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
acacgttctg agaagcgtat taactcattt gtagagctca tccat                45

<210> SEQ ID NO 46
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
tttagcgcat attaaatact aacgatgtac ccatacgatg ttcca                45

<210> SEQ ID NO 47
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
tggaacatcg tatgggtaca tcgttagtat ttaatatgcg ctaaa                45

<210> SEQ ID NO 48
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
actgtgtcag gtagaagcaa gctgttactt gtacagctcg tccat                45

<210> SEQ ID NO 49
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 49
gtaacctaga gcgaagtgca atcaatggac tacaaagacg atgac          45

<210> SEQ ID NO 50
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtcactttgt ttagcgtgac ttagggcgat cacgacagag ccgtg          45

<210> SEQ ID NO 51
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
cacggctctg tcgtgatcgc cctaagtcac gctaaacaaa gtgac          45

<210> SEQ ID NO 52
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gtcactttgt ttagcgtgac ttagttcgac ctcggtcgtc ttagt          45

<210> SEQ ID NO 53
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
actaagacga ccgaggtcga actaagtcac gctaaacaaa gtgac          45

<210> SEQ ID NO 54
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cacaacgtct atatcatggc ctaggtttca gaaattgtcg aatcg          45

<210> SEQ ID NO 55
<211> LENGTH: 45
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 55
cgattcgaca atttctgaaa cctaggccat gatatagacg ttgtg            45

<210> SEQ ID NO 56
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggcatggacg agctgtacaa gtaattgaag tggacggaat aagtt            45

<210> SEQ ID NO 57
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
aacttattcc gtccacttca attacttgta cagctcgtcc atgcc            45

<210> SEQ ID NO 58
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
tcgctcttac cttgcgataa ctagcagctt gcttctacct gacac            45

<210> SEQ ID NO 59
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gtaacctaga gcgaagtgca atcaatgtta cgtcctgtag aaacc            45

<210> SEQ ID NO 60
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
ggtttctaca ggacgtaaca ttgattgcac ttcgctctag gttacaa          47

<210> SEQ ID NO 61
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccgcagcagg gaggcaaaca atgagtttca gaaattgtcg aatcg       45

<210> SEQ ID NO 62
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
cgattcgaca atttctgaaa ctcattgttt gcctccctgc tgcgg       45

<210> SEQ ID NO 63
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gtgtcaggta gaagcaagct gctagttatc gcaaggtaag agcga       45

<210> SEQ ID NO 64
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
atggatgagc tctacaaatg aagtctactc agtagtacgt ctatt       45

<210> SEQ ID NO 65
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
aatagacgta ctactgagta gacttcattt gtagagctca tccat       45

<210> SEQ ID NO 66
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
gcggatgcat tatttggttt tacaacaacg gtacgtttca aaatg       45

<210> SEQ ID NO 67
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67

```
atgaaaactt acaatgttgg agggatggct agcaaaggag aagaa                45
```

<210> SEQ ID NO 68
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68

```
ttcttctcct tgctagcca tccctccaac attgtaagtt ttcat                45
```

<210> SEQ ID NO 69
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69

```
gagaatcttt attttcagag taagggacca cgtgattaca acc                  43
```

<210> SEQ ID NO 70
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70

```
gaaaacctat acttccaatc gatggctagc aaaggagaag aact                 44
```

<210> SEQ ID NO 71
<211> LENGTH: 44
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71

```
agttcttctc ctttgctagc catcgattgg aagtataggt tttc                 44
```

<210> SEQ ID NO 72
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72

```
aagacctata acgtaggtgg catgaaggga ccacgtgatt acaac                45
```

<210> SEQ ID NO 73
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73

```
ccctccaaca ttgtaagttt tcatttgcga gtacaccaat tcact                45
```

<210> SEQ ID NO 74
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gagaatcttt attttcagag taaggctcaa tattcggatc taaag           45

<210> SEQ ID NO 75
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgattggaag tataggtttt cttcggattc caaacctgaa tgaac           45

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gccacctacg ttataggtct tcatgatgaa gtggtgttca cggag           45

<210> SEQ ID NO 77
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
actctgaaaa taaagattct cgatgaagtg gtgttcacgg agaac           45

<210> SEQ ID NO 78
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
catttacgaa cgatagccat ggctagcaaa ggagaagaa                  39

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgagttaatt aaagcctttg cttcagcgtt tctgaaagtg ctttc           45

-continued

<210> SEQ ID NO 80
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gacaaggcct gtctcatacc agttcccgtc cccatctttc c            41

<210> SEQ ID NO 81
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
cgagttaatt aagccgaacc caaggaaaga acttttctca tg           42

<210> SEQ ID NO 82
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gacaaggcct ttattcatag atccaggatt cactggcatt g            41

<210> SEQ ID NO 83
<211> LENGTH: 440
<212> TYPE: DNA
<213> ORGANISM: Aeuquorea victoria

<400> SEQUENCE: 83
gctagcaaag gagaagaact tttcactgga gttgtcccaa ttcttgttga attagatggt    60
gatgttaatg ggcacaaatt ttctgtcagt ggagagggtg aaggtgatgc tacatacgga   120
aagcttaccc ttaaatttat ttgcactact ggaaaactac ctgttccatg gccaacactt   180
gtcactactt tctcttatgg tgttcaatgc ttttcccgtt atccggatca tatgaaacgg   240
catgactttt tcaagagtgc catgcccgaa ggttatgtac aggaaagaac tatattttc    300
aaagatgacg ggaactacaa gacgcgtgct gaagtcaagt ttgaaggtga tacccttgtt   360
aatcgtatcg agttaaaagg tattgatttt aaagaagatg gaaacattct cggacacaaa   420
ctcgagtaca actataactc                                              440

<210> SEQ ID NO 84
<211> LENGTH: 391
<212> TYPE: DNA
<213> ORGANISM: citrus macrophylla

<400> SEQUENCE: 84
agcctttgct tcagcgtttc tgaaagtgct ttcaacttgc gatatggttt ccgagatagt    60
gaaccgatgg gtcagagcct gaaaattcga gttaaaacga ggacaaggaa gggtttctgt   120
ccttcgaagg cggtttgtgt ggactaccca agaccagata ttgataatac atctaatttc   180
ttggaagctg cttacttatc ttcgtcattt cgtacttctc ctcgtccttc taagccgttg   240

-continued

```
aaagttgtaa ttgctggtgc aggtttggct ggtttatcaa ctgcaaaata tttggcagat    300
gcaggccaca agcctttgtt actggaagca agagatgttc taggtggaaa gatagctgcc    360
tggaaagatg gggacgggaa ctggtagaga c                                   391

<210> SEQ ID NO 85
<211> LENGTH: 459
<212> TYPE: DNA
<213> ORGANISM: Diaphorina citri

<400> SEQUENCE: 85
gccgaaccca aggaaagaac tttctcatg atcaagcccg atggcgttca aagaggactt      60
gtgggaaaca tcatcaaacg ctttgaagac aaaggcttca aattggtggc catgaaattc    120
gtttggccat ccgaagaact tctgaagcaa cactactcag atttggccac caaacctttc    180
ttccctggtc ttgtcaaata catgtcatct ggacctgttg ttcctatggt gtgggaagga    240
ttgaacattg tcaaaactgg acgtgtgatg cttggagcca ccaaccctgc tgactctgcc    300
ccaggaactg tcagaggaga cctctgcatc caagttggaa gaaacatcat gcatggatca    360
gactctgttg aatctgcaaa gaaagaaatt gccttatggt tcactgagaa agaagtcatt    420
ggatggacaa atgccagtga atcctggatc tatgaataa                           459

<210> SEQ ID NO 86
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
cgagttaatt aagctagcaa aggagaagaa cttttcactg                           40

<210> SEQ ID NO 87
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
gacaaggcct gagttatagt tgtactcgag tttgtgtc                             38
```

CITRUS TRISTEZA VIRUS BASED VECTORS FOR FOREIGN GENE/S EXPRESSION

CROSS-REFERENCE TO RELATED APPLICATIONS

This application is a continuation of U.S. application Ser. No. 14/269,637 filed May 5, 2014, which is a continuation-in-part of U.S. application Ser. No. 13/624,294 filed Sep. 21, 2012 and further claims the benefit of U.S. Provisional Application No. 61/537,154 filed Sep. 21, 2011 and U.S. Provisional Application No. 61/970,975 filed Mar. 27, 2014, all of which are incorporated herein by reference in their entirety.

BACKGROUND

The early development of viral vectors was aimed at the inexpensive production of high levels of specialty proteins that could be scaled up in the field. The first attempt at a plant viral vector utilized Cauliflower mosaic virus, a dsDNA virus (Brisson et al., 1984; Gronenborn et al., 1981). However, this vector was too unstable to be useful (Bitterer et al., 1990). The development of reverse genetics systems amenable for manipulation of RNA viruses made many more viruses candidates for vector development (Ahlquist et al., 1984).

Virus vectors are key ingredients in basic research and have great potential for commercial applications. Lack of stability of foreign inserts has been a major drawback for potential applications of virus vectors for commercial protein expression in field applications.

SUMMARY

The present disclosure is based on multiple studies testing the vector limits of using CTV to express foreign genes ranging from 806 to 3480 nucleotides in size. In one embodiment, gene cassettes were introduced into the CTV genome as replacement of the p13 gene. In other embodiments, a gene was inserted at different locations (e.g., p13-p20, p20-p23 and p23-3'NTR (non-translated region)). In another embodiment, a fusion to p23 and protease processing were tested. In alternative embodiments, genes were inserted behind IRES sequences to create bi-cistronic messages.

Twenty seven expression vectors have been created and tested in *Nicotinia benthamiana* protoplasts and plants. Remarkably, most of the newly developed vector constructs disclosed herein replicated, spread systemically in plants, and produced their foreign gene(s). The highest expressing vectors tested include the "add a gene" constructs having an insertion between the p13 and p20 genes or between the p23 gene and the 3'NTR. Similarly, the vectors with the inserted gene replacing the p13 gene effectively expressed different reporter genes. However, optimal expression of the reporter gene depended both on the size and location of the insertion. Optimal expression of smaller genes are from positions nearer the 3' terminus, whereas larger genes are optimally expressed from more internal positions.

Efficient expression of two genes simultaneously from the same vector has been accomplished in both *N. benthamiana* and citrus. The novel CTV constructs disclosed herein have genomes with unique elasticity capable of accommodating and expressing foreign gene/s by different strategies.

Engineering an effective vector requires a balance between different factors. The vector needs to be designed such that replication and systemic movement in the plant are reduced minimally while the level of expression of the foreign protein is maximal (Shivprasad et al., 1999). The final factor is the stability of the vector. In general, the vector's usefulness is directly correlated with its stability. Stability is a product of reduced recombination and increased competitiveness of the vector with the resulting recombinants that have lost part or all of the inserted sequences.

BRIEF DESCRIPTION OF DRAWINGS

FIG. 1. GFP replacement of p13 to produce CTV based expression vectors. (A) Schematic representation of CTV9RΔp33 (Boxes represent open reading frames with blue outline of boxes represent the replication gene block whereas the red outline represent the closterovirus conserved gene block (Karasev, 2000). The black circle and black boxes outline represent silencing suppressors (Lu et al., 2004). Gold box outline represent genes dispensible for the infection of some citrus genotypes (Tatineni et al., 2008). Filled black rectangle represents the deletion of the p33 controller elements and ORF (nts 10858-11660 Genebank Accession # AY170468) (Satyanarayana et al., 1999; 2000; 2003)). Arrows indicate the processing of the leader proteases of CTV, LP1 and LP2 are two tandem leader protease, MT (methyl transferase), Hel (Helicase), RdRp (RNA dependent RNA polymerase, 433 (deletion of the 33 kda protein sequence), p6 (6 kda protein), Hsp70h (heat shock protein 70 homologue), p61 (61 kda protein), CPm (minor coat protein), CP (major coat protein, inter cellular silencing suppressor), p18 (18 kda protein), p13 (13 kda protein), p20 (20 kda protein, inter/intra cellular silencing suppressor), p23 (23 kda protein, intracellular silencing suppressor) and modification to produce expression vectors CTV33-Δ13-BY-GFP-57 (C57), CTV33-Δ13-G-GFP-65 (C65), CTV33-Δ13-B-GFP-66 (C66) with the CP-CE of BYSV, GLRaV-2 and BYV driving GFP, respectively. (B) Northern blot analysis of wild type CTV (WT) and CTV based expression vector transfected to *N. benthamiana* protoplast (T) and passaged to a new set of protoplasts (P). (C) Representative sample of fluorescence in *N. benthamiana* infected with either of the three constructs CTV33-Δ13-BY-GFP-57, CTV33-Δ13-G-GFP-65, CTV33-Δ13-B-GFP-66 magnified under a fluorescent stereoscope. (D) Representative sample of fluorescence in the phloem of citrus bark pieces infected with constructs CTV33-Δ13-G-GFP-65 and CTV33-Δ13-B-GFP-66 with high (left) and low (right) magnification under a fluorescent stereoscope.

FIG. 2 GUS replacement of p13 to produce CTV based expression vectors. (A) Schematic representation of CTV9RΔp33 and its modification creating expression vector CTV33-Δ13-BY-GUS-61 in which the p13 and its controller element is replaced by GUS under the control of CP-CE of BYSV. (B) Northern blot hybridization analysis of wild type CTV (WT) and CTV based expression vector CTV33-Δ13-BY-GUS-61 (C61) transfected to *N. benthamiana* protoplast (T) and passaged to a new set of protoplasts (P). (C) Representative sample of GUS activity in the bark pieces of citrus trees infected with construct CTV33-Δ13-BY-GUS-61 (right) and the GUS solution before fixing of the bark pieces (left) (A=Healthy control, B=infect).

FIG. 3 GFP insertion between p13 and p20 to produce CTV based expression vectors. (A) Schematic representation of CTV9RΔp33 and modification by inserting between p13 and p20 of GFP ORF under the control of BYSV creating expression vector CTV33-13-BY-GFP-69 (B)

Northern blot hybridization analysis of transfected protoplast with the wild type virus (WT) and expression vector CTV33-13-BY-GFP-69 (C69) from transcripts (T) and their passages (P). Representative sample of fluorescence in *N. benthamiana* (C) and peeled bark phloem pieces of *C. macrophylla* (D) infected with CTV33-13-BY-GFP-69 magnified under a fluorescent stereoscope.

Figure 4:
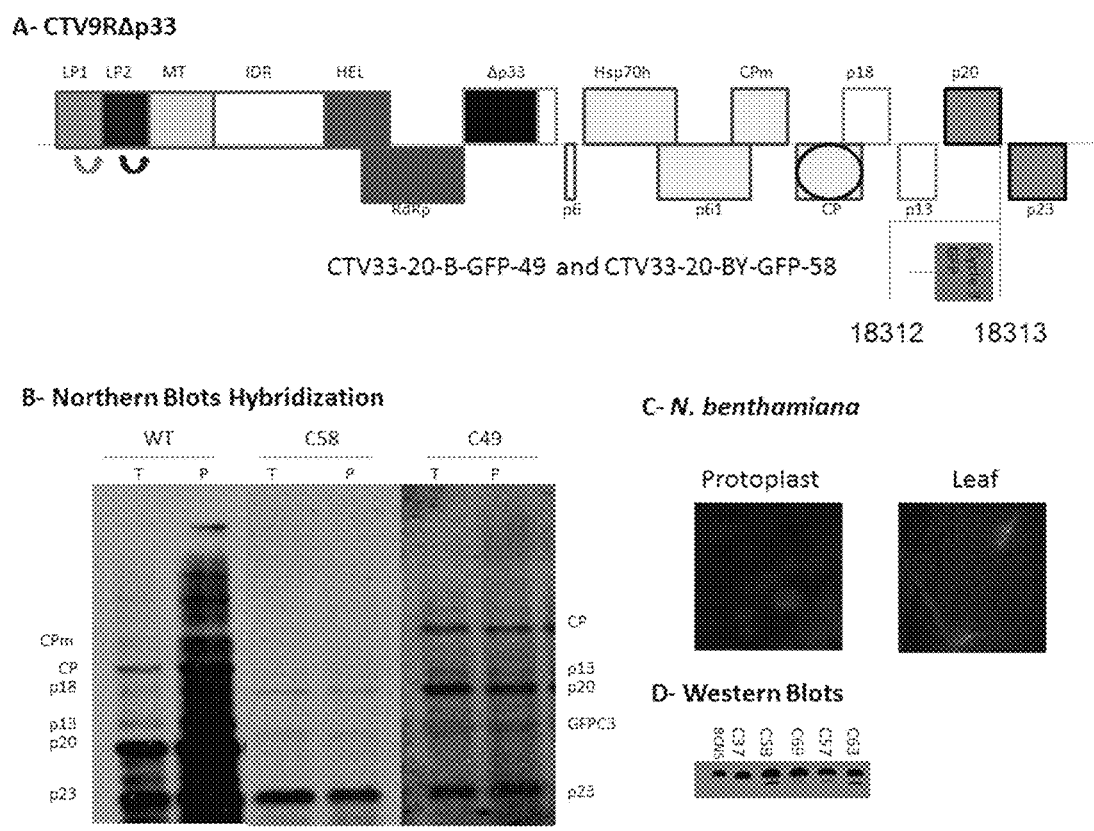

FIG. 4 GFP insertion between p20 and p23 to produce CTV based expression vectors. (A) Schematic representation of CTV9RΔp33 and its modification producing expression vector CTV33-20-B-GFP-49 and CTV33-20-BY-GFP-58, respectively. (B) Northern blot hybridization analysis of transfected protoplast with the wild type virus (WT) and expression vectors CTV33-20-B-GFP-49 (C49) and CTV33-20-BY-GFP-58 (C58) from transcripts (T) and their passages (P). (C) Flourescence under UV light of protoplast (right) and the leaf (left) showing lack of efficient movement of the vector. (D) Western blot analysis of the same gene inserted at different locations in the CTV genome. BCN5 (Folimonov et al., 2007) original CTV vector (contains GFP under BYV promoter between CPm and CP), constructs CTV33-23-BY-GFP-37 (C37, insertion of BYSV driving GFP behind p23), CTV33-20-BY-GFP-58 (C58, insertion of BYSV driving GFP between p20 and p23), CTV33-13-BY-GFP-69 (C69, insertion of BYSV driving GFP between p13 and p20), CTV33-Δ13-BY-GFP-57 (C57, replacement of p13 gene with BYSV CP-CE driving GFP) and CTV33-27-BY-GFP-63 (C63, Insertion of BYSV CP-CE driving GFP ORF between CPm and CP).

Figure 5:
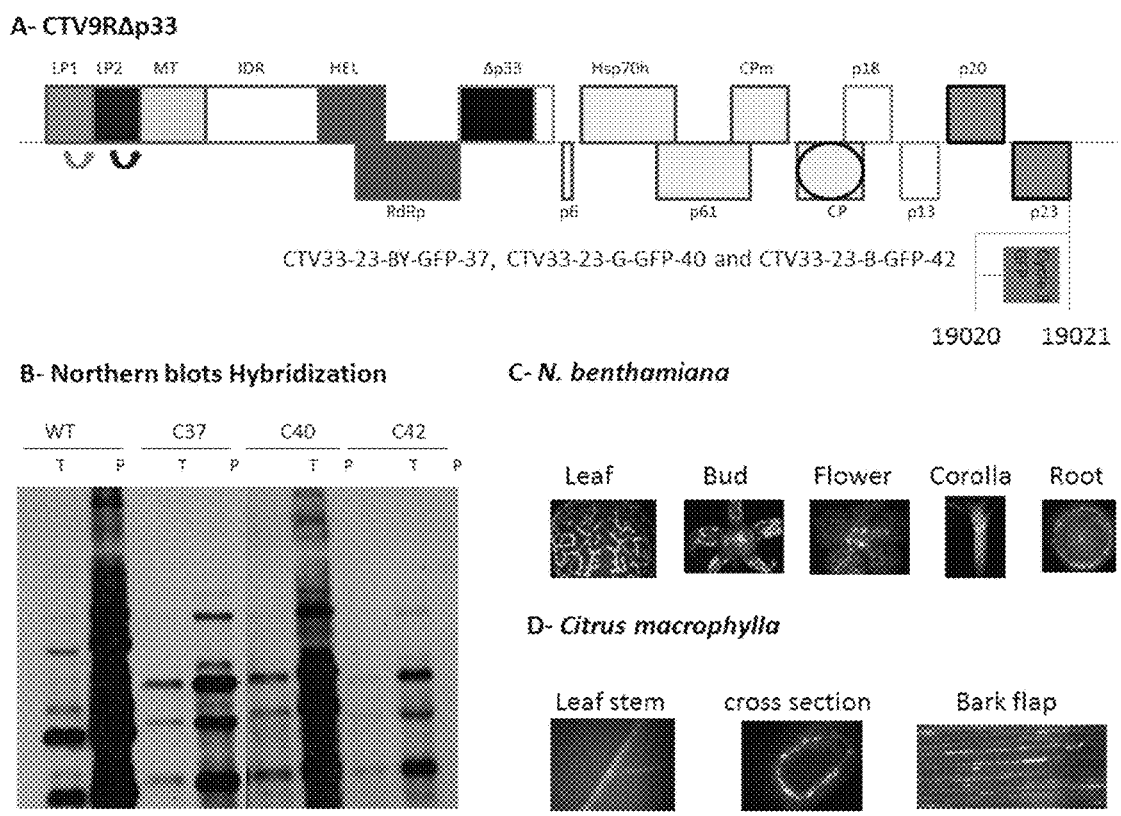

FIG. 5 GFP insertion between p23 and 3'NTR to produce CTV based expression vectors. (A) Schematic representation of CTV9RΔp33 and its modification by insertion of GFP behind p23 under control of CP-CE of BYSV, GLRaV-2 and BYV creating expression CTV33-23-BY-GFP-37 (C37), CTV33-23-G-GFP-40 (C40) and CTV33-23-B-GFP-42 (C42), respectively. (B) Northern blot hybridization analysis of transfected protoplast with the wild type virus (WT) and expression vectors CTV33-23-BY-GFP-37, CTV33-23-G-GFP-40 and CTV33-23-B-GFP-42 from transcripts (T) and their passages (P). (C) Representative sample of fluorescence in *N. benthamiana* infected with either of the three constructs CTV33-23-BY-GFP-37, CTV33-23-G-GFP-40 and CTV33-23-B-GFP-42 magnified under a fluorescent stereoscope. (D) Representative sample of fluorescence in the phloem tissue of *Citrus macrophylla* infected with constructs CTV33-23-BY-GFP-37 and CTV33-23-G-GFP-40.

FIG. 6 GUS insertion between p23 and 3'NTR insertion between p23 and 3'NTR to produce CTV based expression vectors. (A) Schematic representation of CTV9RΔp33 and modification by insertion of GUS ORF under control of BYSV CP-CE between p23 and 3'NTR creating expression vector CTV33-23-BY-GUS-60 (C60). (B) Northern blot hybridization analysis of transfected protoplast with the wild type virus (WT) and expression vectors CTV33-23-BY-GUS-60 from transcripts (T). (C) Enzymatic activity of the GUS protein in *N. benthamiana* tissue and citrus phloem bark pieces (Blue color indicate infected plant and colorless tissue and solution indicate healthy control and GUS solution subject to the same treatment.

FIG. 7 GFP inserted behind IRES sequences to create CTV based expression vectors. (A) Schematic representation of CTV9RΔp33 and CTVΔCla 333R and their modification behind p23 creating expression vectors CTV33-23-ITEV-GFP-41; CTV33-23-I3×ARC-GFP-43 represent the TEV 5'NTR IRES and 3×ARC-1 IRES, respectively and CTVp333R-23-ITEV-GFP; CTVp333R-23-I3×ARC-GFP representing the TEV 5'NTR IRES and 3×ARC-1 IRES, respectively. (B) 1—Northern blot hybridization analysis from tranfected *N. benthamiana* protoplast with wild type virus (WT), CTV33-23-ITEV-GFP-41 (C41) and CTV33-23-I3×ARC-GFP-43 (C43); T=RNA isolated from transcript transfected protoplast and P=RNA isolated from virion transfected protoplast isolated from RNA transfected protoplast. 2—Northern blot hybridization analysis from protoplast transfected with CTVp333R-23-ITEV-GFP (Lane A); CTVp333R-23-I3×ARC-GFP (lane B), CTVp333R (lane C) and CTVp333R-23-B-GFP (BYV CP-CE driving the expression of GFP behind p23) (Lane D).

Figure 8:
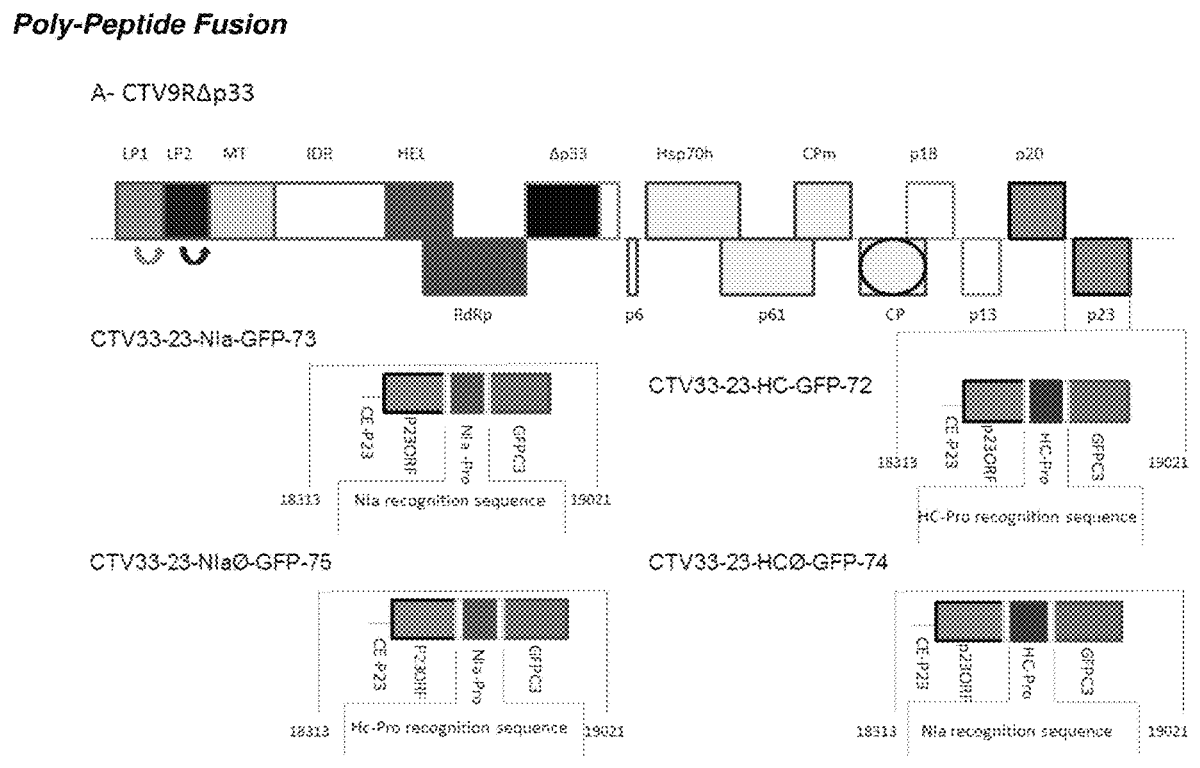

FIG. 8 GFP and a protease fused to p23 to create CTV based expression vectors. (A) Schematic representation of CTV9RΔp33 and the modifications by fusing two TEV proteases (NIa and HC-Pro) and their recognition sequences to create expression vectors CTV33-23-HC-GFP-72, CTV33-23-NIa-GFP-73, CTV33-23-HCØ-GFP-74 and CTV33-23-NIaØ-GFP-75.

Figure 9:
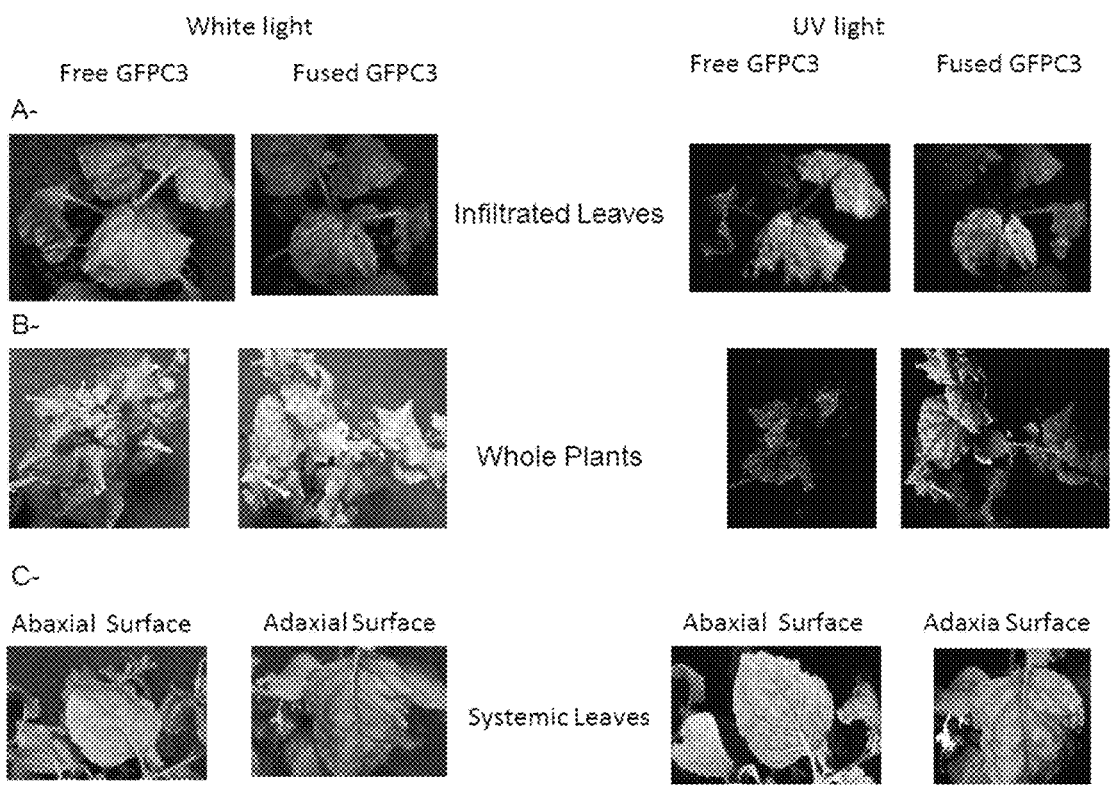

FIG. 9 Comparison of Florescence in *N. benthamiana*. (A) Comparison of fluorescence in infiltrated leaves of representative samples of constructs CTV33-23-HC-GFP-72, CTV33-23-NIa-GFP-73, CTV33-23-HCØ-GFP-74 and CTV33-23-NIaØ-GFP-75 (GFP fused) and CTV33-23-BY-GFP-37, CTV33-23-G-GFP-40 and CTV33-23-B-GFP-42 (free GFP) under hand held UV light (Right) and the same leaves under white light (left). (B) Comparison on whole plant level between representative samples of constructs CTV33-23-HC-GFP-72 and CTV33-23-NIa-GFP-73 (fused GFP) and CTV33-23-BY-GFP-37, CTV33-23-G-GFP-40 and CTV33-23-B-GFP-42 (GFP under its own controller element behind p23 (Free GFP)) under hand held UV light (Right) and same plants under white light (Left). (C) Comparison between the abaxial (Lower) and adaxial (upper) leaf surfaces of the same representative leaf sample of constructs CTV33-23-HC-GFP-72 and CTV33-23-NIa-GFP-73 under hand held UV light (Right) and white light (Left).

Figure 10:
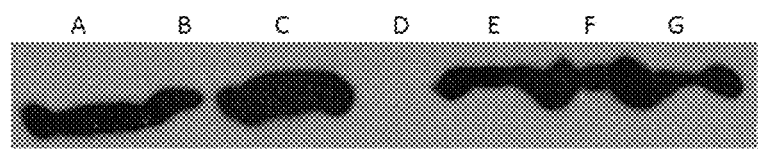

FIG. 10 Western blot analysis of different expression vectors infiltrated into *N. benthamiana* leaves using GFP antibody. A=CTV9RΔp33GFP (GFP inserted under the BYV CP-CE controller element between CPm and CP (produces free GFP)(Tatineni et al., 2008)), B=CTV33-23-BY-GFP-HC-GUS-51, C=CTV33-23-G-GFP-NIa-GUS-54, D=Empty well; E=CTV33-Δ13-BY-GFP-NIa-GUS-78, F=CTV33-23-HC-GFP-72, G=CTV33-23-NIa-GFP-73.

Figure 11:
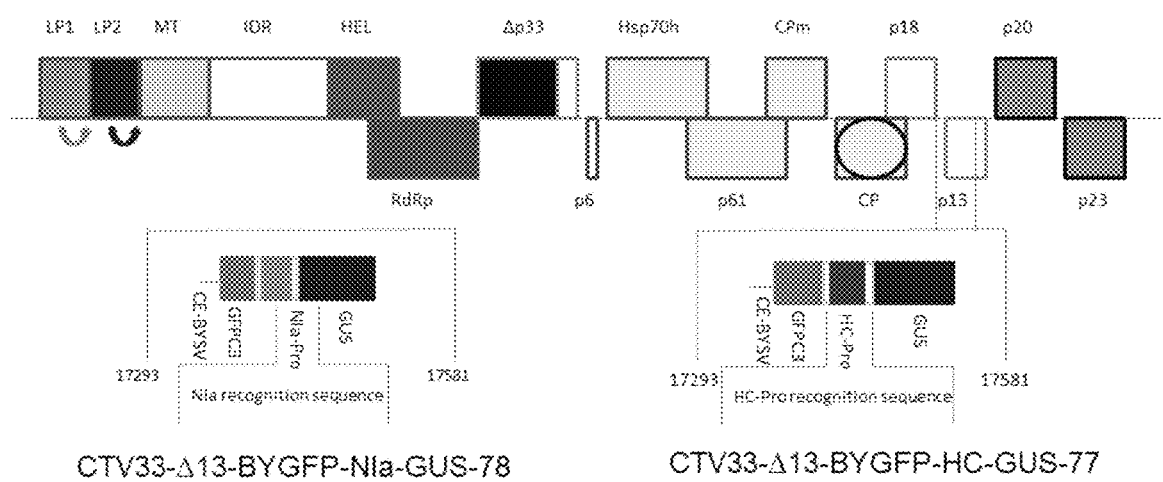

FIG. 11 Hybrid gene (GFP/Protease/GUS fusion) replacement of p13 to create expression vectors. (A) Schematic representation of CTV9R Δ p33 and its modification to create expression vectors CTV33-Δ13-BYGFP-HC-GUS-77 and CTV33-Δ13-BYGFP-NIa-GUS-78 with the two fusion genes under the control of BYSV CP-CE with TEV HC-Pro and NIa spanned by their proteolysis recognition sequence seperating GFP and GUS, respectively. (B) Activity of the reporter genes in *N. benthamiana* and *Citrus macrophylla*. (a.) Representative sample of *N. benthamiana* plant infected with either CTV33-Δ13-BYGFP-HC-GUS-77 or CTV33-Δ13-BYGFP-NIa-GUS-78 *N. benthamiana* under white light and (b.) the same plant under UV light (c.) Two pictures of peeled phloem bark pieces of *C. macrophylla* infected with construct CTV33-Δ13-BYGFP-NIa-GUS-78 under a fluorescent stereoscope (d.) Representative sample of GUS activity in systemic *N. benthamiana* leaves, control leaf (Left) and infected leaf (right) (e.) Peeled bark phloem pieces and GUS solution of healthy *C. macrophylla* plant (f.) Peeled bark phloem pieces of *C. macrophylla* plant infected with construct CTV33-Δ13-BYGFP-NIa-GUS-78.

FIG. 12 Stability of Constructs in *N. benthamiana*. (A) Upper leaf from Agro-inoculated *N. benthamiana* plants carrying the binary vector CTV33-Δ13-BYGFP-HC-GUS-77 (GFP/HC-Pro/GUS) pictured under fluorescent microscope. (B) The same leaf was tested for GUS activity indicating almost perfect overlap between the two reporter genes.

FIG. 13 Hybrid gene (GFP/Protease/GUS fusion) between p23 and 3'NTR to create expression vectors. (A) Schematic representation of CTV9R Δ p33 and its modification to produce expression vectors CTV33-23-BY-GFP-HC-GUS-51 and CTV33-23-BY-GFP-NIa-GUS-52 has the BYSV CP-CE driving the hybrid genes that contain HC-Pro and Ma proteases respectively; CTV33-23-G-GFP-HC-GUS-53 (C53) and CTV33-23-G-GFP-NIa-GUS-54 (C54) are GLRaV-2 driven fusion genes that contain the HC-Pro and NIa proteases, respectively; CTV33-23-BY-GFP-HC-GUS-55 (C55) and CTV33-23-BY-GFP-NIa-GUS-56 (C56) are BYV driven fusion genes that contain HC-Pro and NIa proteases, respectively. (B) Northern blot hybridization analysis of transfected protoplast with wild type virus (WT), C53, C54, C55 and C56 constructs.

Figure 14:
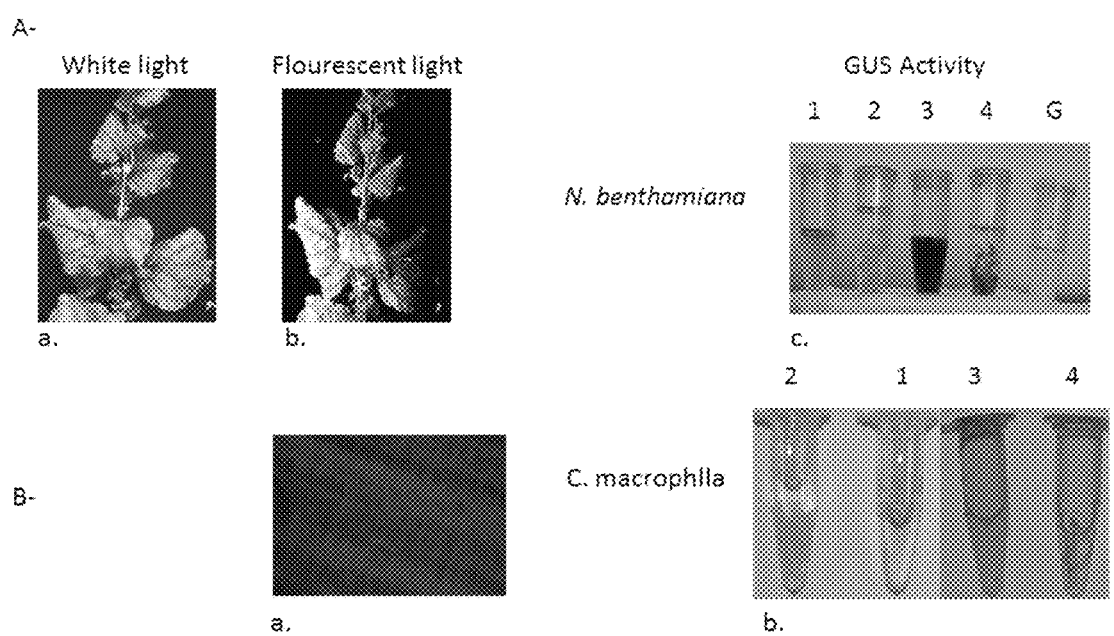

FIG. 14 Activity of reporter genes generated by insertion of the Hybrid gene (GFP/Protease/GUS fusion) behind p23. (A) Activity of the reporter genes in *N. benthamiana*. plants (a.) Representative sample of *N. benthamiana* plant infected with CTV33-23-BY-GFP-HC-GUS-51, CTV33-23-G-GFP-HC-GUS-53, CTV33-23-BY-GFP-NIa-GUS-52 or CTV33-23-G-GFP-NIa-GUS-54 under white light and (b.) the same plant under hand held UV light (c.) Representative sample of GUS activity in infected systemic *N. benthamiana* leaves and control leaves (tubes 1 &2 represent the solution before fixing and tissues in fixing solution, respectively from healthy leaves whereas 3&4 represent the solution and tissues from infected leaves, respectively, G tube is the GUS assay buffer (B.) Activity of reporter genes in *C. macrophylla* (a.) Picture of peeled phloem bark pieces of *C. macrophylla* infected with construct CTV33-23-BY-GFP-HC-GUS-51 under a fluorescent stereoscope (b.) Peeled bark phloem pieces GUS activity in infected and healthy *C. macrophylla* plants (tubes 1 &2 represent the solution and tissues in fixing solution from healthy leaves whereas 3&4 represent the solution and tissues from infected leaves, respectively.

Figure 15:
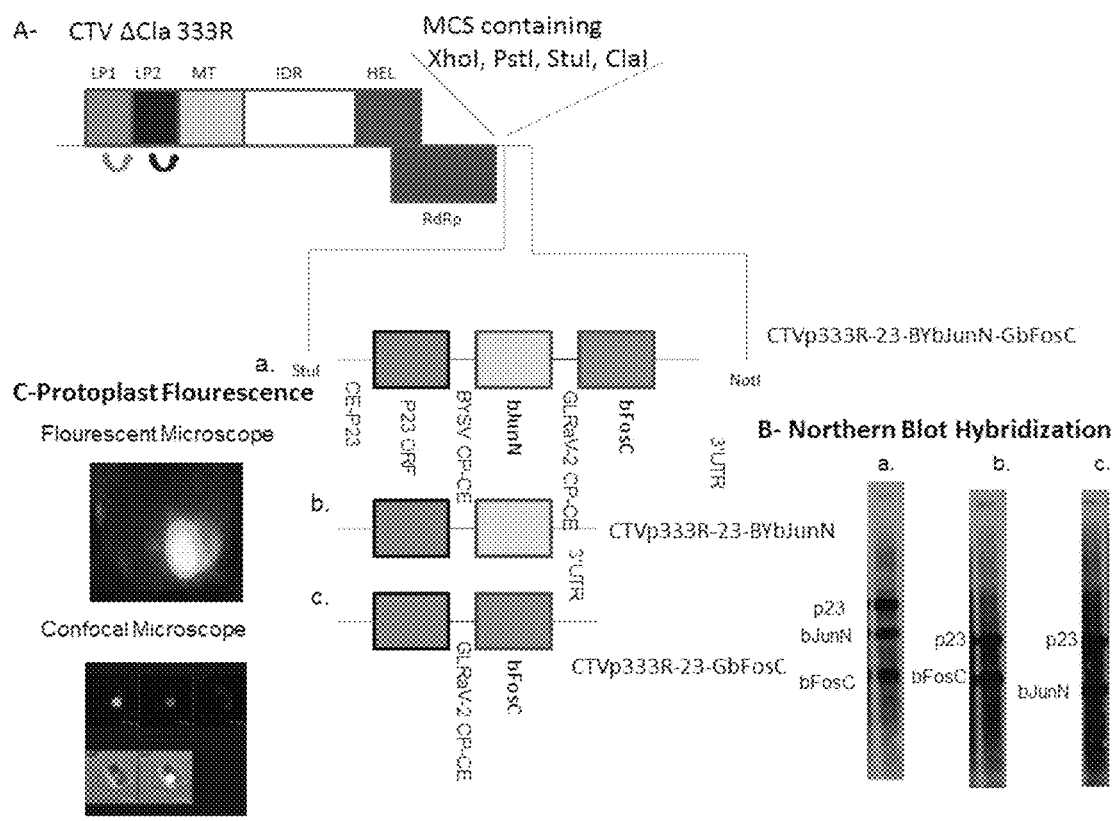

FIG. 15 Bimolecular Fluorescence complementation (BiFC) proof of concept. (A) Schematic representation of CTVΔ Cla 333R (Gowda et al., 2001, Satyanarayana et al., 2003) replicon and its modification to create expression replicons: (a.) Insertion of both BiFC genes between p23 and 3'NTR giving rise to CTVp333R-23-BYbJunN-GbFosC and the controls with one gene behind p23, CTVp333R-23-BYbJunN (b.) or CTVp333R-23-GbFosC (c.). (B) Northern blot hybridization analysis of transfected protoplast with CTVp333R-23-BYbJunN-GbFosC (Lane a.), CTVp333R-23-BYbJunN (Lane c.) and CTVp333R-23-GbFosC (Lane b.). (C) Flourescence of a transfected protoplast when pictured under a stereoscope (Upper) or a laser scanning confocal microscope (lower) indicating the Flourescence from the nucleus.

Figure 16:
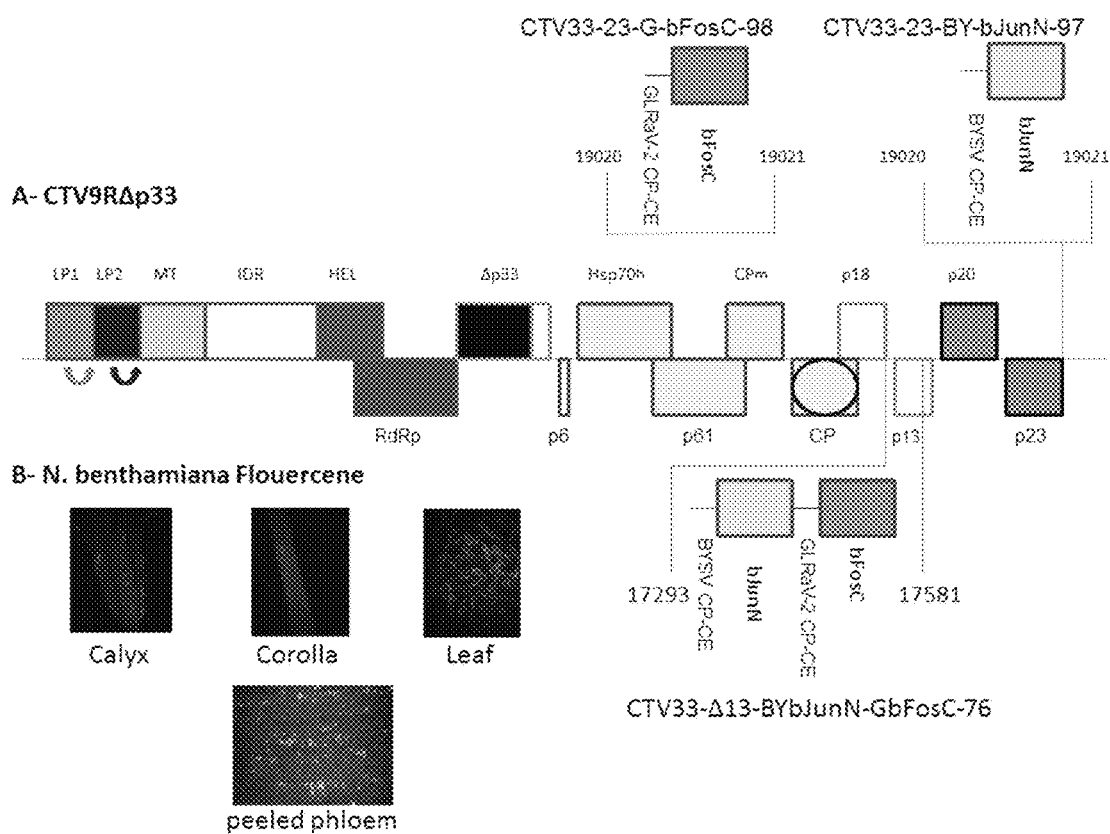

FIG. 16 BiFC gene replacement of p13 to produce CTV based expression vectors. (A) Schematic representation of CTV9RΔp33 and modification to produce vector CTV33-Δ13-BYbJunN-GbFosC-76 and the control vectors CTV33-23-G-bFosC-98 and CTV33-23-BY-bJunN-97 (insertion behind p23 nts 19020-19021). (B) Representative sample of *N. benthamiana* fluorescence in systemically infected plants.

Figure 17:
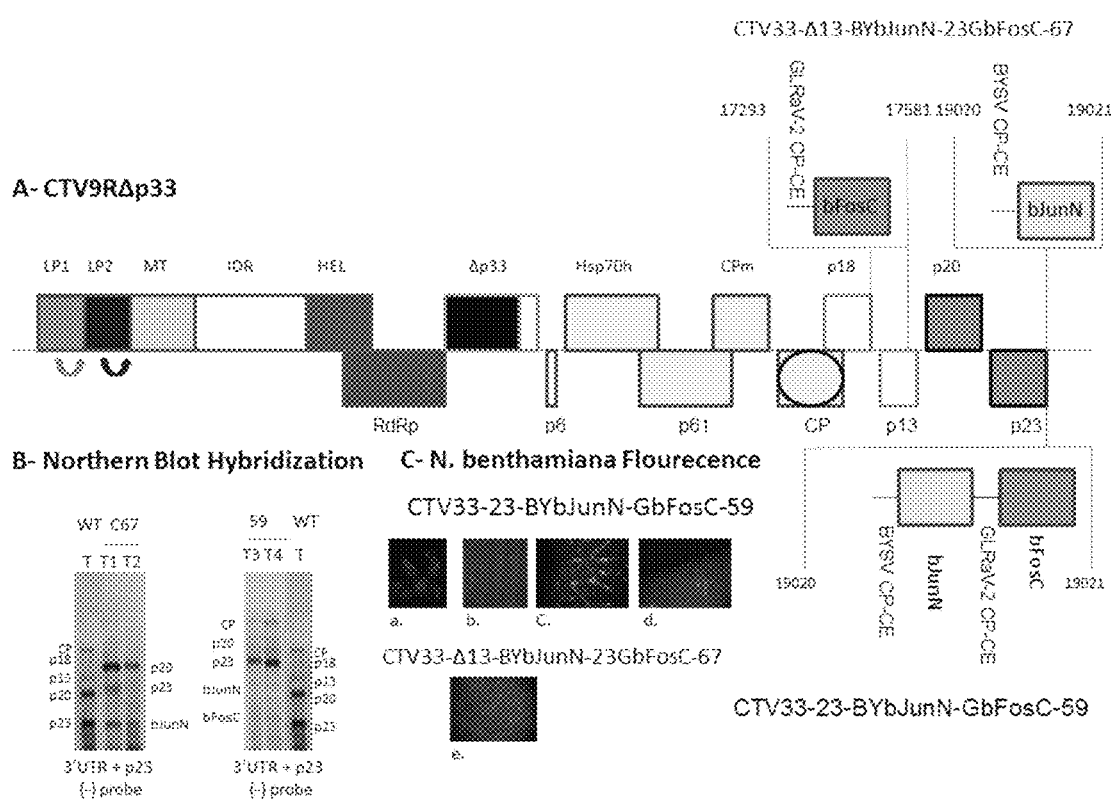

FIG. 17 CTV based expression vector built to simultaneously express two genes from two controller elements. (A) Schematic representation of CTV9RΔp33 and its modification to produce expression vectors CTV33-23-BYbJunN-GbFosC-59 and CTV33-Δ13-BYbJunN-23-GbFosC-67. (B) Northern blot hybridization analysis of the RNA transfected protoplast with the wild type virus (WT,T), two clones of CTV33-Δ13-BYbJunN-23-GbFosC-67 (C67, T1 and T2) and two clones of CTV33-23-BY-bJunN-Gb-FosC-59 (C59, T3 and T4) probed with 3'NTR+p23 (Satyanarayana et al., 1999). (C) Flourescence of *N. benthamiana* plant parts under a fluorescent stereo microscope (CTV33-23-BY-bJunN-Gb-FosC-59=a., b., c. and d; CTV33-Δ13-BYbJunN-23-Gb-FosC-67=e.) (a.) bud (b.) Corolla, (c.) systemic leaves, (d.) peeled bark phloem pieces and (e.) infiltrated leaf FIG. 18 CTV based expression vector built to simultaneously express two genes from two controller elements. (A) Schematic representation of CTV9RΔp33 and its modification to produce expression vectors CTV33-Δ13-BYGUS-23-GGFP-71. (B) Northern blot hybridization analysis of the RNA transfected protoplast with the wild type virus (WT) and the CTV33-Δ13-BYGUS-23-GGFP-71 (C71) expression vector probed with 3'NTR+p23 (Satyanarayana et al., 1999). (C) Biological activity of reporter genes in *N. benthamiana* and Citrus. *N. benthamiana* plant under white light (a.) and hand held UV light (b.). (c.) GUS activity from healthy (tube 1 (assay solution) &2 (tissue) and infected *N. benthamiana* (tube 3 (assay solution) and tube 4 (tissue). (d.) Peeled bark phloem pieces under fluorescent microscope and (e.) GUS assay activity in citrus similar to (c.)

Figure 19:
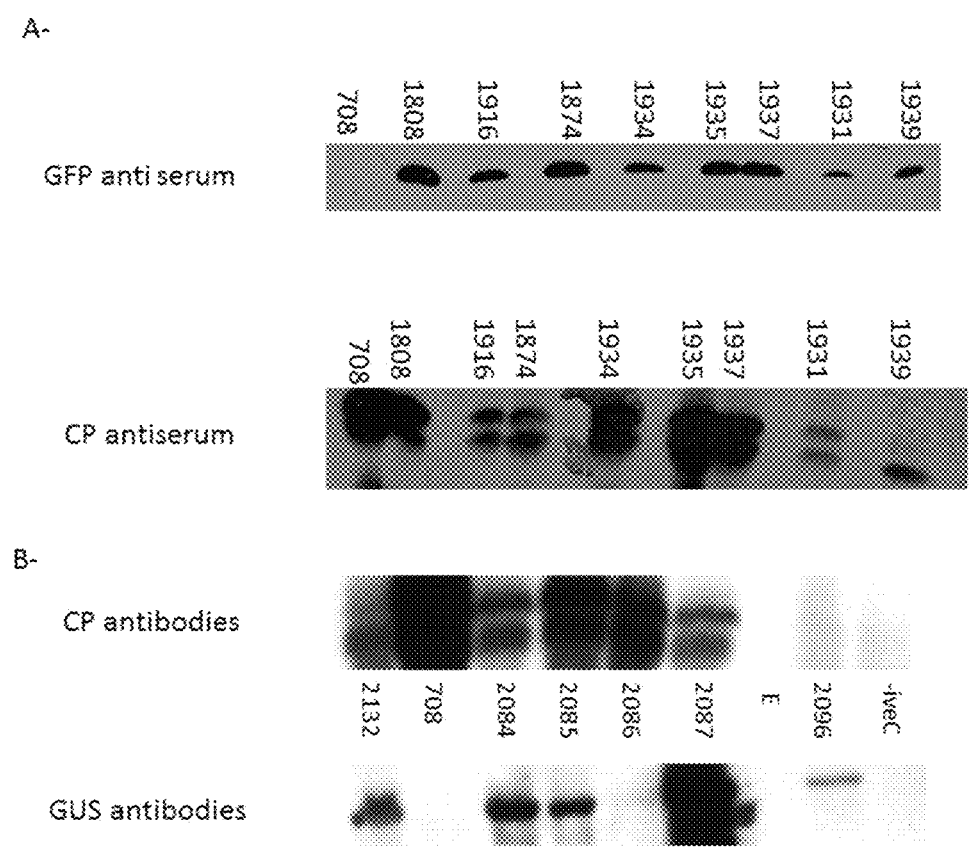

FIG. 19 Western blot analysis of the different constructs in citrus to evaluate the expression of GFP and GUS. (A) GFP and CP antibody used to determine the level of expression of GFP relative to CP in citrus 708 plant infected with Δp33CTV9R (Tatineni et al., 2008), 1808 plant infected with BCN5 (Folimonov et al., 2007), 1916 plant infected with CTV33-23-G-GFP-40, 1874 plant infected with CTV33-23-BY-GFP-37, 1934, 1935, 1937 infected with CTV33-13-BY-GFP-69, 1931 and 1939 infected with construct CTV33-Δ13-G-GFP-65 and CTV33-Δ13-B-GFP-66, respectively. (B) GUS and CP antibody used to determine the level of expression of GUS relative to CP in citrus 2084, 2085, 2086, 2087 plants infected with construct CTV33-Δ13-BYGUS-61, 2132 plant infected with construct CTV33-23-BYGUS-60, 2096 plant infected with expression vector CTV33-Δ13-BYGFP-NIa-GUS-78, E=empty well and buffer=–iveC.

FIG. 20 CTV based expression vector built to simultaneously express four genes from four controller elements. (A) A schematic representation of CTV9R. (B) Modification of CTV9R to create expression vector CTVΔ13-BRFP-Gb-FosC-BYbJunN-CTMVCP-118 which expresses 4 genes from different locations within the CTV genome. The first gene is the red fluorescent protein gene (tagRFP) expressed from between the minor and major coat proteins under the control of the Beet yellows virus (BYV) coat protein controller element (CP-CE), the second and third genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively replacing the p13 gene and the fourth gene is the CP of TMV expressed from behind p23 under the control of the duplicated major CP-CE of CTV.

FIG. 21 CTV based expression vector built to simultaneously express three genes from three controller elements. (A) A schematic representation of CTV9R. (B) Modification of CTV9R to create expression vector CTVΔ13-GbFosC- BYbJunN-CTMVCP-129 which expresses 3 genes from different locations within the CTV genome. The first and second genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively replacing the p13 gene and the fourth gene is the CP of TMV expressed from behind p23 under the control of the duplicated major CP-CE of CTV.

FIG. 22 CTV based expression vector built to simultaneously express three genes from three controller elements. (A) A schematic representation of CTV9R. (B) Modification of CTV9R to create expression vector CTV-BRFP-BYGFP-CTMVCP-117 which expresses 3 genes from different locations within the CTV genome. The first gene is the red fluorescent protein gene (tagRFP) expressed from between the minor and major coat proteins under the control of the Beet yellows virus (BYV) coat protein controller element (CP-CE), the second gene is the Green fluorescent protein (GFPC3) under the control of Beet yellow stunt virus (BYSV) CP-CE inserted between p13-p20 gene and the third gene is the CP of TMV expressed from behind p23 under the control of the duplicated major CP-CE of CTV.

FIG. 23 CTV based expression vector built to simultaneously express three genes from three controller elements. (A) A schematic representation of CTV9R. (B) Modification of CTV9R to create expression vector CTV-BASL-BYPTA-CP7-119 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an agglutinin from Pinellia ternata (PTA) under the control of Beet yellow stunt virus (BYSV) CP-CE inserted between p13-p20 gene and the third gene is an antimicrobial peptide from Tachypleus tridentatus (P7) expressed from behind p23 under the control of the duplicated major CP-CE of CTV.

FIG. 24 CTV based expression vector built to simultaneously express three genes from three controller elements. (A) A schematic representation of CTV9R. (B) Modification of CTV9R to create expression vector CTV-BASL-BYPTA-CP10-120 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an agglutinin from Pinellia ternata (PTA) under the control of Beet yellow stunt virus (BYSV) CP-CE inserted between p13-p20 gene and the third gene is an antimicrobial peptide from Sus scorfa (P10) expressed from behind p23 under the control of the duplicated major CP-CE of CTV.

FIG. 25 CTV based expression vector built to simultaneously express three genes from three controller elements. (A) A schematic representation of CTV9R. (B) Modification of CTV9R to create expression vector CTV-BASL-BYP10-CP7-131 which expresses 3 genes from different locations within the CTV genome. The first gene is a lectin from Allium sativum (ASL) expressed from between the minor and major coat proteins under the control of the Beet yellows virus (BYV) coat protein controller element (CP-CE), the second gene is an antimicrobial peptide from Sus scorfa (P10) under the control of Beet yellow stunt virus (BYSV) CP-CE inserted between p13-p20 gene and the third gene is a second antimicrobial peptide from Tachypleus tridentatus (P7) expressed from behind p23 under the control of the duplicated major CP-CE of CTV.

FIG. 26 CTV based expression vector built to simultaneously express three genes from three controller elements. (A) A schematic representation of CTV9RΔp33. (B) Modification of CTV9RΔp33 to create expression vector CTV33-BGFP-BYGUS-GTMVCP-79 which expresses 3 genes from different locations within the CTV genome. The first gene is a green fluorescent protein expressed from between the minor and major coat proteins under the control of the Beet yellows virus (BYV) coat protein controller element (CP-CE), the second gene is a β-Glucuronidase (GUS) gene from Eisherchia coli under the control of Beet yellow stunt virus (BYSV) CP-CE inserted between p13-p20 gene and the third gene is the CP of TMV expressed from behind p23 under the control of Grape vine leaf roll associated virus-2 (GLRaV-2) CP-CE.

FIG. 27 CTV based expression vector built to simultaneously express four genes from four controller elements. (A) A schematic representation of CTV9RΔp33. (B) Modification of CTV9RΔp33 to create expression vector CTV33-BGFP-GbFosC-BYbJunN-81 which expresses 3 genes from different locations within the CTV genome. The first gene is the green fluorescent protein gene (GFPC3) expressed from between the minor and major coat proteins under the control of the Beet yellows virus (BYV) coat protein controller element (CP-CE), the second and third genes are the truncated mammalian transcription factors bFos and bJun fused to the C and N terminus of EYFP (Hu et al., 2002) under the control of Grape vine leaf roll associated virus-2 (GLRaV-2) and Beet yellow stunt virus (BYSV) CP-CE respectively. The bFosC gene is inserted behind p23 gene.

FIG. 28 CTV based expression vector built to simultaneously express four genes from four controller elements. (A) A schematic representation of CTV9RΔp33. (B) Modification of CTV9RΔp33 to create expression vector CTV33-Δ13-BGFP-BYbJunN-GbFosC-82 which expresses 3 genes from different locations within the CTV genome. The first gene is the green fluorescent protein gene (GFPC3) expressed from between the minor and major coat proteins under the control of the Beet yellows virus (BYV) coat protein controller element (CP-CE), the second gene is the truncated mammalian transcription factor bJun to the N terminus of EYFP (bJunN) (Hu et al., 2002) under the control of Beet yellow stunt virus (BYSV) CP-Cereplacing the p13 gene of CTV and the third gene is the truncated mammalian transcription factor bFos fused to the C-terminus of EYFP (bFosC) under the control of Grape vine leaf roll associated virus-2 (GLRaV-2) CP-CE inserted behind p23.

FIG. 29 Negative staining Electron microscopy pictures from leaf dips of infiltrated N. benthamiana Leaves. (A) Leaf dips from infiltrated N. benthamiana leaves with construct CTV33-BGFP-BYGUS-GTMVCP-79 reveals the formation of CTV vector virions and TMV pseudo virions indicating the expression of the TMV coat protein gene. (B) Leaf dip from Infiltrated N. benthamiana leaves with construct CTV33-Δ13-BGFP-BYbJunN-GbFosC-82 reveals the formation of virions.

Figure 30:
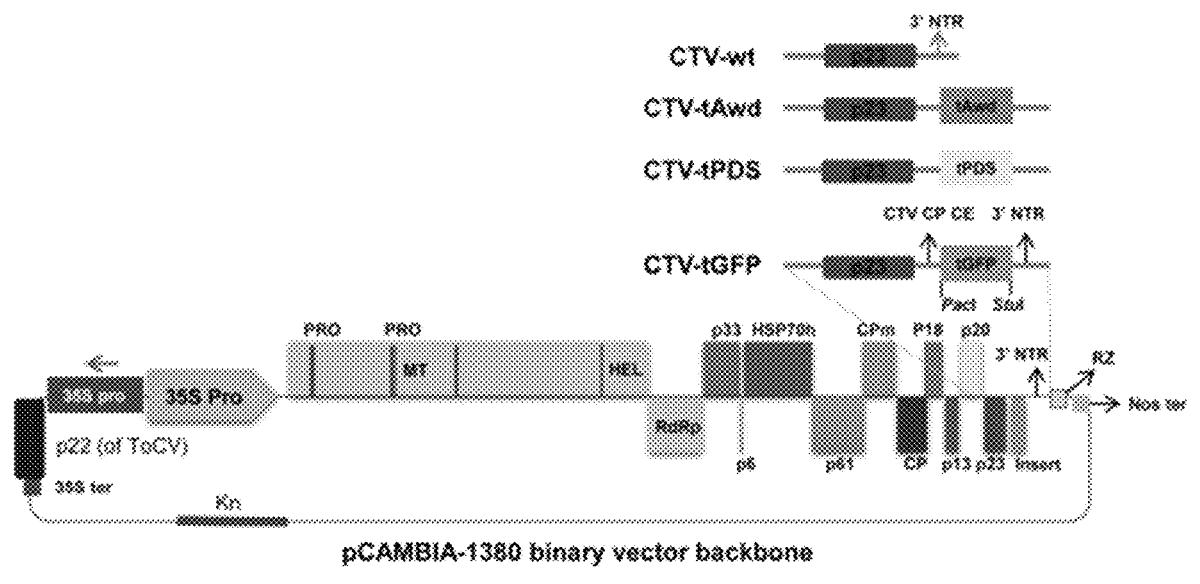

FIG. 30 Schematic representation of Citrus tristeza virus (CTV) genome in a binary vector. Schematic representation of full-length infectious cDNA clones of Citrus tristeza virus (CTV) with its open reading frames (ORF) placed between enhanced 35S promoter of Cauliflower mosaic virus at the 5' end, ribozyme (RZ) of Subterranean clover mottle virus satellite RNA and nopaline synthase terminator (Nos ter) at the 3' end in the binary vector pCAMBIA-1380. The vector plasmid referred to as wild type CTV (CTV-wt) is based on CTV isolate T36. Unique restriction sites, PacI and StuI at 5' and 3' end, respectively, to ligate the inserts under coat protein (CP) sub-genomic RNA controller element (CE) between ORF-p23 and 3'-nontranslated region (NTR). Truncated green fluorescent protein (tGFP) was cloned using unique restriction sites PacI and StuI to generate CTV-tGFP, similarly, truncated phytoene desaturase (tPDS) and truncated abnormal wing disc (tAwd) were cloned to generate CTV-tPDS and CTV-tAwd respectively. ORF p22 silencing suppressor from Tomato chlorosis Crinivirus (ToCV) driven by 35S promoter & 35s terminator (35S ter). PRO, papain-like proteases; MT, methyltransferase-like domain; HEL, helicase-like domain; RdRp, RNA-dependent RNA polymerase domain; and the ten 3'-end ORFs p33, p6, HSP70h, p61, CPm, CP, p18, p13, p20, and p23.

Figure 31:
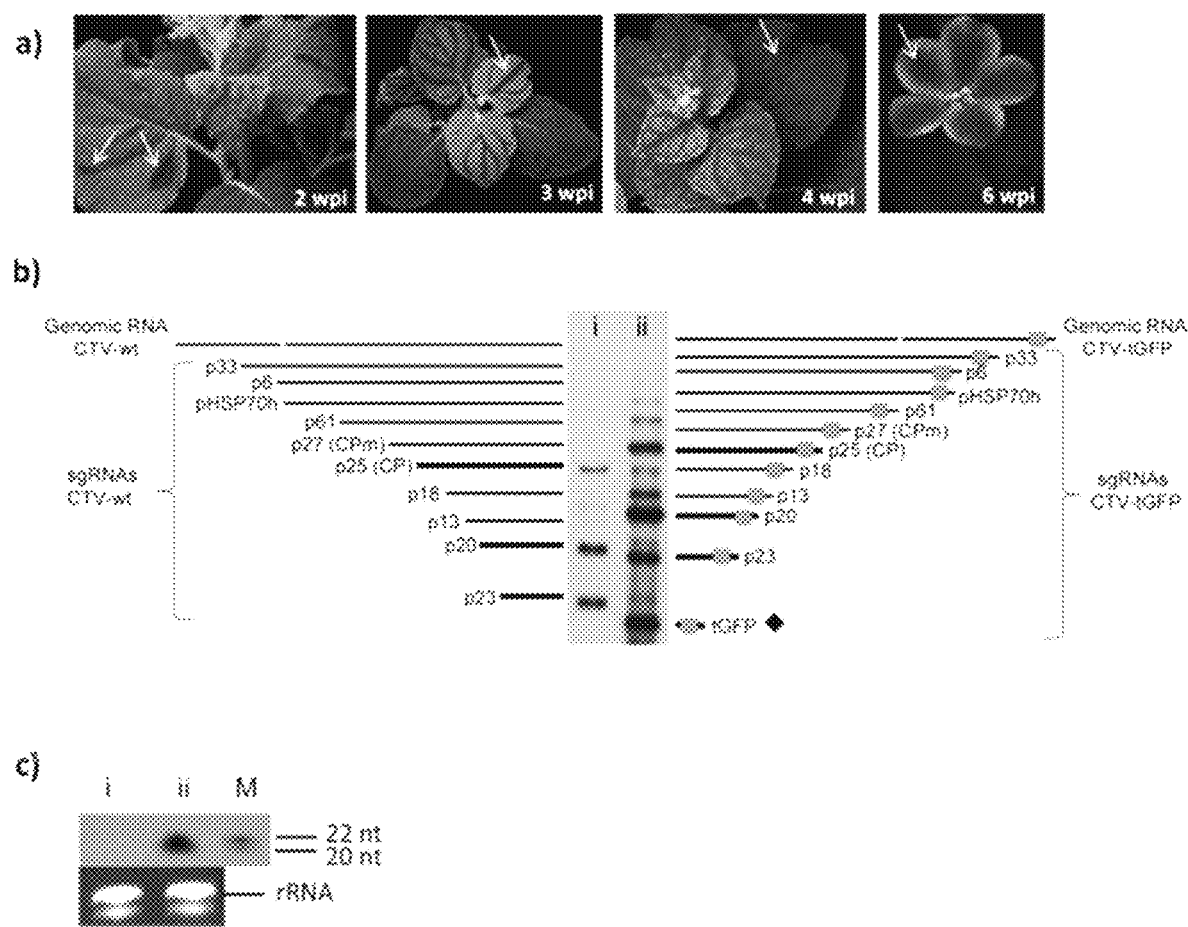

FIG. 31. Citrus tristeza virus (CTV)-induced gene silencing in *Nicotiana benthamiana* transgenic line 16c. Transgene green fluorescent protein (GFP) of *Nicotiana benthamiana* line 16c was silenced by Citrus tristeza virus (CTV)-based virus-induced gene silencing vector carrying truncated GFP (tGFP). (a) Progression of GFP silencing in the systemic leaves, stems and flowers at 2, 3, 4 and 6 weeks post infiltration (wpi) was photographed under handheld long wave fluorescent UV lamp. GFP Silenced areas appear as red, indicated by arrow mark, due to autofluorescence of chlorophyll. (b) Schematic representation of the subgenomic RNA (sgRNA) profile of CTV from plants infected with wild type CTV (CTV-wt) control (left), and CTV-tGFP (right). Abundantly accumulating sgRNAs for p23, p20 and CP are shown in thick lines. Northern blot shows the 3' sgRNAs and the extra sgRNA for tGFP, indicated by a diamond symbol, accumulated in CTV-tGFP plants (ii; on right) compared to CTV-wt plants (i; on left). The blot was hybridized with digoxigenin labeled minus-sense ribo-probe specific to the 3'-nontranslated region of CTV. (c) Accumulation of GFP-specific small interfering RNAs (siRNAs) in CTV-tGFP plants (ii) compared to CTV-wt (i). Ethidium bromide stained rRNA in polyacrylamide gel electrophoresis as a loading control is shown at the bottom. Synthetic 5'-DIG-tabled oligonucleotide of 18 and 21 mer, which ran as 20 and 22 nucleotides, respectively, were used as siRNA size markers (M). The blot was hybridized with digoxigenin labeled minus-sense ribo-probe specific to full-length sequence of GFP gene.

Figure 32:
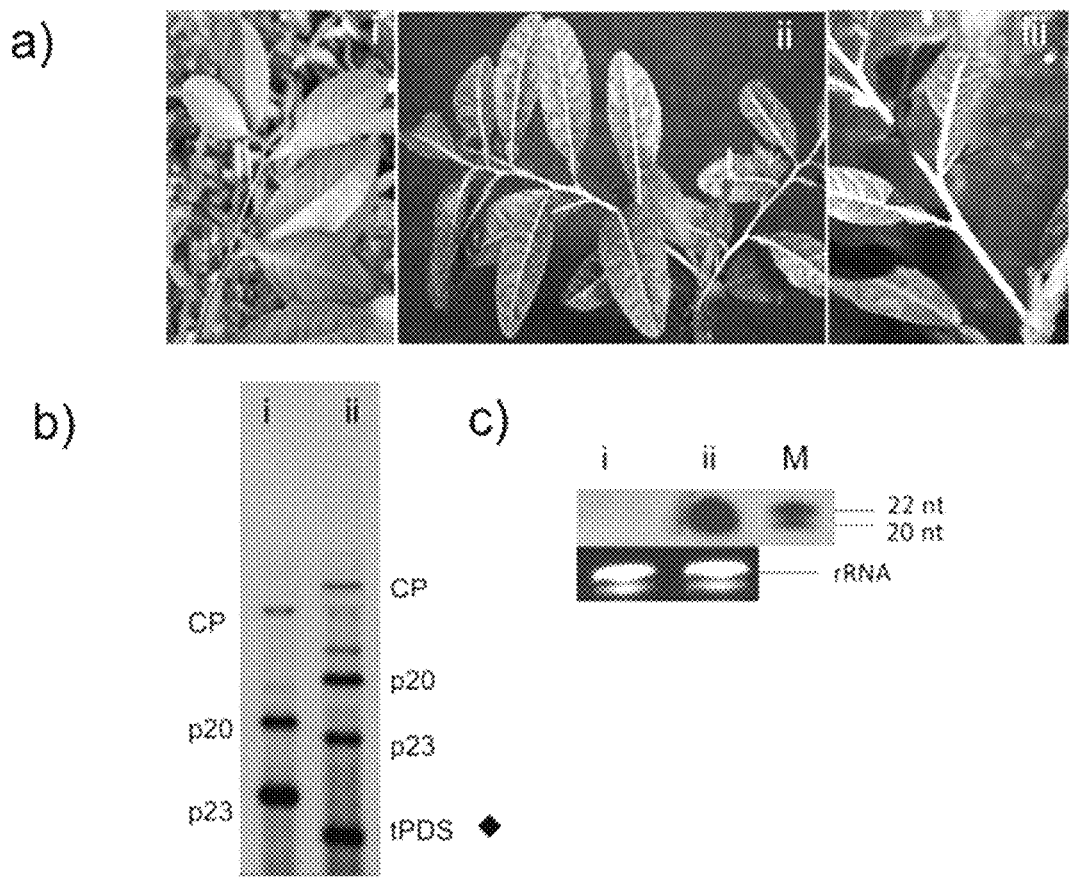

FIG. 32 Citrus tristeza virus (CTV)-induced gene silencing in citrus. *Citrus macrophylla* endogenous gene, phytoene desaturase (PDS) was silenced by CTV-based virus-induced gene silencing (VIGS) vector carrying truncated PDS (tPDS). (a) Photo-bleaching phenotype observed in the newly emerging leaves, stem and thorns, indicated by arrow marks (ii and iii), of *C. macrophylla* infected with CTV-tPDS compared to control wild type CTV (CTV-wt) (i). (b) Northern blot shows the 3' subgenomic RNAs (sgRNAs) and the extra sgRNA for tPDS, indicated by a diamond symbol, accumulated in CTV-tPDS plants (ii; on right) compared to CTV-wt plants (i; on left). The blot was hybridized with digoxigenin labeled minus-sense ribo-probe specific to the 3' nontranslated region of CTV. (c) Accumulation of PDS-specific small interfering RNAs (siRNAs) in CTV-tPDS plants (ii) compared to CTV-wt (i). Ethidium bromide stained rRNA in polyacrylamide gel electrophoresis as a loading control is shown at the bottom. Synthetic 5'-DIG-labeled oligonucleotide of 18 and 21 mer, which ran as 20 and 22 nucleotides respectively, were used as siRNA size markers (M). The blot was hybridized with digoxigenin labeled minus-sense ribo-probe specific to full-length sequence of PDS gene.

Figure 33:
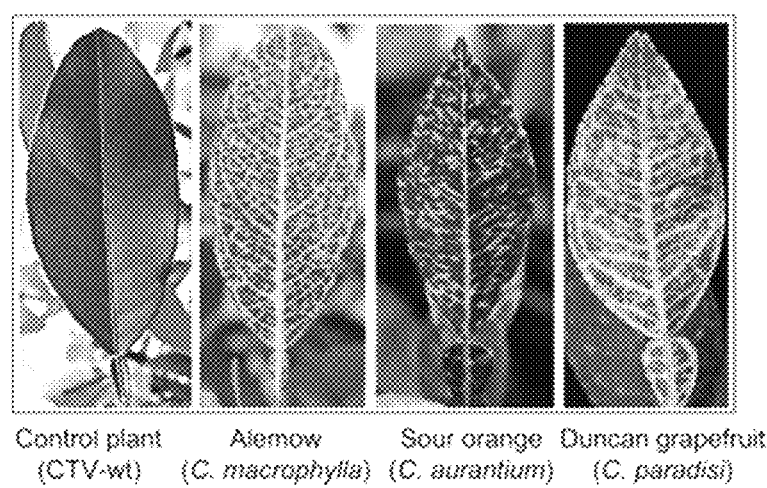

FIG. 33 Graft-transmissibility of Citrus tristeza virus (CTV)-based virus-induced gene silencing (VIGS) vector and photo-bleaching phenotype to other citrus cultivars. Source plant, *Citrus macrophylla*, harboring CTV-VIGS vector expressing truncated phytoene desaturase gene of *C. macrophylla* and inducing photo-bleaching phenotype. *C. macrophylla* source plant used for side and leaf graft inoculations to Duncan grapefruit (*C. paradisi*) and Sour orange (*C. aurantium*), which induced typical photo-bleaching phenotype in the newly emerged systemic leaves.

Figure 34:
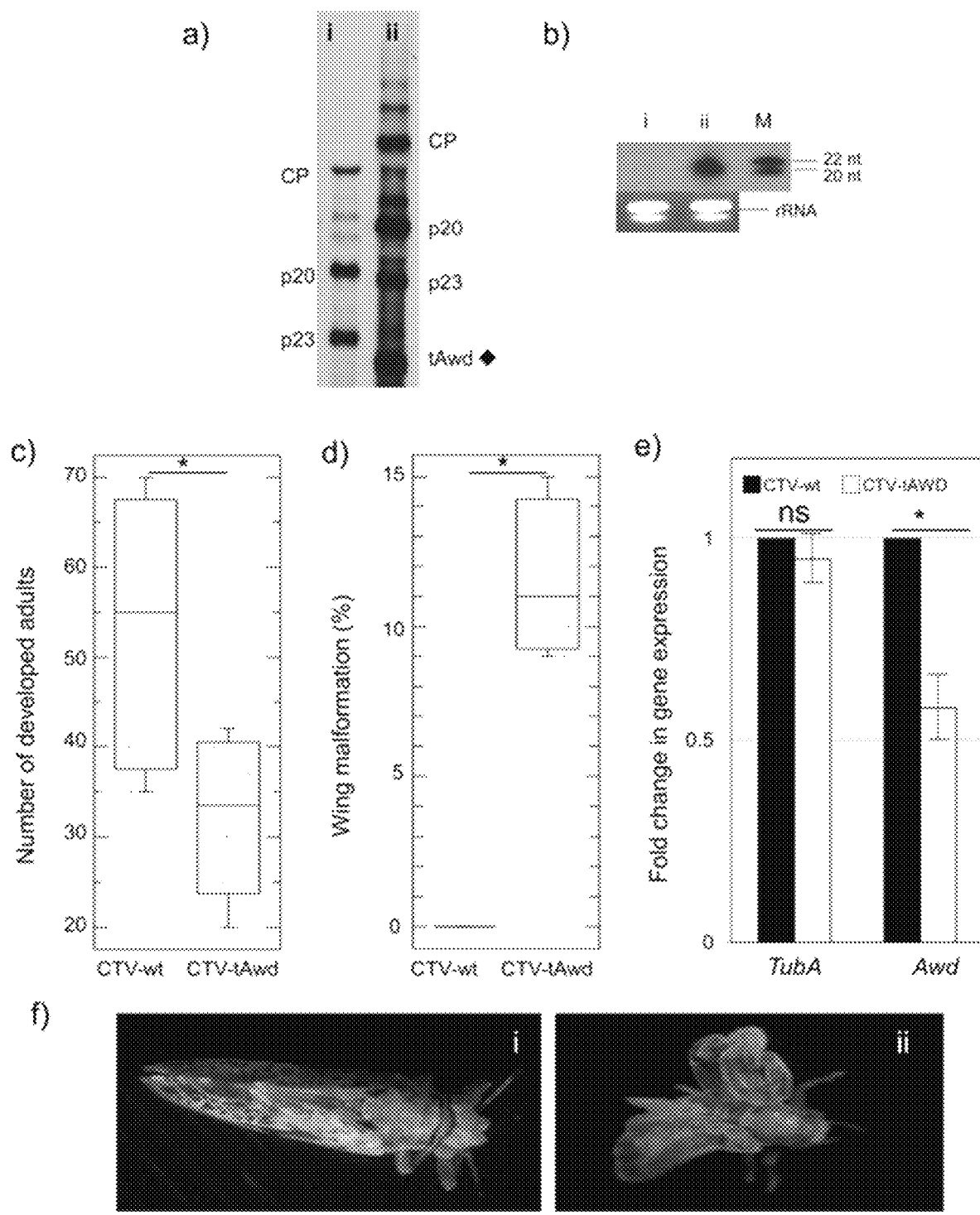

FIG. 34. Citrus tristeza virus (CTV)-based plant-mediated RNAi in phloem-sap sucking insect *Diaphorina citri*. (a) Northern blot analysis of total RNA from systemic leaves of *Citrus macrophylla* plants infected with wild type CTV (CTV-wt) control (i) and truncated abnormal wing disc gene (tAwd) expressing CTV vector (CTV-tAwd) (ii). Accumulation of an additional subgenomic RNA (sgRNA), tAwd, in plants infected with CTV-tAwd is indicated by a diamond symbol. The blot was hybridized with digoxigenin labeled minus-sense ribo-probe specific to the 3' nontranslated region of CTV. (b) Accumulation of Awd-specific small interfering RNAs (siRNAs) in CTV-tAwd plants (ii) in comparison to CTV-wt (i). Ethidium bromide stained rRNA in polyacrylamide gel electrophoresis as loading control is shown at the bottom. Synthetic 5'-DIG-labeled oligonucleotide of 18 and 21 mer, which ran as 20 and 22 nucleotides respectively, were used as siRNA size markers (M). The blot was hybridized with digoxigenin labeled minus-sense ribo-probe specific to full-length sequence of abnormal wing disc (Awd) gene. (c) Box plot shows the number of *Diaphorina citri* adults developed from nymphs fed on CTV-wt and CTV-tAwd plants after one month exposure. (d) Percentage of wing-malformed adults on CTV-wt and CTV-tAwd plants, (e) expression of Awd in *D. citri* adults exposed to CTV-wt and CTV-tAwd plants. Alpha-tubulin (TubA) and actin (Act) were used as a non-target gene and an internal control gene, respectively. The level of Awd transcripts in *D. citri* adults exposed to CTV-wt plants was arbitrarily set to the value one and the level of Awd transcripts in CTV-tAwd were presented as relative value to this reference value. Means and standard deviation (as bars) of experiments in triplicate are presented. Asterisks indicate statistically significant difference ($p<0.05$) and 'ns' as non-significant. (f) Images of *D. citri* adults developed from nymphs after exposure to CTV-wt (i) CTV-tAwd (ii) plants.

DETAILED DESCRIPTION

The early development of viral vectors was aimed at the inexpensive production of high levels of specialty proteins that could be scaled up in the field. The first attempt at a plant viral vector utilized Cauliflower mosaic virus, a dsDNA virus (Brisson et al., 1984; Gronenborn et al., 1981). However, this vector was too unstable to be useful (Fütterer et al., 1990). The development of reverse genetics systems amenable for manipulation of RNA viruses made many more viruses candidates for vector development (Ahlquist et al., 1984). There was considerable controversy concerning the value of RNA viruses for vectors (Siegel, 1983, 1985; Van Vluten-Dotting, 1983 Van Vluten-Dotting et al., 1985). It was argued that the lack of proof-reading of the RNA virus replicases would result in too rapid sequence drift to maintain foreign sequences during replication. However, subsequent development and use of RNA virus-based vectors demonstrated that this concern was overstated.

Ongoing efforts have been underway to create virus-based vectors for citrus trees based on Citrus tristeza virus (CTV). CTV has the largest reported RNA of a plant virus of approximately 20 kb (Karasev et al., 1995; Pappu et al., 1994). It has two conserved gene blocks associated with replication and virion formation (Karasev, 2000). The replication gene block occupies the 5' half of the genome. Its proteins are expressed from the genomic RNA via a poly protein strategy with a +1 ribosomal frame shift to occasionally express the RNA dependent RNA polymerase (Karasev et al., 1995). The filamentous virions of CTV are encapsidated by two coat proteins, with the major coat protein (CP) encapsidating about 97% of the virion and the 5' ~700 nts encapsidated by the minor coat protein (CPm) (Satyanarayana et al., 2004). Virion formation is a complex process requiring two proteins (Hsp70h and p61) in addition to the coat proteins (Satyanarayana et al., 2000, 2004; Tatineni et al., 2010). These four genes as well as the 6 remaining genes are differentially expressed via a nested set of 3' co-terminal sub genomic (sg) RNAs (Hilf et al., 1995). Upstream of each ORF there is a controller element (CE) that determines the transcription level (Gowda et al., 2001). Levels of transcription are also associated with the +1 transcription start site (Ayllón et al., 2003), the presence of a non-translated region upstream of the ORF (Gowda et al., 2001), and the closeness of the ORF to the 3' terminus (Satyanarayana et al., 1999).

The first generations of CTV vector examined three different strategies that were fusion of the CP gene, insertion of an extra gene, and replacement of the p13 ORF (Folimonov et al., 2007). Replacement of the p13 ORF and fusion to the coat protein ORF did not result in effective vectors, but the addition of an extra gene resulted in viable vectors that produce relative large amounts of foreign gene and were stable in citrus trees for years. However, the first efforts in designing vectors based on CTV examined only a few of the many possibilities for expressing foreign genes in this large virus. In this work, the inventors attempted to examine the limitations of CTV to be manipulated into a vector. The inventors examined whether the virus allowed insertions in different positions within the genome and which resulted in maximal expression with different sizes of inserts. The inventors also examined whether different fusion strategies with different viral genes are viable and whether multiple foreign genes can be expressed. The CTV constructs disclosed herein are amazingly tolerant to manipulation at several positions within the genome giving a multitude of different vector strategies that are viable.

Once citrus is infected with a CTV vector containing a foreign gene, it is easy to move the vector to other citrus trees by grafting. However, a limitation of the CTV vector system is the difficulty of initially getting citrus infected with new vector constructs. Directly inoculating citrus from the cDNA clones, either by agro-inoculation, particle bombardment, or mechanical inoculation with RNA transcripts is extremely difficult and unpredictable (Gowda et al., 2005; Satyanarayana et al., 2001). An alternative has been to inoculate with virions purified from Nicotiana benthamiana protoplasts (Folimonov et al., 2007; Robertson et al., 2005; Satyanarayana et al., 2001; Tatineni et al., 2008). However, infection of only approximately 0.01-0.1% of protoplasts with in vitro transcribed RNA has been achieved (Satyanarayana et al., 2001). Yet, since virions are much more infectious to the protoplasts than RNA (Navas-Castillo et al., 1997), the inventors were able to amplify the infection by sequential passage in protoplasts (Folimonov et al., 2007; Robertson et al., 2005; Satyanarayana et al., 2001; Tatineni et al., 2008). Although workable, this is an extremely difficult system. The inventors are now able to agro-inoculate N. benthamiana plants that result in systemic infection. This result allows analysis of the vector constructs more quickly in these plants and provides copious amounts of recombinant virus for inoculation of citrus. Thus, the inventors report the activity of the different vector constructs in N. benthamiana and Citrus.

According to one embodiment, the invention pertains to a CTV viral vector engineered to comprise a gene cassette comprising a heterologous nucleic acid. The gene cassette is located at a targeted position on the CTV genome. In a more specific embodiment, the CTV viral vector is engineered such that the gene cassette is positioned at CTV genome regions p13-p20, p20-p23 or p23-3'NTR. In other embodiments, the CTV viral vector is engineered to include multiple genes at one or multiple positions. It is shown herein that CTV viral vectors can successfully be engineered to include up to 3 or at least 4 genes that are expressible by the vector, while maintaining the proper function and infectivity of the vector.

In related embodiments, the invention pertains to a plant that includes at least one cell transfected with the CTV viral vector engineered to comprise a gene cassette comprising a heterologous nucleic acid, the CTV viral vector engineered such that one or more gene cassettes are positioned at CTV genome regions p13-p20, p20-p23 or p23-3'NTR. Other related embodiments pertain to methods of expressing at least one heterologous nucleic acid or polypeptide in a plant by infecting the plant with the specified vector.

In a further embodiment, the invention is directed to a CTV viral vector engineered to comprise at least one gene cassette that includes a heterologous nucleic acid, wherein the CTV viral vector engineered such that the gene cassette is inserted in place of the CTV p13 gene. In related embodiments, the invention pertains to a plant that includes at least one cell transfected with the CTV viral vector or to methods of expressing the heterologous nucleic acid or polypeptide in a plant by infecting the plant with the specified vector.

In another embodiment, the invention relates to a CTV viral vector engineered to comprise at least one gene cassette comprising a polynucleotide encoding heterologous polypeptide and IRES sequence conjugated thereto. In related embodiments, the invention pertains to a plant that includes at least one cell transfected with the CTV viral vector or to methods of expressing the heterologous polypeptide in a plant by infecting the plant with the specified vector.

In further embodiments, the invention relates to a CTV viral vector engineered to comprise a gene cassette comprising a polynucleotide sequence with continuous amino acid codons extending from the p23 ORF encoding a first heterologous polypeptide (protease) with cleavage sites on each side plus a second heterologous polypeptide. In related embodiments, the invention pertains to a plant that includes at least one cell transfected with the CTV viral vector or to methods of expressing the heterologous polypeptide in a plant by infecting the plant with the specified vector.

In further embodiments, the polynucleotide further comprises a sequence encoding a first control element upstream of said first heterologous polypeptide, a second sequence encoding a protease with cleavage sites engineered on each side, and a sequence encoding a second heterologous polypeptide.

According to another embodiment, the invention is directed to CTV viral vector engineered to comprise a first gene cassette comprising a polynucleotide sequence encoding a first heterologous nucleic acid and a first controller element upstream of said first heterologous nucleic acid encoding sequence; and a second gene cassette comprising a polynucleotide sequence encoding a second heterologous nucleic acid and a second control element upstream of said second heterologous nucleic acid encoding sequence. Optionally, the CTV viral vector further comprises a third gene cassette comprising a polynucleotide sequence encoding a third heterologous nucleic acid and a third controller element upstream of said third heterologous nucleic acid encoding sequence; and a fourth gene cassette comprising a polynucleotide sequence encoding a fourth heterologous nucleic acid and a fourth controller element upstream of said fourth heterologous nucleic acid encoding sequence. Those skilled in the art will appreciate that additional gene cassettes can be added to the vector so long as function and infectivity of the vector is maintained. In related embodiments, the invention pertains to a plant that includes at least one cell transfected with the CTV viral vector or to methods of expressing the heterologous nucleic acid in a plant by infecting the plant with the specified vector.

Examples of controller elements (CE) useful in accordance with the teachings herein include but are not limited to controller elements homologous to CTV or heterologous control elements. Heterologous controller elements include, but are not limited to, coat protein controller elements (CP-CEs) of three closteroviruses: Beet yellows virus (BYV) (94 nts from 13547-13640 Genbank accession # AF190581) (Peremyslov et al., 1999), Beet yellow stunt virus (BYSV) (101 nts from 8516-8616 Genbank accession # U51931)(Karasev et al., 1996) and Grape vine leaf roll associated virus-2 (GLRaV-2) (198 nts from 9454-9651 Genbank accession # DQ286725). It will be evident to those skilled in the art, in view of the teachings herein, that other controller elements may be implemented, and in particular control elements having strong promoter like activity.

Silencing of Target Genes

Heterologous nucleic acid used to transfect plants may include nucleic acids that interact with a target nucleic acid. Namely, the heterologous polynucleotide encodes a molecule able to modulate expression, RNA processing, translation or activity of a target nucleic acid. The encoded molecule may be a RNA interfering molecule, antibody, antisense molecule, PMO, ribozyme or small molecule.

RNA interference (RNAi) is a process by which double-stranded RNA (dsRNA) is used to silence gene expression. While not wanting to be bound by theory, RNAi begins with the cleavage of longer dsRNAs into small interfering RNAs (siRNAs) by an RNaselll-like enzyme, dicer. SiRNAs are dsRNAs that are usually about 19 to 28 nucleotides, or 20 to 25 nucleotides, or 21 to 22 nucleotides in length and often contain 2-nucleotide 3' overhangs, and 5' phosphate and 3' hydroxyl termini One strand of the siRNA is incorporated into a ribonucleoprotein complex known as the RNA-induced silencing complex (RISC). RISC uses this siRNA strand to identify mRNA molecules that are at least partially complementary to the incorporated siRNA strand, and then cleaves these target mRNAs or inhibits their translation. Therefore, the siRNA strand that is incorporated into RISC is known as the guide strand or the antisense strand. The other siRNA strand, known as the passenger strand or the sense strand, is eliminated from the siRNA and is at least partially homologous to the target mRNA. Those of skill in the art will recognize that, in principle, either strand of an siRNA can be incorporated into RISC and function as a guide strand. However, siRNA design (e.g., decreased siRNA duplex stability at the 5' end of the desired guide strand) can favor incorporation of the desired guide strand into RISC.

The antisense strand of an siRNA is the active guiding agent of the siRNA in that the antisense strand is incorporated into RISC, thus allowing RISC to identify target mRNAs with at least partial complementarity to the antisense siRNA strand for cleavage or translational repression. RISC-related cleavage of mRNAs having a sequence at least partially complementary to the guide strand leads to a decrease in the steady state level of that mRNA and of the corresponding protein encoded by this mRNA. Alternatively, RISC can also decrease expression of the corresponding protein via translational repression without cleavage of the target mRNA.

The term "siRNA" as used herein refers to a double-stranded interfering RNA unless otherwise noted. Typically, an siRNA of the invention is a double-stranded nucleic acid molecule comprising two nucleotide strands, each strand having about 19 to about 28 nucleotides (i.e. about 19, 20, 21, 22, 23, 24, 25, 26, 27, or 28 nucleotides). The phrase "interfering RNA having a length of 19 to 49 nucleotides" when referring to a double-stranded interfering RNA means that the antisense and sense strands independently have a length of about 19 to about 49 nucleotides, including interfering RNA molecules where the sense and antisense strands are connected by a linker molecule.

In addition to siRNA molecules, other interfering RNA molecules and RNA-like molecules can interact with RISC and silence gene expression. Examples of other interfering RNA molecules that can interact with RISC include short hairpin RNAs (shRNAs), single-stranded siRNAs, microRNAs (miRNAs), and dicer-substrate 27-mer duplexes. Examples of RNA-like molecules that can interact with RISC include siRNA, single-stranded siRNA, microRNA, and shRNA molecules containing one or more chemically modified nucleotides, one or more non-nucleotides, one or more deoxyribonucleotides, and/or one or more non-phosphodiester linkages. All RNA or RNA-like molecules that can interact with RISC and participate in RISC-related changes in gene expression are referred to herein as "interfering RNAs" or "interfering RNA molecules." SiRNAs, single-stranded siRNAs, shRNAs, miRNAs, and dicer-substrate 27-mer duplexes are, therefore, subsets of "interfering RNAs" or "interfering RNA molecules."

During replication of CTV, large amounts of double stranded RNA intermediates are produced of the genomic and subgenomic RNAs that are processed into small interfering RNA molecules. The subgenomic RNAs are 3'-co-terminal, so the more 3' sequences are produced multiple times in the longer subgenomic RNAs. Sequences designed to target specific sequences in the plant, pathogen, or pest do not need an extra subgenomic mRNA controller element. Multiple target sequences can be fused together as one larger heterologous sequence.

Single-stranded interfering RNA has been found to effect mRNA silencing, albeit less efficiently than double-stranded RNA. Therefore, embodiments of the present invention also provide for administration of a single-stranded interfering RNA that has a region of at least near-perfect contiguous complementarity with a portion of the target nucleic acid. The single-stranded interfering RNA has a length of about 19 to about 49 nucleotides as for the double-stranded interfering RNA cited above. The single-stranded interfering RNA has a 5' phosphate or is phosphorylated in situ or in vivo at the 5' position. The term "5' phosphorylated" is used to describe, for example, polynucleotides or oligonucleotides having a phosphate group attached via ester linkage to the C5 hydroxyl of the sugar (e.g., ribose, deoxyribose, or an analog of same) at the 5' end of the polynucleotide or oligonucleotide.

Single-stranded interfering RNAs can be synthesized chemically or by in vitro transcription or expressed endogenously from vectors or expression cassettes as described herein in reference to double-stranded interfering RNAs. 5' Phosphate groups may be added via a kinase, or a 5' phosphate may be the result of nuclease cleavage of an RNA. A hairpin interfering RNA is a single molecule (e.g., a single oligonucleotide chain) that comprises both the sense and antisense strands of an interfering RNA in a stem-loop or hairpin structure (e.g., a shRNA). For example, shRNAs can be expressed from DNA vectors in which the DNA oligonucleotides encoding a sense interfering RNA strand are linked to the DNA oligonucleotides encoding the reverse complementary antisense interfering RNA strand by a short spacer. If needed for the chosen expression vector, 3' terminal T's and nucleotides forming restriction sites may be added. The resulting RNA transcript folds back onto itself to form a stem-loop structure.

Nucleic acid sequences cited herein are written in a 5' to 3' direction unless indicated otherwise. The term "nucleic acid," as used herein, refers to either DNA or RNA or a modified form thereof comprising the purine or pyrimidine bases present in DNA (adenine "A," cytosine "C," guanine "G," thymine "T") or in RNA (adenine "A," cytosine "C," guanine "G," uracil "U"). Interfering RNAs provided herein may comprise "T" bases, particularly at 3' ends, even though "T" bases do not naturally occur in RNA. "Nucleic acid" includes the terms "oligonucleotide" and "polynucleotide" and can refer to a single-stranded molecule or a double-stranded molecule. A double-stranded molecule is formed by Watson-Crick base pairing between A and T bases, C and G bases, and between A and U bases. The strands of a double-stranded molecule may have partial, substantial or full complementarity to each other and will form a duplex hybrid, the strength of bonding of which is dependent upon the nature and degree of complementarity of the sequence of bases.

In certain embodiments, interfering RNA target sequences (e.g., si RNA target sequences) within a target mRNA sequence are selected using available design tools. Interfering RNAs corresponding to a target sequence are then tested in vitro by transfection of cells expressing the target mRNA followed by assessment of knockdown as described herein. The interfering RNAs can be further evaluated in vivo using animal models as described herein.

Techniques for selecting target sequences for si RNAs are provided, for example, by Tuschl, T. et al., "The siRNA User Guide," revised May 6, 2004, available on the Rockefeller University web site; by Technical Bulletin #506, "siRNA Design Guidelines," Ambion Inc. at Ambion's web site; and by other web-based design tools at, for example, the Invitrogen, Dharmacon, Integrated DNA Technologies, Genscript, or Proligo web sites. Initial search parameters can include G/C contents between 35% and 55% and siRNA lengths between 19 and 27 nucleotides. The target sequence may be located in the coding region or in the 5' or 3' untranslated regions of the mRNA. The target sequences can be used to derive interfering RNA molecules, such as those described herein.

Many of the embodiments of the subject invention make reference to particular methods of inhibiting or disruption of genetic expression. Based on the teachings herein, methods of inhibiting expression include but are not limited to siRNA; ribozyme(s); antibody(ies); antisense/oligonucleotide(s); morpholino oligomers; microRNA; or shRNA that target expression of the target nucleic acid. The subject invention is not to be limited to any of the particular related methods described. One such method includes siRNA (small interfering/short interfering/silencing RNA). SiRNA most often is involved in the RNA interference pathway where it interferes with the expression of a specific nucleic acid. In addition to its role in the RNA interference pathway, siRNA also act in RNA interference-related pathways, e.g., as an antiviral mechanism or in shaping the chromatin structure of a genome.

Another method by which to inhibit expression and to inhibit the expression of the target nucleic acid in particular is shRNA. ShRNA (short hairpin or small hairpin RNA) refers to a sequence of RNA that makes a tight hairpin turn and is used to silence gene expression via RNA interference. It uses a vector introduced into cells and a U6 or H1 promoter to ensure that the shRNA is always expressed. The shRNA hairpin structure is cleaved by cellular machinery into siRNA which is then bound to the RNA-induced silencing complex. This complex binds to and cleaves mRNAs which match the siRNA that is bound to it.

Target nucleic acid can also be blocked by subjecting procured cells to an antibody specific to target nucleic acid or expression product thereof. An antisense nucleotide may also be used to block or inhibit expression, in particular, the expression of target nucleic acid. Expression may also be inhibited with the use of a morpholino oligomer or phosphorodiamidate morpholino oligomer (PMO). PMOs are an antisense technology used to block access of other molecules to specific sequences within nucleic acid. PMOs are often used as a research tool for reverse genetics, and function by knocking down gene function. This is achieved by preventing cells from making a targeted protein or by modifying splicing of pre-mRNA. One embodiment of the subject disclosure pertains to a method of treating neurons under oxidative stress by expressing an RNA interfering molecule, antisense molecule or PMO in a subject in need thereof.

In one embodiment, the target nucleic acid may be endogenous in the plant transfected with the heterologous nucleic acid. Alternatively, the heterologous nucleic acid targets a nucleic acid that relates to a plant pathogen, a biological vector (e.g. insect that spreads pathogen), or an arthropod or nematode pest. For example, the heterologous nucleic acid encodes an RNA interfering molecule specific to a target nucleic acid relating to a protein or sequence vital to the plant pathogen or biological vector. This in effect neutralizes the pathogen or biological vector. Proteins or peptides can be to add value to the plant or to prevent attack by pest and pathogens. Examples of plant value-added products include addition of vitamins or increase of flavor or stability to fruit or juice. Proteins or peptides can be to attract microbes or remove necessary microbes or to interfere with processes in pathogens or pests. RNAi targets can be the removal of any gene product in plants or prevention of protein production in pathogens or pests.

In addition to *D. citri*, almost any other insect could be a target to gene silencing. Other insect pests of citrus are aphids and whiteflies that vector viruses, mites (not an insect) that are a problem on their own, as well as vector viruses, leaf miners that damage leaves and increase susceptibility to canker, diaprepie roots weevils. Also, RNAi can be used to control nematodes.

As far as other pathogens, other viruses and fungi could be controlled by RNAi. Value added traits can be induced by RNAi that allow for silencing of undesired gene expression and gene products. For example, genes whose expression modulates flavor, color, or pathogen resistance could be targeted.

These and other embodiments are further described below and encompassed within the appended claims.

Materials and Methods for Examples 1-7 Below

Plasmids Construction pCTV9RΔp33 and pCTVΔCla 333R (Gowda et al., 2001; Satyanarayana et al., 1999, 2000, 2003; Tatineni et al., 2008) were used as base plasmids for developing all expression vectors that were used in the protoplast reverse genetics system. The numbering of the nucleotides (nts) is based on the full length T36 clone (Genbank Accession # AY170468) (Satyanarayana et al., 1999, 2003). CTVp333R-23-ITEV-GFP and CTVp333R-23-I3×ARC-GFP (FIG. 7A) were created by fusing 5' non translated region (NTR) of Tobacco etch virus (TEV) (nucleotides (nts) 2-144 Genbank accession # DQ986288) (Carrasco et al., 2007) and 3×ARC-1 (Active ribosome complementary sequence) (Akergenov et al., 2004) behind the p23 stop codon (between nts19020-19021 in full length T36 clone) using overlap extension polymerase chain reaction (PCR) (Horton et al., 1989). For creating expression vectors by gene addition and/or substitution at different locations, heterologous controller elements (CE) were selected from coat protein controller elements (CP-CEs) of three closteroviruses: Beet yellows virus (BYV) (94 nts from 13547-13640 Genbank accession # AF190581)(Peremyslov et al., 1999), Beet yellow stunt virus (BYSV) (101 nts from 8516-8616 Genbank accession # U51931)(Karasev et al., 1996) and Grape vine leaf roll associated virus-2 (GLRaV-2) (198 nts from 9454-9651 Genbank accession # DQ286725) to drive the ORFs for cycle 3 GFP (GFP) (Chalife et al., 1994; Crameri et al., 1996), β-Glucuronidase (GUS) ORF of *Eisherchia coli*, bFosYC155-238 (bFosC), bJunYN1-154 (bJunN). CTVp333R-23-BYbJunN-GbFosC, CTVp333R-23-BYbJunN, CTVp333R-23-GbFosC (FIG. 15A) were created by overlap extension PCR from plasmids pBiFC-bFosYC155 and pBiFC-bJunYN155 (Hu et al., 2002) and CTV9R (Satyanarayana et al., 1999; 2003). Since two NotI sites exist within the bimolecular fluorescence genes (BiFC), the overlap extension PCR products were digested partially by Nod restriction endonuclease. The PCR products were introduced into a StuI and Nod digested pCTVΔCla 333R (FIGS. 7A & 3-15A).

The expression vectors created in pCTV9RΔp33 were introduced into the CTV genome by digesting the plasmid with PstI (nts 17208-17213) and NotI or StuI (introduced behind 19,293 the final CTV nucleotide). Overlap extension PCR (Horton et al., 1989) was used to introduce the appropriate genes at the different locations. Replacement of the p13 gene was done by deletion of nts 17293-17581 in the p13 ORF and (CE) by overlap extension PCR (FIGS. 3-1A, 3-2A, 3-11A, 3-16A, 3-17A & 3-18A). Similarly, insertion between p13 and p20 (nts #17685-17686) (FIG. 3A), p20-p23 (nts #18312-18313) (FIG. 4A) and p23-3'NTR (nts #19020-19021) (FIGS. 3-5A, 3-6A, 3-13A, 3-16A, 3-17A & 3-18A) were done by overlap extension PCR. A hybrid gene created by fusing the GFP ORF (Chalife et al., 1994; Crameri et al., 1996) and GUS ORF separated by the HC-Pro protease motif (nts 1966-2411 Genbank accession # M11458) (Allison et al., 1985; Carrington et al., 1989) and its recognition sequence fused to the N terminus of GUS (ATGAAAACTTACAATGTTGGAGGGATG (nts 2412-2438 Genbank accession # M11458) (Allison et al., 1985; Carrington et al., 1989) (Amino acid sequence (A.A.) MKTYNVG↓GM) (arrow indicate processing site) and C terminus of GFP (ATGAAGACCTATAACGTAGGTG-GCATG) was created and inserted behind p23 (FIG. 13A) or as replacement of p13 (FIG. 3-11A) under different controller elements. A similar hybrid gene was created by using the NIa protease motif of TEV (nts 6270-6980 Genbank accession # M11458) (Allison et al., 1985) and its recognition sequence (GAGAATCTTTATTTTCAGAGT (nts 8499-8519 Genbank accession # M11458) (A.A. ENLYFQ↓S) (arrow indicate processing site) (Carrington and Dougherty, 1988) at C terminus of GFP and GAAAACCTATACTTC-CAATCG at N terminus of GUS). The redundancy of the amino acid genetic code was used to eliminate complete duplication of the nucleotide sequences of the recognition motifs. A similar strategy was used to create a hybrid gene between p23 ORF and GFP ORF in construct CTV33-23-HC-GFP-72 and CTV33-23-NIa-GFP-73 (FIG. 8). Switching the recognition motif of the proteases generated control vectors CTV33-23-HCØ-GFP-74 and CTV33-23-NIaØ-GFP-75 (FIG. 8).

The binary plasmid pCAMBIACTV9R (Gowda et al., 2005) was modified to eliminate the p33 gene by deleting nts 10858-11660 (Satyanarayana et al., 2000; Tatineni et al., 2008) and introducing a SwaI site behind the ribozyme engineered based on subterranean clover mottle virusoid (Turpen et al., 1993). PCR products amplified from the expression vectors in the pCTV9RΔp33 back-bone were introduced into the modified binary plasmid pCAMBIACTV9RΔp33 digested with PstI (Forward primer C-749) and SwaI (Reverse primer C-1894). When introducing the bimolecular fluorescence complementation (BiFC) genes into constructs CTV33-23-BYbJunN-GbFosC-59 (FIG. 17), CTV33-Δ13-BYbJunN-23-GbFosC-67 (FIG. 17), CTV33-Δ13-BYbJunN-GbFosC-76 (FIG. 16), CTV33-23-GbFosC-98 (FIG. 16) and CTV33-23-BYbJunN-97 (FIG. 16) a primer was used switching the PstI to the compatible NsiI (primer C-2085) for ease of cloning (the bFosC gene sequence contains one PstI site while the bJunN gene sequence contains two PstI sites). Preliminary screening for the right inserts in the different expression vectors was done by restriction digestion using the appropriate enzymes. The junctions where the foreign genes were introduced into the expression vectors were confirmed by sequencing at the Interdisciplinary Center for Biotechnology Research (ICBR) (University of Florida, Gainesville, Fla.). All primers are listed in Table 1-1.

TABLE 1-1

List of primers used in building expression vector

| Primer name | Sequence 5'-3'* | Description* |
|---|---|---|
| C-749 | AGT CCT CGA GAA CCA CTT AGT TGT TTA GCT ATC | 3'end of p18 (CTV T36 clones nts #17121-17145) with an added XhoI site |

TABLE 1-1-continued

List of primers used in building expression vector

| Primer name | Sequence 5'-3'* | Description* |
|---|---|---|
| | | before nt #17121) (downstream of this primer there exist within CTV genome a PstI site (nts 17208-17213 of CTV T36) used for cloning) (F.P.) |
| C-1358 | TTA TGC GGC CGC AGG CCT TGG ACC TAT GTT GGC CCC CCA TAG | 3'end of 3'NTR (nts 19,270-19,293 of CTV T36 clone) contain (StuI and NotI sites) (R.P.) |
| C-1568 | TAA TCG TAC TTG AGT TCT AAT ATG GCT AGC AAA GGA GAA GAA | 5'end of GFP (nts 1-21) with extension into 3' end of BYV CP IR (nts # 13620-13640 Genbank Accession #AF190581) (F.P.) |
| C-1894 | GCC GCA CTA GTA TTT AAA TCC CGT TTC GTC CTT TAG GGA CTC GTC AGT GTA CTG ATATAA GTA CAG ACT GGA CCT ATG TTG GCC CCC CAT AGG GAC AGT G | 3'end of 3'NTR (nts 19,262-19,293 of CTV T36 clone) with extensions that include a ribozyme of subterranean clover virusoid (underlined) (Turpen et al., 1993) and SwaI and SpeI restriction sites (R.P.) |
| C-1973 | ATG GAT GAG CTC TAC AAA TGA TTG AAGTGG ACG GAATAA GTT CC | 5'end of 3'NTR (nts 19021-19043 of CTV T36 clone) with extension into GFP 3'end (nts 700-720) (F.P.) |
| C-1974 | GGA ACT TAT TCC GTC CACTTC AAT CAT TTG TAG AGCTCA TCC AT | 3'end of GFP (nts 700-720) with extension into 5'end of 3'NTR (nts 19021-19043 of CTV T36 clone) (R.P.) |
| C-1975 | GCA CGT TGT GCT ATA GTA CGT GCC ATA ATA GTG AGT GCT AGC AAA GTATAA ACG CTG GTGTTT AGC GCA TAT TAA ATA CTA ACG | GLRaV-2 intergenic region of CP (nts 9568-9651 Genbank Accession number DQ286725) (F.P.) |
| C-1976 | CAG CTT GCT TCT ACCTGA CAC AGT TAA GAA GCG GCATAA ATC GAA GCC AAA CCCTAA ATT TTG CAA CTC GAT CAATTG TAA CCT AGA GCG AAGTGC AAT CA | BYSV CP intergenic region of (nts 8516-8616 Genbank accesion # U51931) (F.P). |
| C-1977 | TTT AGC GCA TAT TAA ATA CTA ACG ATG GCT AGC AAA GGA GAA GAA | 5' end of GFP (nts 1-21) with extension into the 3'end of GLRaV-2 CP intergenic region (nts 9628-9651 Genbank Accession number DQ286725) (F.P.) |
| C-1979 | ACT GTG TCA GGT AGA AGC AAG CTG TCA GAT GAA GTG GTGTTC ACG | 3'end of p23 (nts 19,000-19,020 of CTV T36 clone) with extension into 5'end of BYSV CP IR (nts 8516-8539 Genbank accesion # U51931) (R.P.) |
| C-1982 | TTG G***AT TTA GGT GAC ACT ATA G***TG GAC CTATGTTGG CCC CCC | Sp6 promoter (underlined and Italics) with 3' end of 3'NTR (nts 19271-19293 |

TABLE 1-1-continued

List of primers used in building expression vector

| Primer name | Sequence 5'-3'* | Description* |
|---|---|---|
| | ATA | of CTV T36 clone) used to develop dig labeled probe (R.P.) |
| C-1983 | GTA ACCTAG AGC GAA GTG CAA TCA ATG GCT AGC AAA GGA GAA GAA | 5'end of GFP (nts 1-23) with extension into 3'end of BYSV IR of CP ( nts 8593-8616 Genbank Accession #U51931) (F.P.) |
| C-1984 | GCC TAA GCT TAC AAA TAC TCC CCC ACA ACA GCT TAC AAT ACT CCC CCA CAC AGC TTA CAA ATA CTC CCC CAC AAC AGCTTG TCG AC | 3X active ribosome complementary sequence (3XARC-1 nts 1-86) (Akbergenov et al., 2004) (F.P.) |
| C-1985 | CTC CGT GAA CAC CACTTC ATC TGA AAA TAA CAA ATC TCA ACA CAA | 5' end of TEV 5'NTR (nts 1-21 Genbank Accession # M11458) with extension into 3' end of p23 (nts 18997-19020 of CTV T36 clone) (F.P.) |
| C-1986 | TTG TGT TGA GAT TTG TTA TTT TCA GAT GAA GTG GTG TTC ACG GAG | 3'end of p23 (nts 18997-19020 of CTV T36 clone) with extension into 5' end of TEV 5'NTR (nts 1-21 Genbank Accession # M11458) (R.P.) |
| C-1989 | GGA GTATTT GTA AGCTTA GGC TCA GAT GAA GTG GTGTTC ACG GAG | 3'end of p23 (nts 18997-19020 of CTV T36 clone) with extension into 5'end of 3XARC-1 (nts 1-21) (R.P.) |
| C-1990 | CCC CAC AAC AGCTTG TCG ACA TGG CTA GCA AAG GAG AAG AAC TTT | 5'end of GFP (nts 1-25) with extension into 3'end of 3XARC-1 (nts 66-86) (F.P.) |
| C-2007 | CGT GAA CAC CACTTC ATC TGA TTC GAC CTC GGT CGT CTT AGT TAA | BYV 3'end of CPm and the intergenic region of CP (nts 13547-13570 Genbank Accession # AF190581) with extension into p23 3'end (nts 19,000-19,020 of CTV T36 clone) (F.P.) |
| C-2008 | TTA ACT AAG ACG ACC GAG GTC GAA TCA GAT GAA GTG GTG TTC ACG | 3'end of p23 (nts 19,000-19,020 of CTV T36 clone) with extension into the 3'end of CPm and CP intergenic region of BYV (nts 13,547-13,570 Genbank Accession # AF190581) (R.P.) |
| C-2009 | GGC GAT CAC GAC AGA GCC GTGTCA ATT GTC GCG GCT AAG AAT GCT GTG GAT CGC AGC GCT TTC ACT GGA GGG GAG AGA AAA ATA GTT AGT TTG TAT GCCTTA GGA AGG AACTAA GCA CGT TGT GCT ATA GTA CGT GC | GLRaV-2 3'end of CPm and 5' end of CP intergenic region (nts 9454-9590 Genbank Accession number DQ286725) (F.P.) |
| C-2010 | TGA CAC GGC TCT GTC GTG ATC GCC TCA GAT GAA GTG GTGTTC ACG | 3'end of p23 (nts 19,000-19,020 of CTV T36 clone) with extension into the 3'end of GLRaV-2 CPm |

TABLE 1-1-continued

List of primers used in building expression vector

| Primer name | Sequence 5'-3'* | Description* |
|---|---|---|
| | | coding sequence (nts 9454-9477 Genbank Accession #DQ286725) (R.P.) |
| C-2011 | GCC ACC TAC GTT ATA GGT CTT CAT TTT GTA GAG CTC ATC CAT GCC | 3'end of GFP (nts 697-717) with extension into the TEV HC-Pro protease recognition sequence (nts 2412-2435 (genetic code redundancy used to eliminate duplication Genbank Accession # M11458) (R.P.) |
| C-2012 | AAG ACC TAT AAC GTA GGT GGC ATG AAG GCT CAATAT TCG GAT CTA | 5' end of TEV HC-Pro protease motif (nts 1959-1979 Genbank Accession #M11458) with extension into the HC-Pro recognition sequence (nts 2415-2438 genetic code redundancy used to eliminate duplication Genbank Accession # M11458) (F.P.) |
| C-2013 | ATG AAA ACT TAC AAT GTT GGA GGG ATG TTA CGT CCT GTA GAA ACC | 5'end of GUS (nts 4-21) with extension into the TEV HC-Pro recognition sequence and 3' end of TEV HC-Pro protease motif (nts 2412-2438 Genbank Accession # M11458) (F.P.) |
| C-2014 | GGT TTC TAC AGG ACG TAA CAT CCC TCC AAC ATT GTA AGT TTT CAT | TEV HC-Pro recognition sequence (nts 2412-2438 Genbank Accession # M11458) with extension into the 5' end of GUS ORF sequence (nts 4-21) (R.P.) |
| C-2015 | CCG CAG CAG GGA GGC AAA CAA TGA TTG AAGTGG ACG GAA TAA GTT | 5' end of 3'NTR (nts 19021-19041 of CTV T36 clone) with extension into the 3' end of GUS ORF (nts 1789-1812) (F.P.) |
| C-2016 | AAC TTA TTC CGT CCA CTT CAA TCA TTG TTT GCCTCC CTG CTG CGG | 3' end of GUS (nts 1789-1812) with extension into the 5'end of 3'NTR (nts 19021-19041 of CTV T36 clone) (R.P.) |
| C-2017 | CTT ACT CTG AAA ATA AAG ATT CTC TTT GTA GAG CTC ATC CAT GCC | 3'end of GFP (nts 697-717) with extension into the 5'end of TEV-NIa protease recognition sequence (nts 8499-8519 Genbank Accession # M11458) and 5' end of TEV NIa protease motif (nts 6270-6272 Genbank Accession #M11458) (R.P.) |
| C-2018 | AAA GAG AAT CTT TAT TTT CAG AGT AAG GGA CCA CGT GAT TAC AAC | 5' end of TEV NIa protease motif (nts 6270-6290 Genbank Accession #M11458) with extension into its recognition |

TABLE 1-1-continued

List of primers used in building expression vector

| Primer name | Sequence 5'-3'* | Description* |
|---|---|---|
| | | sequence (nts 8499-8519 Genbank Accession # M11458) and 3' end of GFP (nts 715-717) (F.P.) |
| C-2019 | CGA TTG GAA GTA TAG GTT TTC TTG CGA GTA CAC CAA TTC ACT CAT | 3'end of TEV NIa motif (nts 6961-6980 Genbank Accession #M11458) with extension into NIa recognition sequence (nts 8499-8519 Genbank Accession #M11458 genetic code redundancy used to eliminate duplication) (R.P.) |
| C-2020 | CAA GAA AAC CTA TAC TTC CAA TCG ATG TTA CGT CCT GTA GAA ACC | 5'end of GUS with extension into the TEV NIa recognition sequence (nts 8499-8519 Genbank Accession #M11458 genetic code redundancy used to eliminate duplication) and 3' end of TEV NIa protease motif (nts 6978-6980 Genbank Accession #M11458) (F.P.) |
| C-2021 | GTC ACT TTG TTT AGC GTG ACT TAG CAG CTT GCT TCT ACC TGA CAC | 5'end of BYSV CP IR (nts 8516-8536 Genbank Accession #U51931) with extension into 3'end of p18 (nts 17269-17292 of CTV T36 clone) (F.P.) |
| C-2022 | GTG TCA GGT AGA AGC AAG CTG CTA AGT CAC GCT AAA CAA AGT GAC | 3' end of p18 (nts 17269-17292 of CTV T36 clone) with extension into 5' end BYSV CP IR (nts 8516-8536 Genbank Accession #U51931) (R.P.) |
| C-2023 | TTA GTC TCT CCA TCT TGC GTG TAG CAG CTT GCT TCT ACC TGA CAC | 5'end of BYSV CP IR (nts 8516-8536 Genbank Accession #U51931) with extension into the 3'end of p20 (nts 18286-18309 of CTV T36 clone) (F.P.) |
| C-2024 | GTG TCA GGT AGA AGC AAG CTG CTA CAC GCA AGATGG AGA GAC TAA | 3'end of p20 (nts 18286-18309 of CTV T36 clone) with extension into the 5' end of BYSV CP IR (nts 8516-8536 Genbank Accession #U51931) (R.P.) |
| C-2025 | ATG GAT GAG CTC TAC AAA TGA--GTT TCA GAA ATT GTC GAATCG CAT | 3'end of p13 ORF (nts 17581-17604 of CTV T36 clone) with extension into the 3'end of GFP ORF (nts 700-720) (F.P.) |
| C-2026 | ATG CGA TTC GAC AAT TTC TGA AAC TCA TTT GTA GAG CTC ATC CAT | 3'end of GFP ORF (nts 700-720) with extension into the 3'end of p13 ORF (nts 17581-17604 of CTV T36 clone) (R.P.) |
| C-2027 | ATG GAT GAG CTC TAC AAA TGA GTT AAT ACG CTT CTC AGA ACG TGT | 5'end of p23 IR (nts 18,310-18,330 of CTV T36 clone) with extension into 3' end of GFP (nts 700-720) (F.P.) |

TABLE 1-1-continued

List of primers used in building expression vector

| Primer name | Sequence 5'-3'* | Description* |
|---|---|---|
| C-2028 | ACA CGT TCT GAG AAG CGT ATT AAC TCA TTT GTA GAG CTC ATC CAT | 3'end of GFP (nts 700-720) with extension into p23 IR (nts 18310-18330 of CTV T36 clone) (R.P.) |
| C-2029 | TTT AGC GCATAT TAA ATA CTA ACG ATG TAC CCATAC GAT GTT CCA | 5' end of HA TAG (21nts) in pHA-CMV carrying bFos (AA 118-210)-YC (AA 155-238) (Hu et al., 2002) with extension into the GLRaV-2 CP IR 3' end (nts 9628-9651 Genbank Accession number DQ286725) (F.P.) |
| C-2030 | TGG AAC ATC GTATGG GTA CAT CGT TAGTAT TTA ATATGC GCT AAA | 3' end of CPm GLRaV-2 (nts 9628-9651 Genbank Accession number DQ286725) with extension into 5' end of HA tag (21nts) in pHA-CMV carrying bFos (AA 118-210)-YC (AA 155-238) (Hu et al., 2002) (R.P.) |
| C-2031 | ACT GTGTCA GGT AGA AGC AAG CTG TTA CTT GTA CAG CTC GTC CAT | 3'end EYFP-YC (AA 232-238) (Hu et al., 2002) with extension into the BYSV CP 5'IR (nts 8516-8539 Genbank Accession # U51931) (R.P.) |
| C-2032 | GTA ACCTAG AGC GAA GTG CAATCA ATG GACTAC AAA GAC GAT GAC | 5'end of FLAG tag (21nts) from pFLAG-CMV2 carrying bJunN (Hu et al., 2002) with extension into the 3'end of BYSV CP IR (nts 8593-8616 Genbank Accession #U51931) (F.P.) |
| C-2051 | GTC ACT TTG TTT AGC GTG ACT TAG GGC GAT CAC GAC AGA GCC GTG | 3'end of GLRaV-2 CPm (nts 9454-9474 Genbank Accession #DQ286725) with extension into 3'end of p18 (nts 17269-17292 of CTV T36 clone) (F.P.) |
| C-2052 | CAC GGC TCT GTC GTG ATC GCC CTA AGT CAC GCT AAA CAA AGT GAC | 3'end of p23 (nts 19,000-19,020) with extension into the 3'end of GLRaV-2 CPm coding sequence (nts 9454-9474 Genbank Accession #DQ286725) (R.P.) |
| C-2053 | GTC ACT TTG TTT AGC GTG ACT TAG TTC GAC CTC GGT CGT CTT AGT | BYV 3'end of CPm and the intergenic region of CP (nts 13547-13567 Genbank Accession # AF190581) with extension into 3'end of p18 (nts 17269-17292 of CTV T36 clone) (F.P.) |
| C-2054 | ACT AAG ACG ACC GAG GTC GAA CTA AGT CAC GCT AAA CAA AGT GAC | 3'end of p18 (nts 17269-17292 of T36 CTV clone) with extension into BYV 3'end of CPm and the intergenic region of CP (nts 13547-13567 Genbank Accession # AF190581) (R.P.) |

TABLE 1-1-continued

List of primers used in building expression vector

| Primer name | Sequence 5'-3'* | Description* |
|---|---|---|
| C-2055 | CAC AAC GTC TAT ATC ATG GCC TAG GTT TCA GAA ATT GTC GAA TCG | 3'end of p13 ORF (nts 17581-17601 of CTV T36 clone) with extension into the 3'end of EYFP-YN(AA 147-154) from pFlag-CMV2 carrying bJun-YN (Hu et al., 2002) |
| C-2056 | CGA TTC GAC AAT TTC TGA AAC CTA GGC CAT GAT ATA GAC GTT GTG | 3'end of EYFP-YN(AA 147-154) from pFlag-CMV2 carrying bJun-YN (Hu et al., 2002) with extension into the 3'end of p13 (nts 17581-17601 of CTV T36 clone) |
| C-2057 | GGC ATG GAC GAG CTG TAC AAGTAA TTG AAGTGG ACG GAATAA GTT | 3'end EYFP-YC (AA 231-238) (Hu et al., 2002) with extension into 5'end of 3'NTR (nts 19021-19041 of CTV T36 clone) |
| C-2058 | AAC TTA TTC CGT CCA CTT CAA TTA CTT GTA CAG CTC GTC CAT GCC | 5'end of 3'NTR (nts 19021-19041 of CTV T36 clone) with extension into 3'end EYFP-YC (AA 231-238) (Hu et al., 2002) |
| C-2059 | TCG CTC TTA CCT TGC GAT AAC TAG CAG CTT GCT TCT ACCTGA CAC | BYSV CP SIR (nts 8516-8536 Genbank Accession #U51931) with extension into the 3'end of p13 (nts 17,662-17,685 of CTV T36 clone) (F.P.) |
| C-2063 | GTA ACCTAG AGC GAA GTG CAA TCA ATG TTA CGT CCT GTA GAA ACC | 5'end of GUS ORF (nts 1-21) with extension into the 3' end of BYSV CP IR (with extension into the 3'end of BYSV CP IR (nts 8593-8616 Genbank Accession #U51931) (F.P.) |
| C-2064 | GGT TTC TAC AGG ACG TAA CAT TGA TTG CACTTC GCT CTA GGTTAC AA | 3'end of BYSV CP IR (nts 8591-8616 Genbank Accession #U51931) with extension into the 5' end of GUS ORF (nts 1-21)(R.P) |
| C-2067 | CCG CAG CAG GGA GGC AAA CAA TGA GTT TCA GAA ATT GTC GAATCG | 3'end of p13 (nts 17581-17601 of CTV T36 clone) with extension into the 3'end of GUS (nts 1789-1812) (F.P.) |
| C-2068 | CGA TTC GAC AAT TTC TGA AAC TCA TTG TTT GCCTCC CTG CTG CGG | 3'end of GUS (nts 1789-1812) with extension into the 3'end of p13 (nts 17581-17601 of CTV T36 clone) |
| C-2069 | GTG TCA GGT AGA AGC AAG CTG CTA GTT ATC GCA AGG TAA GAG CGA | 3'end of p13 (nts 17662-17685 of CTV T36 clone) with extension into 5'end of BYSV IR CP SIR (nts 8516-8536 Genbank Accession #U51931) (R.P.) |
| C-2070 | ATG GAT GAG CTC TAC AAATGA AGT CTA CTC AGT AGT ACG TCT ATT | 5'IR of p20 (nts 17686-17709 of CTV T36 clone) with extension into the 3'end of GFP (nts 700-720) (F.P.) |

TABLE 1-1-continued

List of primers used in building expression vector

| Primer name | Sequence 5'-3'* | Description* |
|---|---|---|
| C-2071 | AAT AGA CGT ACT ACT GAGTAG ACT TCA TTT GTA GAG CTC ATC CAT | 3'end of GFP (nts 700-720) with extension into the SIR of p20 (nts 17686-17709 of CTV T36 clone) (R.P.) |
| C-2085 | GCG G ATGCAT TATTT GGTTTT ACA ACA ACG GTA CGT TTC AAA ATG | 3'end of p18 (nts 17201-17245 of CTV T36 clone) with two point mutations (C-A(17205) and G-T(17210)) creating NsiI site to replace the PstI site (F.P.) |
| C-2087 | AAG ACC TAT AAC GTA GGT GGC ATG AAG GCT CAA TAT TCG GAT CTA | 5' end of TEV HC-Pro protease motif (nts 1959-1979 Genbank Accession #M11458) with extension into the HC-Pro recognition sequence (nts 2415-2438 genetic code sequence redundancy was used to eliminate duplication Genbank Accession #M11458) (F.P.) |
| C-2088 | ATG AAA ACT TAC AAT GTT GGA GGG ATG GCT AGC AAA GGA GAA GAA | 5'end of GFP ORF(nts 4-21) with extension into the TEV HC-Pro recognition sequence (nts 2412-2438 Genbank Accession #M11458) (F.P.) |
| C-2089 | TTC TTC TCC TTT GCT AGC CAT CCC TCC AAC ATT GTA AGT TTT CAT | TEV HC-Pro recognition sequence (nts 2412-2438 Genbank Accession #M11458) with extension into the 5' end of GFP ORF sequence (nts 4-21) (R.P.) |
| C-2091 | GAG AAT CTT TAT TTT CAG AGT AAG GGA CCA CGT GAT TAC AAC C | 5' end of TEV NIa protease motif (nts 6270-6291 Genbank Accession #M11458) with extension into its recognition sequence (nts 8499-8519 Genbank Accession #M11458) (F.P.) |
| C-2092 | GAA AAC CTA TACTTC CAATCG ATG GCT AGC AAA GGA GAA GAA CT | 5'end of GFP ORF (nts 1-23) with extension into the TEV-NIa protease recognition sequence (nts 8499-8519 genetic code seqence redundancy used to eliminate duplication Genbank Accession #M11458) (F.P.) |
| C-2093 | AGT TCT TCT CCT TTG CTA GC CAT CGA TTG GAA GTA TAG GTT TTC | TEV NIa protease recognition sequence (nts 8499-8519 genetic code sequence redundancy used to eliminate duplication Genbank Accession #M11458) with extension into the GFP ORF sequence (nts 1-23) (R.P.) |
| C-2094 | AAG ACCTAT AAC GTA GGT GGC ATG AAG GGA CCA CGT GAT TAC | 5' end of TEV-NIa protease motif sequence nts 6270-6291 Genbank |

TABLE 1-1-continued

List of primers used in building expression vector

| Primer name | Sequence 5'-3'* | Description* |
|---|---|---|
| | AAC | Accession #M11458) with extension into the HC-Pro recognition sequence (nts 2415-2438 genetic code sequence redundancy was used to eliminate duplication Genbank Accession #M11458) (F.P.) |
| C-2095 | CCC TCC AAC ATT GTA AGT TTT CAT TTG CGA GTA CAC CAATTC ACT | 3'end of TEV NIa protease motif(nts 6959-6981 Genbank accession # DQ986288) with extension into the TEV HC-Pro protease motif (nts 2415-2438 Genbank accession #M11458) (R.P.) |
| C-2096 | GAG AAT CTT TAT TTT CAG AGT AAG GCT CAATAT TCG GAT CTA AAG | 5'end of TEV HC-Pro protease motif (nts 1959-1979 Genbank Accession #M11458) with extension into the TEV NIa protease recognition sequence (nts 8499-8519 Genbank accession #M11458) (F.P.) |
| C-2097 | CGA TTG GAA GTATAG GTT TTC TTC GGATTC CAA ACCTGA ATG AAC | 3'end of HC-Pro protease motif (nts 2388-2411 Genbank accession # M11458) with extension into the TEV NIa protease recognition sequence (nts 8499-8519 Genbank accession # M11458)(R.P.) |
| C-2098 | GCC ACCTAC GTT ATA GGT CTT CAT GAT GAA GTG GTGTTC ACG GAG | 3'end of p23(nts 18997-19017 of CTV T36 clone) with extension into the 5'end of TEV HC-Pro protease recognition sequence (nts 2412-2435 (genetic code seqence redundancy used to eliminate duplication) Genbank Accession # M11458) (R.P.) |
| C-2099 | ACT CTG AAA ATA AAG ATT CTC GAT GAA GTG GTGTTC ACG GAG AAC | 3'end of p23 (nts 18994-19017 of CTV T36 clone) with extension into the 5'end of TEV NIa protease recognition sequence (nts 8499-8519 Genbank Accession #M11458) (R.P.) |
| M-804 | CAT TTA CGA ACG ATA GCC ATG GCT AGC AAA GGA GAA GAA | 5'end of GFP (nts 1-20) with 3'end of TEV 5'NTR (nts 126-143 Genbank Accession #M11458) (F.P.) |

Polymerase Chain Reaction (PCR)

PCR was performed using diluted plasmids (1:50) as templates using Vent DNA polymerase (New England Biolabs, Ipswich, Ma.) according to the manufacturer recommendations.

Agro-Injection/Infiltration

Agro-inoculation of *Nicotiana benthamiana* was performed according to the procedure developed by Gowda et al., (2005) with minor modifications. *Agrobacterium tumefaciens* EHA 105 was transformed with the binary plasmid containing CTV, variants (expression vectors) and silencing suppressors (p19 of Tomato bushy stunt virus (Gowda et al., 2005); p24 of GLRaV-2 (Chiba et al., 2007), P1/HC-Pro of Turnip mosaic virus (Kasschau et al., 2003) and p22 of Tomato chlorosis virus (Cañizares et al., 2008) by heat shock method (37° C. for 5 minuets) and subsequently were grown at 28° C. for 48 hours (hrs) on luria burtani (LB) (Sigma-Aldrich, St Louis, Mo.) plates supplemented with antibiotics (kanamycin (50 microgram (μg)/milliliter (ml)) and Rifampicilin ((50 μg/ml)). The colonies (two individual colonies per construct) were grown overnight as seed cultures in LB medium supplemented with antibiotics. On the next day 0.5 ml of the seed culture was used to inoculate 35 ml of LB medium supplemented with antibiotics for overnight growth. The bacterial culture was centrifuged at 6,000 rotation per minute (rpm) and resuspended in 10 milli molar (mM) $MgCL_2$ and 10 mM MES. The pellet was washed with 10 mM $MgCL_2$ and 10 mM MES and suspended in induction medium; 10 mM $MgCL_2$ and 10 mM MES containing acetosyringone at a final concentration of 150 μM. The suspension was incubated in the induction medium for at least 5 hrs before injection into the stem or infiltration into the abaxial (lower) surface of *N. benthamiana* leaves.

Plant Growth Conditions

*N. benthamiana* plants maintained in a growth-room (21° C. with 16 hrs of light in a 24 hr period) were used for agro-injection/agro-infiltration four weeks after tansplanting.

Infection of *Citrus* Plants

Recombinant virions of CTV for infection of citrus plants were obtained from infiltrated and/or systemic leaves of *N. benthamiana*. The virions were partially purified and enriched by concentration over a sucrose cushion in a TL 100 or SW41 rotor (Robertson et al., 2005). Virions of constructs expressing two foreign proteins were concentrated two times over a step gradient followed by a cushion gradient in SW28 and SW41 rotors, respectively (Garnsey and Henderson, 1982). Inoculation of citrus plants was carried out by bark flap inoculation into 1-1.5 year old *Citrus macrophylla* seedlings (Robertson et al., 2005) which were grown in a greenhouse with temperatures ranging between approximately 25-32° C.

Protoplast Preparation, Transfection, RNA Isolation and Northern Blot Analysis

*N. benthamiana* leaf mesophyll protoplasts were prepared according to the procedure previously developed by Nava-Castillo et al., (1997). Surface sterilized leaves from three week old *N. benthamiana* plants were gently slashed on the lower side with a sterile blade and incubated overnight in the dark (16-20 hrs) in 0.7M MMC (0.7M mannitol, 5 mM MES, 10 mM $CaCl_2$) supplemented with the 1% cellulose (Yakult Honsh, Tokyo, Japan) and 0.5% macerase pectinase enzymes (Calbiochem, La Jolla, Ca.).

Capped in vitro RNA transcripts from NotI or StuI linearized plasmid DNA were generated (Satyanarayana et al., 1999) using Sp6 RNA polymerase (Epicentre Technologies, WI) and were transfected into the protoplasts using PEG (poly ethylene glycol) as described by Satyanarayana et al., (1999). Four days after transfection, protoplasts were used for preparation of total RNA for northern blot hybridization analysis and isolation of virions. Protoplasts were pelleted in equal amounts in two 1.5 ml eppendorf tubes. The first tube was flash frozen in liquid nitrogen and stored at −80° C. for isolation of virions to subsequently inoculate a new batch of protoplasts to amplify virions (Satyanarayana et al., 2000). The second tube was used for RNA isolation by the buffard buffer disruption of protoplasts followed by phenol: chloroform:isoamyl alcohol (25:24:1) extraction and ethanol precipitation as previously described by Navas-Castillo et al., (1997) and Robertson et al., (2005). Total RNA was resuspended in 20 μl DNAse/RNAase free water and used in Northern blot hybridization analysis as previously described by Lewandowski and Dawson (1998). In brief, isolated RNA was heat denatured in denaturing buffer (8.6% formaldehyde, 67% formamide in 1×MOPS (5 mM sodium acetate, 1 mM EDTA, 0.02M MOPS pH=7.0) separated in a 0.9% agarose gel in 1×MOPS containing 1.9% formaldehyde, and transferred onto a nylon membrane (Boehringer Mannheim, Germany) by electroblotting. Prehybridization (at least 1 hr) and hybridization (overnight) were carried out in a hybridization oven (Sigma-Aldrich, St. Louis, Mo.) at 68° C. A 900 nts digoxigenin labeled RNA probe corresponding to the 3' end of the CTV genome (plus strand specific CTV RNA probe) (Satyanarayana et al., 1999) was used for hybridization except when the insertion of the foreign genetic material was behind p23 in which case a digoxigenin labeled RNA probe was produced from PCR amplified DNA (reverse primer contain 3'NTR of CTV and SP6 phage promoter (C-1982) according to the manufacturer recommendation (Boehringer Mannheim, Germany) that is complimentary to the sequence inserted behind p23 in addition to the 3'NTR sequence of CTV.

Western Blots

After powdering the plant tissue in liquid nitrogen via grinding in a mortar and pestle, laemmli buffer (50 mM Tris-Cl, pH 6.8, 2.5% 2-mercaptoethanol, 2% SDS, 0.1% bromophenol blue, 10% glycerol) was added (100 μl per 100 mg tissue). The sample was transferred to a 1.5 ml centrifuge tube and boiled in a water bath for 3 minutes followed by centrifugation at maximum speed for 2 minutes. The supernatant was transferred to a new tube and stored at −20° C. until further use. The electrophoresis was carried out in a 12% SDS-Polyacrylamide gel (Bio-Rad, Hercules, Ca.) followed by two hours of semi-dry blotting to transfer the protein onto a nitrocellulose membrane (Bio-Rad, Hercules, Ca.). The membrane was blocked for 1 hr at room temperature followed by incubation with the primary antibody of either CP (1:5000), GFP (1:100) (Clontech Laboratories, Palo Alto, Ca.) or GUS (1:1000) (Molecular probes, Eugene, Or.) for an hour followed incubation for 1 hr in horseradish peroxidase conjugated donkey anti-rabbit secondary antibody (1:10,000) (Amersham, Buckinghamshire, United Kingdom). Finally, the chemiluminescent system for western blot (Amersham, Buckinghamshire, United Kingdom) development on an X-ray film (Kodak, Rochester, N.Y.) was used according to the manufacturer recommendations.

Plant and Protoplast Photos

Plant pictures under UV or white light were taken with a Canon Camera (Canon EOS Digital Rebel XTi 400D, Lake Success, N.Y.). Close up fluorescent pictures of plant parts or protoplast were taken using a fluorescent dissecting microscope (Zeiss Stemi SV 11 UV-fluorescence dissecting microscope, Carl Zeiss Jena, GmbH., Jena, Germany). High resolution protoplast pictures were taken using a confocal scanning microscope (Leica TCS SL, Leica Microsystems, Inc., Exton, Pa.).

Enzyme Linked Immunosorbent Assay (ELISA)

Double antibody sandwiched ELISA was used according to the procedure developed by Garnsey and Cambra (1991). A rabbit polyclonal antibody (1 µg/ml) was used for coating the ELISA plate. The plant tissue sample was diluted at a 1:20 in PBS-T (phosphate buffer saline-1% Tween 20) extraction buffer. The detection antibody used was Mab ECTV 172 (1:100K dilution).

GUS Assay

Citrus bark pieces or systemic leaves from Agro-inoculated N. benthamiana plants that were surface sterilized in alcohol (70% ethanol) followed by Sodium hypo chloride (10% solution) and washing three times in sterile distilled water before staining for GUS. The samples were incubated overnight in an EDTA-phosphate buffer (0.1M $Na_2HPO_4$, 1 mM $Na_2EDTA$) containing 1 mg/ml X-gluc (cyclohexylammounium salt: Gold Biotechnology, St Louis, Mo.). Fixing of the tissue was done in 95% ethanol:glacial acetic acid solution (3:1.

Example 1: Systems Used to Examine CTV-Based Expression Vectors

CTV-based expression vectors were examined in three systems, N. benthamiana mesophyll protoplasts as well as whole plants of N. benthamiana and Citrus macropylla. The full-length cDNA clone of CTV (pCTV9R) and a mutant with most of the p33 gene deleted (pCTV9RΔp33), which has a PstI restriction site removed making cloning easier and still retaining the ability to infect most citrus varieties (Tatineni et al., 2008), was used for building constructs to infect whole plants. Relatively quick assays were done in N. benthamiana protoplasts, which require constructs to be built in the SP6 transcription plasmid (Satyanarayana et al., 1999). A mini-replicon pCTVΔCla 333R (Gowda et al., 2001), with most of the 3' genes removed, was convenient to use in protoplasts. The ultimate goal to obtain citrus trees infected with the different CTV expression vectors was much more difficult and time consuming So far, agroinoculate citrus trees has proven difficult. Thus, to avoid this difficulty virions are amplified and concentrated for inoculation of citrus trees by stem-slashing or bark-flap inoculation (Robertson et al., 2005; Satyanarayana et al., 2001). N. benthamiana protoplasts can be inoculated with in vitro produced transcripts of recombinant CTV constructs and the virus amplified by successively passaging virions in crude sap through a series of protoplasts (Folimonov et al., 2007; Satyanarayana et al., 2001; Tatineni et al., 2008). Also, recombinant CTV can be amplified in N. benthamiana plants after agro-inoculation (Gowda et al., 2005). The virus can infect mesophyll cells of agro-inoculated areas of leaves, but as the virus moves systemically into upper non-inoculated leaves, it is limited to vascular tissues and usually induces vein clearing and later vein necrosis. All of the vector constructs were examined during systemic infection of N. benthamiana plants. Since CTV virions do not resuspend after centrifugation to a pellet, virions have to be concentrated by centrifugation through a sucrose step gradient (Garnsey et al., 1977; Robertson et al., 2005). After inoculation, the tops of citrus plants were removed, and viral systemic infections were monitored in new growth after 2-3 months. Once trees were infected, inoculum (buds, leaf pieces, or shoots) from the first infected plants was then used to propagate new plants for experimentation. The whole process takes approximately one year. For this reason, the inventors chose to examine only the most promising vector constructs in citrus trees. Some of the later developed constructs are not yet in citrus.

Example 2: Addition of an Extra Gene at Different Locations within the CTV Genome Insertions at the p13 Gene Site The effective CTV vector developed previously (Folimonov et al., 2007) has the additional gene inserted between the two coat protein genes, positioning the foreign gene as the sixth gene from the 3' terminus. Yet, the most highly expressed genes of CTV tend to be closer to the 3' terminus. Thus, it appeared that positioning an inserted gene closer to the 3' terminus could result in higher levels of expression. P13, the third gene from the 3' terminus, is a relatively highly expressed gene that is not necessary for the infection of most of the CTV host range (Tatineni et al., 2008; Tatineni et al., in preparation). Yet, replacement of the p13 ORF with the GFP ORF was not successful in previous attempts (Folimonov et al., 2007). There were possible reasons for the failure. The previous construct was designed with the assumption that translation initiated at the first start codon, but the p13 ORF has a second in-frame AUG. Translation might normally start at the second AUG. However, fusion of the GFP ORF behind the second in frame AUG also did not express the reporter gene (Gowda et al., unpublished result). A second possibility is that the p13 controller element (CE) might extend into the p13 ORF or that ribosome recruitment is directed from within the ORF. Here, the inventors deleted the p13 CE and ORF and inserted a new ORF behind a heterologous CE in the p13 position. The GFP ORF controlled by the CP-CE from BYSV (101 nts from 8516-8616 accession # U51931), GLRaV-2 (198 nts from 9454-9651 accession # DQ286725) or BYV were engineered into pCTV9RΔp33 as a replacement for nts 17293-17581 (CTV33-Δ13-BY-GFP-57, CTV33-Δ13-G-GFP-65, CTV33-Δ13-B-GFP-66 respectively) (FIG. 1 A). RNA transcripts were used to inoculate a series of protoplasts to determine whether the constructs could replicate and whether virions formed sufficiently for passage in crude sap to a new batch of protoplasts. The fluorescence of infected protoplasts (data not presented) and northern blot hybridization analysis demonstrated the successive passage of the expression vectors through the protoplast transfers (FIG. 1B). Furthermore, the level of the GFP mRNA was similar to that of CP. Vectors sequences CTV33-Δ13-BY-GFP-57, CTV33-Δ13-G-GFP-65 and CTV33-Δ13-B-GFP-66 then were transferred into the Agrobacterium binary plasmid for agro-inoculation of N. benthamiana plants. All three vectors infected and moved systemically in vascular tissue of the *N. benthamiana* plants as indicated by fluorescence in leaves, buds, flowers and corolla (FIG. 1C), vein clearing phenotype in early stages, as well as confirmed by ELISA (Data not presented).

CTV33-Δ13-G-GFP-65 and CTV33-Δ13-B-GFP-66 were amplified and used to inoculate *Citrus macrophylla* plants. The initially infected plants exhibited bright fluorescence in vascular tissue (FIG. 1D). Fluorescence continued in these plants 2 years after inoculation.

The GFP ORF (720 nts) was replaced with the GUS ORF (1812 nts) in the same position to examine the expression of a larger foreign gene. The BYSV CP-CE was selected to drive the GUS ORF in expression vector CTV33-Δ13-BY-GUS-61 (FIG. 2A). RNA transcripts of this construct were transfected into protoplast where the virus replicated and passaged efficiently from one protoplast batch to another as indicated by northern blot hybridization analysis (FIG. 2B). In addition, it revealed that the level of accumulation of GUS mRNA was identical to the CP mRNA, and the CP and CPm mRNAs of vector were similar to that of the wild type virus. Agro-inoculation of *N. benthamiana* plants revealed that the construct infected and spread throughout the vascular tissue of the plants based on GUS staining and confirmed by ELISA (Data not presented) and the vein clearing phenotype.

Virions isolated from infiltrated leaves of *N. benthamiana* plants of CTV33-Δ13-BY-GUS-61 infected *Citrus macrophylla* plants as confirmed by ELISA (Data not presented) and the bioactivity of the GUS protein (FIG. 2C). The GUS gene was still biologically active in citrus 1.5 year after inoculation.

Technically, the above constructs replaced a gene (p13) rather than added an extra gene. To examine a vector with an extra gene between p13 and p20, the CP-CE of BYSV controlling the GFP ORF was inserted between nts 17685-17686 to yield CTV33-13-BY-GFP-69 (FIG. 3A). This vector should produce an extra subgenomic RNA between the subgenomic RNAs of p13 and p20. Vector CTV33-13-BY-GFP-69 was examined in *N. benthamiana* protoplasts and plants. In the protoplast system, CTV33-13-BY-GFP-69 replicated efficiently and was successfully passaged from one protoplast batch to another demonstrating efficient replication and virion formation as indicated by fluorescence (Data not presented) and northern blot hybridization analysis (FIG. 3B). The foreign mRNA accumulated at a relatively high level but the CP mRNA was reduced. Similar to the replacement of p13 constructs, agro-inoculation of the expression vector CTV33-13-BY-GFP-69 into *N. benthamiana* plants enabled the new vector to infect and spread throughout the vascular tissue (FIG. 3C).

Construct CTV33-13-BY-GFP-69 infected *C. macrophylla* plants as indicated by strong fluorescence throughout the vascular tissue (FIG. 3C) and confirmed by ELISA (Data not presented). The plants were still fluorescencing 2 years after inoculation.

Insertion Between p20 and p23

To examine expression of a foreign gene closer to the 3' NTR of CTV, an extra gene was inserted between the p20 and p23 genes (nts 18312-18313). The BYV or BYSV CP-CE was used to drive the GFP mRNA in two vectors based on T36 CTV9RΔp33 (CTV33-20-B-GFP-49 and CTV33-20-BY-GFP-58) (FIG. 3-4A). The new vectors produced an extra sgRNA mRNA between the p20 and p23 sgRNAs (FIG. 4B). However, the accumulation of the p20 sg mRNA was substantially reduced. Both vectors replicated and were passaged in protoplasts, but the protoplast passage was reduced as demonstrated by reduced numbers of cells with GFP fluorescence and northern blot hybridization (FIGS. 4B &C). When both CTV33-20-B-GFP-49 or CTV33-20-BY-GFP-58 vectors were infiltrated into *N. benthamiana* leaves for transient expression, the vectors replicated and produced abundant amounts of GFP as indicated by fluorescence (Data not presented) and western blot analysis (FIG. 4D). However, when agro-inoculated into *N. benthamiana* plants, the constructs replicated but movement into upper non-inoculated leaves was random and often unsuccessful. Since systemic infection of *N. benthamiana* plants was marginal, no attempt was made to inoculate citrus.

Insertion Between p23 and 3'NTR

The next position to be examined was to make the inserted gene the 3'-most gene. Since CTV gene expression tends to be highest for genes positions nearer the 3' terminus, this position could be expected to result in the highest level of expression of a foreign gene (Navas-Castillo et al., 1997; Hilf et al., 1995). Although the 3' NTR has been analyzed (Satyanarayana et al., 2002a), it was not known what effect an extra gene in this area would have on the efficiency of replication. The insertion of an extra gene between the CP gene and the 3'NTR in Tobacco mosaic virus (TMV) and Alfalfa mosaic virus (AMV) failed to produce viable vectors (Dawson et al., 1989; Sánchez-Navarro et al., 2001). The CP-CE of BYSV, GLRaV-2 or BYV in front of the GFP ORF was inserted between nucleotides 19020 and 19021 creating vectors CTV33-23-BY-GFP-37, CTV33-23-G-GFP-40 and CTV33-23-B-GFP-42, respectively (FIG. 5A). All of the constructs when transfected into the protoplast replicated and were passaged efficiently as indicated by northern blot hybridization analysis (FIG. 5B) and GFP fluorescence (Data not presented). The GFP mRNA was the highest accumulating mRNA, with only slight decreases to the other mRNAs compared to that of the wild type virus (FIG. 5B). Furthermore, the constructs with a GFP insertion 3' of the p23 ORF had the highest accumulation of the foreign gene mRNA among the constructs examined. CTV33-23-BY-GFP-37, CTV33-23-G-GFP-40 and CTV33-23-B-GFP-42 constructs were agro-inoculated into *N. benthamiana* plants. The infections spread systemically throughout the vascular tissue as demonstrated by the fluorescence (FIG. 5C), phenotype (vein clearing followed by necrosis), and ELISA (Data not presented). The fluorescence in the vascular tissue of *N. benthamiana* plants was extremely bright and continued for the life of the infected plants (FIG. 5C)

Construct CTV33-23-BY-GFP-37 was amplified by passage through 12 protoplast sets before citrus inoculation. *C. macrophylla* plants that were bark-flap inoculated with the concentrated virions became infected. The infection of citrus was confirmed by fluorescence of GFP (FIG. 3-5D) and ELISA (Data not presented). Inoculation of citrus with constructs CTV33-23-G-GFP-40 was done via amplification in agro-inoculated *N. benthamiana* plants. The infection rate was in 1 of 4 *C. macrophylla* plants as indicated by fluorescence (FIG. 5D) and confirmed by ELISA (Data not presented). Similar to *N. benthamiana*, citrus plants expressed bright fluorescence in the vascular tissue 12 weeks after inoculation and were still fluorescing 2.5 years later (FIG. 5D).

To examine the ability of the vector to express a larger gene at this position, the GUS ORF behind the BYSV CP-CE was inserted 3' of the p23 gene resulting in construct CTV33-23-BY-GUS-60 (FIG. 6A). The construct replicated in successfully transfected protoplasts. However, the accumulation levels of all the CTV subgenomic RNAs were decreased profoundly compared to the wild type virus as demonstrated by northern blot hybridization analysis (FIG. 6B). Also, the CTV33-23-BY-GUS-60 construct passaged poorly in protoplasts (Data not presented). Yet, after agro-inoculation of N. benthamiana plants, the vector replicated and moved systemically as demonstrated by the systemic symptoms (vein clearing followed by necrosis), ELISA (Data not presented) and GUS assays. The activity of GUS in the N. benthamiana plants was continuously produced in old and new leaves until the death of the plant (FIG. 7C) Similar to CTV33-Δ13-BY-GUS-61, the location between p23 and 3'NTR was able to accommodate moderately to long genes albeit with a differential effect on sg RNA levels of upstream genes (FIG. 5B & FIG. 6B)

Concentrated virions from Construct CTV33-23-GUS-60 were used to inoculate C. macropyhlla plants, which became infected as confirmed by ELISA (Data not presented) and activity of the GUS gene (FIG. 6C). Furthermore, GUS activity and western blot analysis revealed the presence of the GUS gene in citrus 1.3 years after inoculation (FIG. 6C, FIG. 19).

Example 3: Production of an Extra Polypeptide without Producing an Extra Subgenomic mRNA Internal Ribosome Entry Site Strategy (IRES)
The Tobacco Etch Virus (TEV) IRES The 5'NTR of TEV mediates cap independent translation of the viral mRNA. Studies on the 5'NTR of TEV demonstrate its ability to initiate translation at an internal ORF in a bi-cistronic mRNA (Gallie, 2001; Niepel and Gallie, 1999). The 5'NTR of TEV (nts 2-144 Genbank accession # DQ986288) was inserted into a CTV mini-replicon behind the p23 ORF (between nts 19020-19021) followed by the GFP ORF (CTVp333R-23-ITEV-GFP) (FIG. 7A) to examine whether a bicistronic subgenomic mRNA would work with this virus. Although northern blot hybridization analysis demonstrated that the mini-replicon replicated and produced abundant amounts of the bicistronic mRNA in transfected N. benthamiana protoplasts (FIG. 7C), GFP fluorescence was not observed, suggesting a lack of translation of the second ORF in the bicistronic mRNA. The inventors also examined the 5'NTR TEV IRES construct in full length CTV in N. benthamiana protoplasts and plants. Construct CTV33-23-ITEV-GFP-41 was passaged efficiently from protoplast to the next protoplast sets (FIG. 7B), indicating the good replication and formation of virions, but no fluorescing protoplasts were observed demonstrating that this IRES did not work well in CTV (data not presented). This construct infected and moved systemically in N. benthamiana plants based on the systemic symptoms of vein clearing followed by necrosis and ELISA (Data not presented), but no GFP fluorescence was observed under UV light (Data not presented).

Active Ribosome Complementary Sequence (ARC) IRES

Insertion of an IRES consensus sequence obtained from analysis of host and viral mRNAs (the engineered 3xARC-1 (86 nts) IRES (Akbergenov et al., 2004)) was next examined for activity in CTV. This IRES was fused behind the p23 ORF (nts 19020-19021) in both the CTV mini-replicon (CTVp333R-23-I3xARC-GFP) and Δp33CTV9R (CTV33-23-I3xARC-GFP-43) as described above (FIG. 7A). However, after infection of protoplasts and plants, no GFP fluorescence was observed even though the virus replicated well in both (FIGS. 7B&C).

Poly-Peptide Fusion

P23, the highest expressed gene of CTV, is a multifunctional protein that is essential for citrus infection. P23 is a silencing suppressor and controls plus to minus RNA ratio in infected cells via an RNA binding domain constituted of positive charged amino acid residues and Zn finger domain present between amino acid 50-86 (Lopez et al., 2000; Satyanarayana et al., 2002b; Lu et al., 2004). In order to create a gene fusion the HC-Pro or NIa protease motifs of TEV were selected to be fused at the C-terminus of p23 (between nts 19017 and 19018) (FIG. 8). The protease recognition sequence of the HC-Pro and NIa was duplicated between p23 and the protease and between the protease and GFP creating vectors CTV33-23-HC-GFP-72 and CTV33-23-NIa-GFP-73, respectively (FIG. 8). The processing of the protease motif from p23 should release the p23 with 7 extra amino acids at its C-terminus in the case of HC-Pro and 6 amino acids in the case of NIa. The GFP protein should have two extra and one extra amino acid after being cleaved from HC-Pro and NIa, respectively. The recognition sequences were switched between HC-Pro and NIa creating vectors CTV33-23-HCØ-GFP-74 and CTV33-23-NIaØ-GFP-75 as controls that are unable to be cleaved (FIG. 8). All the polypeptide fusion vectors were created in CTV binary vectors for infection of plants because in protoplast it was shown that p23 fusion did not affect the ability to replicate and pass between protoplast sets (Tatineni and Dawson, unpublished result). In N. benthamiana infiltrated leaves, all constructs fluoresced similarly to each other and to the free GFP constructs behind p23 (FIG. 9A). Furthermore, western immune-blot analysis from infiltrated leaves indicated a near-perfect processing of the reporter gene from the poly-peptide fusion (FIG. 10). The GFP protein did not localize to the nucleus unlike the fusion to p23 without a protease processing releasing the reporter gene. Upon agro-inoculation of plants, only constructs with the protease and its homologous processing sites were able to move systemically into upper non-inoculated leaves. The fluorescence in upper non-inoculated leaves was weaker than those for the expression vectors CTV33-23-BY-GFP-37, CTV33-23-G-GFP-40 and CTV33-23-B-GFP-42 carrying GFP under its own controller element (FIG. 9B). Furthermore, it was easier to visualize fluorescence on the abaxial rather than the adaxial leaf surface (FIG. 9C). Upon inoculation of citrus with construct CTV33-23-HC-GFP-72, one plant became positive with relatively low ELISA value compared to others (Data not presented). The reporter gene activity was not detected.

Example 4: Production of More than One Extra Foreign Protein from CTV Vectors

Use of Single Controller Elements to Express Multiple Proteins

In order to exploit the polypeptide strategy to express multiple genes driven by the same controller element in a CTV based vector, a fusion polypeptide was created consisting of GFP/Protease (Pro)/GUS. Two different protease motifs were used in the different constructs, HC-Pro and NIa, with their proteolytic motifs and recognition sequences separating GFP ORF from the GUS ORF (FIGS. 14A & 3-16) (Carrington and Dougherty, 1988; Carrington et al., 1989). Theoretically, in case the NIa was the protease motif in the fusion, six extra amino acids are coupled with the N-terminal protein (GFP) at its C-terminus whereas only one extra amino acid is added to the N-terminus of GUS Similarly, where HC-Pro was the protease within the fusion poly-peptide, 7 extra amino acids are added to the C-terminus of GFP and two extra amino acids added to the N-terminus of GUS. The fusion genes ranged in size between 3127 and 3480 nts.

Replacement of p13 Gene

The two fusions of GFP/Pro/GUS described above were engineered into the p13 site of CTV in the agro-inoculation binary vector under the control of the BYSV CP-CE (CTV33-Δ13-BYGFP-HC-GUS-77 with HC-Pro protease motif and CTV33-Δ13-BYGFP-NIa-GUS-78 with NIa protease motif) (FIG. 11A). The constructs were agro-inoculated to N. benthamiana for monitoring the ability to systemically infect the plant and produce GUS and GFP. Both genes were produced based on their assays (FIG. 11 B). Western immune-blot analysis indicated the efficient processing of the GFP protein from the polypeptide fusion (FIG. 10). The virus multiplied and spread to high titers in N. benthamiana plants as indicated by symptom development in the upper leaves (FIG. 11B) and ELISA. However, the level of GFP fluorescence was less than that of vectors CTV33-Δ13-BY-GFP-57, CTV33-Δ13-G-GFP-65 and CTV33-Δ13-B-GFP-66 expressing the GFP alone and spread more slowly into the upper non-inoculated leaves than those vectors (Data not presented). In N. benthamiana plants, overlapping fluorescence and enzymatic activity of GUS were demonstrated 7 months after the injection of the construct revealing their stability (FIG. 12).

Insertion Between p23 and 3'NTR

In an attempt to improve the expression level of GFP and GUS, the fusion polypeptide was moved closer to the 3'NTR. The fusion gene with either BYSV, GLRaV-2 or BYV CP-CE with the protease of HC-Pro was inserted between p23 and 3'NTR referred to as CTV33-23-BY-GFP-HC-GUS-51, CTV33-23-G-GFP-HC-GUS-53 and CTV33-23-BY-GFP-HC-GUS-55 whereas with the NIa protease constructs were named, CTV33-23-BY-GFP-NIa-GUS-52, CTV33-23-G-GFP-NIa-GUS-54 and CTV33-23-BY-GFP-NIa-GUS-56, respectively (FIG. 13). After N. benthamiana plants were agro-inoculated, all the constructs multiplied and spread into the upper non-inoculated leaves as indicated by GFP fluorescence (FIG. 14A) and GUS activity (FIG. 14A) Similar to constructs CTV33-Δ13-BYGFP-HC-GUS-77 and CTV33-Δ13-BYGFP-NIa-GUS-78, fluorescence overlapping with GUS enzymatic activity was demonstrated 7 months after injection indicating the stability of the fusion. However, C. macrophylla plants infected with construct CTV33-23-BY-GFP-HC-GUS-51 revealed only faint fluorescence and almost no GUS activity (FIG. 14B) and high ELISA values.

Example 5: Use of Multiple Promoters to Express Foreign Genes Simultaneously

Bimolecular Fluorescence Complementation (BiFC) in CTV.

For examination of the insertion of two CP-CE controlling different ORFs, the BiFC system, which produces visible fluorescence only when the two proteins accumulate in the same cell, was used. This system was developed using the bJun fused to N-terminus of EYFP (A.A. 1-154) (referred to as bJunN) and bFos ORF fused to C-terminus of EYFP (A.A. 155-238) (referred to as bFosC) (Hu et al., 2002).

Both proteins are transported to the nucleus where they directly interact enabling the EYFP protein to regain its wild type folding pattern and results in emission of fluorescence upon activation by a blue light source (Excitation wave length is 525 nm and emission wavelength is 575 nm) (Hu et al., 2002). One or both components of BiFC were introduced into the CTV mini-replicon 3' of the p23 ORF (between nts #19020 and 19021 Genbank Accession # AY170468) referred to as CTVp333R-23-BYbJunN, CTVp333R-23-GbFosC and CTVp333R-23-BYbJunN-GbFosC (FIG. 15 A). Northern blot hybridization analysis demonstrates the successful transfection of all three constructs into N. benthamiana protoplast (FIG. 15B). The two transcription factors interacted in the plant cell as demonstrated by nuclear fluorescence observed only in protoplasts infected with CTVp333R-23-BYbJunN-GBFosC (FIG. 15C). It is worth noting that the size of the two inserted genes is approximately identical to that of the GUS ORF.

As a control for the BiFC experiments, the inventors also introduced the genes individually into Δp33CTV9R behind p23 creating vectors CTV33-23-BYbJunN-97 and CTV33-23-GbFosC-98 so that only one component would be produced (FIG. 16B). Neither construct exhibited fluorescence in the nucleus.

Expression of Multiple Foreign Genes Simultaneously at the Same Location

P13 Replacement.

Both genes were introduced into a Δp33CTV9R (Satyanarayana et al., 1999, 2000, 2003; Tatineni et al., 2008) as a replacement of the p13 gene (replacement of the nucleotides deleted between 17292 and 17581), resulting in CTV33-Δ13-BYbJunN-GbFosC-76 (FIG. 16A). Transfection of protoplasts with the RNA transcripts of CTV33-Δ13-BYbJunN-GbFosC-76 resulted in the nuclear fluorescence of infected protoplasts (Data not presented). Similarly, infiltrated leaves of N. benthamiana plants with full length CTV33-Δ13-BYbJunN-GbFosC-76 emitted nuclear fluorescence (FIG. 16B). On the contrary, infiltrated leaves with constructs CTV33-23-BYbJunN-97 and CTV33-23-GbFosC-98 did not show any nuclear fluorescence (Data not presented). Monitoring stem phloem and leaf veins of N. benthamiana plants infiltrated with CTV33-Δ13-BYbJunN-GbFosC-76 seven weeks after infiltration revealed fluorescence of the vascular tissue indicating the ability of this construct to systemically infect upper leaves of N. benthamiana (FIG. 16B).

Insertion Between p23 and 3'NTR.

The next step was to examine expression of the two genes when positioned closer to the 3' terminus. The two gene components of the BiFC system were introduced into CTV433 behind p23 (between nts #19020 and 19021), CTV33-23-BYbJunN-GbFosC-59 (FIG. 3-17A). Upon RNA transfection of construct CTV33-23-BYbJunN-GbFosC-59, nuclear fluorescence of infected protoplast was observed under the fluorescent microscope. However, it was difficult to pass the new construct from one protoplast batch to another, similar to GUS and the GFP/Pro/GUS fusion genes inserted at the same location. Upon agro-infiltration of N. benthamiana plants with CTV33-23-BYbJun-GbFosC-59 in full length CTV, fluorescence was observed in infiltrated areas. Systemic symptoms similar to that expected for infection of N. benthamiana by CTV was extremely delayed. However, monitoring upper non-inoculated leaves and phloem tissue of the stem at seven weeks after agro-infiltration of leaves revealed fluorescence of nuclei of the vascular tissue, demonstrating systemic infection by the vector (FIG. 17C). These results confirmed by ELISA, indicate that the position between p23 and 3'NTR can accommodate two extra genes without affecting the ability of CTV to systemically invade the plants Similar to both genes replacing p13 in construct CTV33-Δ13-BYbJunN-GbFosC-76 there was a delay in the time frame of colonizing the upper vascular tissues by construct CTV33-23-BYb-JunN-GbFosC-59. Nuclear fluorescence of systemic stem phloem tissue indicates that CTV33-Δ13-BYbJunN-Gb-FosC-76 infected more cells than construct CTV33-23-BYbJunN-GbFosC-59 (FIG. 16B & FIG. 17C). This difference in the number of cells infected indicates the better ability of CTV33-Δ13-BYbJunN-GbFosC-76 to move in N. benthamiana as compared to CTV33-23-BYbJunN-GbFosC-59.

Example 6: Expression of Multiple Foreign Genes Simultaneously from Different Locations To express multiple foreign genes from two different positions, the inventors elected to replace the p13 gene and insert a second gene behind p23. CTV33-Δ13-BYbJunN-23-GbFosC-67 (FIG. 17A) was created via replacement of the p13 gene with the BYSV CP-CE driving the bJunN ORF and the GLRaV-2 CP-CE controlling the bFosC ORF inserted between the p23 ORF and the 3'NTR. CTV33-Δ13-BYbJunN-23-GbFosC-67 was transfected into protoplasts and Northern blot analysis revealed the replication of the virus (FIG. 17B). However, accumulation of the p23 mRNA was greatly reduced. CTV33-Δ13-BYbJunN-23-GbFosC-67 was agro-inoculated into N. benthamiana. The infiltration into the leaves indicated nuclear fluorescence of infected cells (FIG. 17C) which were much fewer in number compared to constructs CTV33-Δ13-BYbJunN-GbFosC-76 and CTV33-23-BYbJunN-GbFosC-59. Isolation of virions from leaves and transfection of protoplast was carried out resulting in nuclear fluorescence of infected protoplast indicating the successful formation of biologically active virions. However, systemic infection was not achieved in N. benthamiana as indicated by the lack of nuclear fluorescence in the stem and upper non-inoculated leaves of N. benthamiana and confirmed by ELISA.

In order to further study simultaneous multiple gene expression from the different locations as above, CTV33-Δ13-BYGUS-23-GGFP-71 was engineered such that the GUS ORF under the control of the BYSV CP-CE replaced the p13 gene (nts 17292-17582) and the GFP ORF under the control of the GLRaV-2 CP-CE was inserted between the p23 and 3'NTR (nts 19020 and 19021)(FIG. 18A). RNA transcripts of CTV33-Δ13-BYGUS-23-GGFP-71 were transfected into N. benthamiana protoplasts and northern blot analysis indicated efficient replication of the construct in protoplasts (FIG. 18B). Leaf infiltration of N. benthamiana plants with construct CTV33-Δ13-BYGUS-23-GGFP-71 resulted in replication of the virus as indicated by visible fluorescence under a UV light and by GUS activity (Data not presented). The agro-inoculated plants began to exhibit GUS activity and fluorescence in the upper non-inoculated leaves 6 weeks after infiltration (FIG. 3-18C). The systemic infection of upper leaves was slightly slower than constructs with only GFP alone. Also, the phenotype of vein clearing followed by necrosis associated with CTV infection of N. benthamiana vascular tissue occurred later than that of single gene vectors. The level of fluorescence when observed UV light appeared to be slightly less than that of the single gene constructs. However, the GFP fluorescence was more in plants infected with construct CTV33-Δp13BYGUS-23GGFP-71, which was controlled by its own CE, compared to that of the fusion in constructs (CTV33-23-BY-GFP-HC-GUS-51, CTV33-23-BY-GFP-NIa-GUS-52, CTV33-23-G-GFP-HC-GUS-53, CTV33-23-G-GFP-NIa-GUS-54, CTV33-Δ13-BYGFP-HC-GUS-77 and CTV33-Δ13-BYGFP-NIa-GUS-78). The activity of both genes continued until the death of the N. benthamiana plants. Similarly, in citrus the expression of both genes were better than the same genes in constructs CTV33-Δ13-BYGFP-NIa-GUS-78 and CTV33-23-BY-GFP-HC-GUS-51.

Example 7: Level of Foreign Gene Expression of the Different Constructs in Citrus It is difficult to directly compare foreign gene expression from the different vectors in citrus due to the differences in the times of infection, the ages of the tissue and the effects of the inserted foreign gene cassette on the replication of the virus. Yet, protein presence in citrus is the best measure of expression level. Thus, western blot analysis was used to compare the relative level of expression of the different GFP and GUS constructs in citrus to that of CP protein, a house keeping gene to determine the replication levels. Western blots using the GFP antibodies and the CP antibody revealed a trend which confirms the relative higher expression levels near the 3' end of the genome and a lower expression level when the inserted gene is moved further away from the 3' end with the exception for the insertion between p13 and p20 (FIG. 19A). In contrary, the GUS expression in citrus revealed a higher relative expression level as replacement of p13 rather than insertion behind p23 (FIG. 19B).

Example 8: Multiple Gene Vectors

Plasmid Construction:
Three and four gene vectors were developed by introducing different combination of gene cassettes into the CTV genome at different locations. Three of the vectors were developed in CTV9RΔp33 in the pCAMBIA 1380 background (CTV33-BGFP-BYGUS-GTMVCP-79, CTV33-BGFP-GbFosC-BYbJunN-81 and CTV33-Δ13-BGFP-BY-bJunN-GbFosC-82). The other three three gene vectors (CTV-BASL-BYPTA-CP7-119, CTV-BASL-BYP10-CP7-131, CTV-BASL-BYPTA-CP10-120 and CTV-BRFP-BYGFP-CTMVCP-117) and one four gene vector (CTVΔ13-BRFP-GbFosC-BYbJunN-CTMVCP-118) were developed by modifying CTV9R in the background of pCAMBIA1380 altered by replacing the hygromycin ORF with the p22 ORF of Tomato chlorosis virus. For the ease of cloning the PstI restriction site in p33 ORF in full length CTV9R was eliminated by introducing a silent mutation using overlap extension PCR using primers 1749 and 1750 in combination with primer C-1436 and C-253 followed by digestion of both the overlap PCR product and CTV9R with XmaI and PmeI. Most of the gene cassettes were introduced into their locations by overlap extension PCR using the primers listed in tablet. The only exception was the insertion of green fluorescent protein cycle 3 in between the CPm and CP gene. Introducing the GFPC3 gene cassette into that location was done by restriction digestion of 9-47RGFP plasmid and point mutated CTV9R in pCAMBIA1380 with PmeI and PstI.

Expression of Three and Four Foreign Genes Simultaneously

After successfully expressing two genes in N. benthamiana and citrus with one and two different controller elements we are building vectors to express three and four foreign genes from three and four different controller elements, respectively. The reporter genes used in different combinations were the green fluorescent protein (cycle 3 GFP, GFPC3), red fluorescent protein (tag red fluorescent protein, RFP), Bimolecular fluorescence complementation using the bFos and bJun mammalian transcription factors (Hu et al., 2002), β-glucuronidase (GUS) gene from *Escherichia coli* and the Tobacco mosaic virus (TMV) coat protein gene (CP). Similarly, three gene vectors were built in different combinations to express two antimicrobial peptides (AMPs) from *Tachypleus tridentatus* and *Sus scorfa*, *Allium sativum* lectin (ASL) and *Pinellia ternata* agglutinin (PTA). The three gene vectors were either expressed from two or three locations within the CTV genome Expression of Three Foreign Genes from Three Different Locations Simultaneously:

Six vectors were built to express three foreign genes from three different locations. The vectors were built to express the genes either from CTV9RΔp33 or full length CTV9R.

Vectors Built to Express Three Genes from Three Different Locations in CTV9RΔp33

Two vectors were built by inserting the three extra gene cassettes into CTV9RΔp33 creating expression vectors CTV33-BGFP-BYGUS-GTMVCP-79 (FIG. 26) and CTV33-Δ13-BGFP-BYbJunN-GbFosC-82 (FIG. 28). CTV33-BGFP-BYGUS-GTMVCP-79 expresses the three ORFs of GFP (insertion between CPm and CP), GUS (insertion between p13 and p20) and the coat protein of TMV (insertion between p23 and 3'UTR) under the CP-CE of BYV, BYSV and GLRaV-2, respectively. CTV33-Δ13-BGFP-BYbJunN-GbFosC-82 expresses the three ORFs of GFP (insertion between CPm and CP), bJunN ORF (replacement of p13) and bFosC (insertion between p23 and 3'UTR) under the CP-CE of BYV, BYSV and GLRaV-2, respectively. The two vectors were infiltrated into *N. benthamiana* leaves in combination with silencing suppressors and inoculated into citrus using the procedure of Gowda et al., 2005. As leaves were cut and grinded to isolate virions over 70% sucrose cushion gradient just 5 days after infiltration into the *N. benthamiana* leaves it was not likely that these plants will get systemically infected, thus they were discarded. The fluorescence of infiltrated leaves under hand held UV indicated the expression of the GFP protein in both CTV33-BGFP-BYGUS-GTMVCP-79 and CTV33-Δ13-BGFP-BYbJunN-GbFosC-82 indicating the ability of the created vector to replicate in the *N. benthamiana* leaves. Electron microscope grids prepared from leaf dips of infiltrated *N. benthamiana* leaves for construct CTV33-BGFP-BYGUS-GTMVCP-79 and CTV33-Δ13-BGFP-BYbJunN-GbFosC-82 indicated the formation of virions a prerequisite for the successful mechanical inoculation of citrus seedlings with CTV. Furthermore, in the case of CTV33-BGFP-BYGUS-GTMVCP-79 and not CTV33-Δ13-BGFP-BYbJunN-GbFosC-82 there was the formation of rod-shaped structures referred to as TMV pseudo-virions a characteristic of the expression of the TMV coat protein.

Vectors Built to Express Three Genes from Three Different Locations in CTV9R

Four vectors were built to express three foreign genes from the same three different locations within the CTV genome. The three locations selected were insertion between CPm and CP, p13 and p20 and p23 and 3'UTR. For the ease of cloning into the full length CTV infectious clone a the PstI site within the p33 ORF was eliminated by introducing a silent point mutation by overlap extension PCR. Three of the four vectors were created by using different combinations of the two AMPs, ASL and PTA resulting in expression vectors CTV-BASL-BYPTA-CP7-119, CTV-BASL-BYP10-CP7-131 and CTV-BASL-BYPTA-CP10-120. The fourth vector named CTV-BRFP-BYGFP-CTMVCP-117 was created by inserting the ORFs of GFP, RFP and TMV CP under the control of BYV, BYSV and duplicated CP-CE of CTV. All the vectors were infiltrated into *N. benthamiana* to monitor the development of systemic infection. CTV-BASL-BYPTA-CP7-119 developed efficient systemic infection in 1 *N. benthamiana* plant. Plants infiltrated with vector CTV-BRFP-BYGFP-CTMVCP-117 revealed fluorescence in systemic leaves under hand held UV. Upon development of pronounced systemic infection, virions from CTV-BRFP-BYGFP-CTMVCP-117 will be concentrated over a sucrose step gradient and a sucrose cushion in order to inoculate citrus plants similar to the procedure recently followed for vector CTV-BASL-BYPTA-CP7-119

Expression of Three Foreign Genes from Two Different Locations Simultaneously:

Two vectors were created for the simultaneous expression of three genes from two different locations within the CTV genome. One vector was built in CTV9RΔp33 creating expression vector CTV33-BGFP-GbFosC-BYbJunN-81 whereas the other vector was built in full length CTV9R named CTVΔ13-GbFosC-BYbJunN-CTMVCP-129.

Vector Built to Express Three Genes from Two Different Locations in CTV9RΔp33

CTV33-BGFP-GbFosC-BYbJunN-81 (FIG. 27) was engineered through modifying CTV9RΔp33 by inserting a single gene cassette between CPm and CP (GFP ORF under the control of BYV CP-CE) and a double gene cassette (bFosC ORF followed by bJunN ORF under the control of GLRaV-2 and BYSV CP-CE, respectively) as an insertion between p23 and 3'UTR. A 1:1 mixture of 4 different silencing suppressors and CTV33-BGFP-GbFosC-BYbJunN-81 were infiltrated into *N. benthamiana* leaves. Electron microscopy from grids of leaf dips revealed the formation of virions similar to constructs CTV33-BGFP-BYGUS-GTMVCP-79 and CTV33-Δ13-BGFP-BYbJunN-GbFosC-82. In addition, the infiltrated leaves revealed strong fluorescence under hand held UV light. Infiltrated leaves were used to concentrate virions on a 70% sucrose cushion in an attempt to infect citrus seedlings.

Vector Built to Express Three Genes from Two Different Locations in CTV9R

CTV9R was modified by inserting a double gene cassette (bFosC ORF followed by bJunN ORF under the control of GLRaV-2 and BYSV CP-CE, respectively) as replacement of p13 and a gene cassette (TMV CP ORF under the control of the duplicated CP-CE) as an insertion between p23 and 3'UTR creating expression vector CTVΔ13-GbFosC-BYbJunN-CTMVCP-129 (FIG. 21). This vector is recently infiltrated into *N. benthamiana* leaves. After systemic infection of *N. benthamiana* the virions will be concentrated to enable the inoculation of citrus plants.

Expression of Four Foreign Genes from Three Different Locations Simultaneously:

In order to build the four gene vector we used four gene cassettes located at three different locations within the CTV genome. The RFP ORF was introduced between CPm and CP under the control of the BYV CP-CE, the two BiFC components bFosC and bJunN under the control of GLRaV-2 and BYSV respectively were introduced as a replacement of the p13 gene and the TMV ORF under the control of the duplicated CP-CE of CTV was introduced behind p23. The four gene vector named CTVΔ13-BRFP-GbFosC-BYbJunN-CTMVCP-118 was infiltrated into the *N. benthamiana* leaves for the development of systemic infection. Upon systemic infection virion concentration will be carried out over a sucrose step gradient and cushion for the infection of the citrus trees.

Discussion Related to Examples 1-8

In this work, CTV constructs that are extraordinarily permissive in allowing insertion of foreign sequences at different places in the 3' portion of the genome are disclosed. Numerous different potential vector constructs to express foreign genes via additional subgenomic RNAs, di-cistronic mRNAs, or protease processing of fusion proteins were created and examined. Remarkably, most of these constructs functioned as vectors. Additionally, that the CTV constructs disclosed herein are capable of simultaneously producing large amounts of multiple foreign proteins or peptides.

The ultimate goal was to develop high expressing and stable vectors for the natural CTV host, citrus. Thus, virions were concentrated from *N. benthamiana* plants infected with 12 different constructs that spread and expressed moderate to high levels of the foreign protein(s) and used to inoculate citrus. *C. macrophylla* plants became positive for infection between 6-60 weeks after inoculation depending on the insert length in the virus and the amount of virions concentrated from the *N. benthamiana* leaves that were used for inoculation. Most of the constructs that infected citrus produced moderate levels of the reporter gene/s.

Several approaches were examined for expression of foreign genes from CTV. The first approach was the "add-a-gene" strategy that involved the addition or duplication of a controller element and an additional ORF, which resulted in an additional subgenomic RNA. The "add-a-gene" approach was developed initially in TMV via duplicating the CP subgenomic promoter controlling a foreign gene (Dawson et al., 1989; Donson et al., 1991; Shivprasad et al., 1999). An advantage of this strategy is that it expresses the exact protein with no additional amino acids added to the N or/and C terminus which could affect its biological activity, at relatively high levels. However, there are limitations of this strategy that should be considered. Duplication of the controller element can lead to homologous recombination resulting in the loss of the gene of interest (Chapman et al., 1992; Dawson et al., 1989). Although this made the TMV insert unstable, it appeared to have little effect on the stability in CTV (Folimonov et al., 2007). The use of a heterologous controller element from related viruses stabilized the TMV insertions. However, heterologous controller elements usually are differentially recognized by the replicase complex of the virus (Folimonov et al., 2007; Shivprasad et al., 1999). This observation can be utilized to regulate the levels of desired gene expression (Shivprasad et al., 1999). An important consideration is that there can be competition between the different subgenomic RNAs of a virus. With TMV, the extra gene competed with the coat protein gene and the movement gene. There appeared to be a maximal capacity for production of subgenomic RNAs that was divided among the three RNAs. Manipulations that resulted in increases in one resulted in decreases in the others. One solution was to reduce coat protein production to allow optimal foreign gene and movement gene expression (Shivprasad et al., 1999; Girdishivelli et al., 2000). Yet, CTV subgenomic mRNAs appeared to be much less competitive (Folimonov et al., 2007; Ayllón et al., 2003).

In previous work, a CTV vector was created that expressed an extra gene between the CP and CPm genes that was an effective and stable vector in citrus trees. The foreign gene was in position 6 from the 3' terminus (Folimonov et al., 2007). The position of the extra gene was chosen arbitrarily. Here the inventors continued vector design in an attempt to define the limits of manipulation of the CTV genome in producing extra proteins or peptides. The virus expresses its ten 3' genes via sg mRNAs (Hilf et al., 1995). One rule of CTV gene expression is that genes nearer the 3' terminus are transcribed higher than internal genes. For example, transcription of the p33 gene, which is at position 10 from the 3' terminus, is very low in its native position, but transcription became very high when the p33 gene was moved near the 3' terminus (Satyanarayana et al., 1999). Thus, expression of foreign genes from positions nearer the 3' terminus might result in higher levels than from the position 6 arbitrarily chosen in the first vector (Folimonov et al., 2007). Yet, based on results from other viruses, only certain positions within the viral genome are likely to tolerate extra gene insertions. For example, with TMV or Alfalfa mosaic virus the location between CP and 3'NTR did not accommodate an insert (Dawson et al., 1989; Lehto and Dawson, 1990; Sanchez-Navarro et al., 2001). Remarkably, almost all of the constructs with insertions in CTV within the p13 deletion, between p13 and p20, and between p23 and the 3' NTR were viable. In contrast, it was found that the only position the virus did not tolerate insertions was between the p20 and p23 genes. It is possible that these insertions interfered with the transcription of either of the adjacent genes.

Another strategy to express foreign genes in a viral vector consists of in-frame fusion of an ORF of interest to a viral ORF at either the N or C terminus. The two proteins can be released by engineering a protease and processing sites between the two proteins (Dolja et al., 1997; Gopinath et al., 2000). It was first adapted in the potyviridae, tobacco etch virus (Dolja et al., 1992). The major advantage of polyprotein fusion strategy is that the foreign protein is expressed in 1:1 ratio with the viral protein. A major limitation is that this process adds extra amino acids at the N and/or C termini of both proteins, which may affect their biological activities.

A series of constructs utilizing the HC-Pro or NIa proteases from potyviruses to enable post translational processing of the engineered polyprotein to release free GFP, protease, and the p23 protein were created. These vectors were able to systemically infect *N. benthamiana*. The systemic movement of these constructs was slower than the expression vector constructs containing only the GFP ORF as an extra gene. The slower systemic movement and the lower levels of GFP expression in the systemic leaves partially could be attributed to the extra C-terminal amino acids of p23 reduced its activity in RNA silencing suppression or amplification of viral RNAs or the protease processing delayed its activity. Although these constructs did not produce the maximal levels of foreign protein, they were viable vectors expressing substantial amounts of GFP.

Upon identifying the locations within the CTV genome that could accommodate foreign gene inserts, strategies were designed to construct viral vectors that express multiple genes. The first strategy depended on the use of a single controller element driving the transcription of a polypeptide gene. The fusion gene that consisted of GFP/Pro/GUS, ranged in size from 3127 nts to 3480 nts. Other strategies utilized two extra CEs to produce two extra sg RNAs simultaneously. This strategy gave the flexibility to insert the two genes in tandem in the same location or in two different locations. Both strategies worked.

Heterologous protein expression in whole plant is usually accomplished by development of transgenic plants by insertion of foreign DNA into the plastid or nuclear genome. Plastid transformation has been successful for only a few annual crops. Time and success of nuclear transformation varies among the different crops. Certain plants are more recalcitrant to transformation and subsequent regeneration than others. There are other disadvantages, particularly in perennial crops. For example, citrus has a long juvenile stage after regeneration that prolongs the time necessary to evaluate the horticultural characteristics and delays the time to commercial use. Another major disadvantage is that transformation is limited to the next generation of plants.

The inventors have now developed a series of different CTV vectors, each with different characteristics that are more effective under specific conditions. For example, with the "add-a-gene" vectors, the inventors would advocate the expression of a small gene in 3' of the p23 gene in CTV for maximal expression. A medium gene could be more efficiently expressed from within the p13 area. A large gene probably would be better accommodated as an insertion between CP and CPm where it would disrupt the viral subgenomic RNAs less and result in better systemic invasion of the plant. For expression of smaller proteins, peptides, or RNAs to target RNA silencing, it is possible that the virus could accommodate 3 or 4 different genes. Different combinations of extra sg RNAs and protease processing can be chosen. Although two foreign proteins have been produced from other viruses, CTV is unique in usefulness because of its stability. The original vector has been continuously producing GFP for 8 years.

The uses of the CTV based expression vector have evolved since its inception. It was initially developed as a laboratory tool for citrus improvement. The vector was designed to express potential genes for transformation of citrus. Results of the effect of the heterologous gene in citrus, particularly if the effect was expected in mature tissue or fruit, could be obtained by the virus years before results would come from direct transformation. However, conditions and needs of the citrus industry have changed due to the invasion of a new bacterial disease referred to as Huanglongbing (HLB). This disease has spread so rapidly and is so damaging that the survival of the citrus industry is threatened. Initially, the CTV vector was used to identify antimicrobial peptides with activity against the HLB bacterium for transformation into citrus. However, the disease is spreading so rapidly that transgenic plants may not be available in time to save the industry. Due to the remarkable stability, the CTV vector now is being considered for use in the field to protect citrus trees and to treat infected trees until resistant transgenic plants become available. The CTV vector as a tool in the field to fight an invading disease of citrus is only one example of what viral vectors can do for agriculture. The possibilities are many for very stable vectors like those of CTV and perennial crops, particularly trees. Many trees are productive for 100 years or more. During the lifespan of the trees technologies changes and disease and pest pressures change. To improve trees by traditional transformation methods requires removing all of the present trees from the field and replanting. The use of a viral vector could add new genes to the existing trees.

LIST OF REFERENCES RELATED TO EXAMPLES 1-8

Ahlquist, P., French, R., Janda, M., Loesch-Fries, L. S., 1984. Multi component RNA plant virus infection derived from cloned viral cDNA. Proc. Natl. Acad. Sci. USA 8, 7066-7070.

Akbergenov, R., Zhanybekova, S., Kryldakov, R. V., Zhigailov, A., Polimbetova, N. S., Hohn, T., Iskakov, B. K., 2004. ARC-1, a sequence element complementary to an internal 18S rRNA segment, enhances translation efficiency in plants when present in the leader or intercistronic region of mRNAs. Nucleic Acids Res. 32, 239-247.

Allison, R. F., Dougherty, W. G., Parks, T. D., Willis, L., Johnston, R. E., Kelly, M., Armstrong, F. B., 1985. Biochemical analysis of the capsid protein gene and capsid protein of tobacco etch virus: N-terminal amino acids are located on the virion's surface. J. Virol. 147, 309-316.

Andrade, M., Sato, M., Uyeda, I., 2007. Two resistance modes to Clover yellow vein virus in pea characterized by a green fluorescent protein-tagged virus. Phytopathology 97, 544-550.

Ayllón, M. A., Gowda, S., Satyanarayana, T., Karasev, A. V., Adkins, S., Mawassi, M., Guerri, J., Moreno, P., Dawson, W. O., 2003. Effects of modification of the transcription initiation site context on citrus tristeza virus subgenomic RNA synthesis. J. Virol. 77, 9232-9243.

Balvay, L., Soto Rifo, R., Ricci, E. P., Decimo, D., Ohlmann, T., 2009. Structural and functional diversity of viral IRESes. Biochim. Biophys. Acta 1789, 542-557.

Baulcombe, D. C., Chapman, S., Santa Cruz, S., 1995. Jellyfish green fluorescent protein as a reporter for virus infections. Plant J. 7, 1045-1053.

Beauchemin, C., Bougie, V., Laliberté, J. F., 2005. Simultaneous production of two foreign proteins from a potyvirus-based vector. Virus Res. 112, 1-8.

Brisson, N., Paszkowski, J., Penswick, J. R., Gronenborn, B., Potrykus, I., Hohn, T., 1984. Expression of a bacterial gene in plants by using a viral vector. Nature 310, 511-514.

Cañizares, C. M., Navas-Castillo, J., Moriones, E., 2008. Multiple suppressors of RNA silencing encoded by both genomic RNAs of the crinivirus, Tomato chlorosis virus. Virology 379, 168-174.

Cañizares, M. C., Nicholson, L., Lomonossoff, G. P., 2005 Use of viral vectors for vaccine production in plants. Immunol. Cell Biol. 83, 263-270.

Canto, T., Prior, D. A. M., Hellwald, K.-H., Oparka, K. J., Palukaitis, P., 1997. Characterization of cucumber mosaic virus IV. Movement protein and coat protein are both essential for cell-to-cell movement of cucumber mosaic virus. Virology 237, 237-248.

Carrasco, P., Daros, J. A., Agudelo-Romero, P., Elena, S. F., 2007. A real-time RT-PCR assay for quantifying the fitness of tobacco etch virus in competition experiments. J. Virol. Methods 139, 181-188.

Carrington, J. C., Cary, S. M., Parks, T. D. and Dougherty, W. G., 1989. A second proteinase encoded by a plant potyviral genome. EMBO J. 8, 365-370.

Carrington, J. C., Dougherty, W. G., 1988. A viral cleavage site cassette: Identification of amino acid sequences required for tobacco etch virus polyprotein processing. Proc. Natl. Acad. Sci. USA 85, 3391-3395.

Chalfie, M., Tu, Y., Euskirchen, G., Ward, W. W., Prasher, D. C., 1994. Green fluorescent protein as a marker for gene expression. Science 263, 802-805.

Chapman, S., Kavanagh, T., Baulcombe, D., 1992. Potato virus X as a vector for gene expression in plants. Plant J. 2, 549-557.

Chiba, M., Reed, J. C., Prokhnevsky, A. I., Chapman, E. J., Mawassi, M., Koonin, E. V., Carrington, J. C., Dolja, V. V., 2006. Diverse suppressors of RNA silencing enhance agroinfection by a viral replicon. Virology 346, 7-14.

Crameri, A., Whitehorn, E. A., Tate, E., Stemmer, W. P., 1996. Improved green fluorescent protein by molecular evolution using DNA shuffling. Nat. BioTechniques 14, 315-319.

Dawson, W. O., Bubrick, P., Grantham, G. L. 1988. Modifications of the tobacco mosaic virus coat protein gene affect replication, movement, and symptomatology. Phytopathology 78, 783-789.

Dawson, W. O., Lewandowski, D. J., Hilf, M. E., Bubrick, P., Raffo, A. J., Shaw, J. J., Grantham, G. L. Desjardins, P. R., 1989. A tobacco mosaic virus-hybrid expresses and loses an added gene. Virology 172, 285-292.

Deleris, A., Gallego-Bartolome, J., Bao, J., Kasschau, K. D., Carrington, J. C., Voinnet, O., 2006. Hierarchical action and inhibition of plant Dicer-like proteins in antiviral defense. Science 313, 68-71.

Dietrich, C., Maiss, E., 2003. Fluorescent labeling reveals spatial separation of potyvirus populations in mixed infected Nicotiana benthamiana plants. J. Gen. Virol. 84, 2871-2876.

Dolja, V. V., Hong, J., Keller, K. E., Martin, R. R., Peremyslov, V. V., 1997. Suppression of potyvirus infection by co-expressed closterovirus protein. Virology 234, 243-252.

Dolja, V. V., McBride, H. J., Carrington, J. C., 1992. Tagging of plant potyvirus replication and movement by insertion of beta-glucuronidase into the viral polyprotein. Proc. Natl Acad. Sci. USA 89, 10208-10212.

Donson, J., Kearney, C. M., Hilf, M. E., Dawson, W. O. 1991. Systemic expression of a bacterial gene by a tobacco mosaic virus-based vector. Proc. Natl. Acad. Sci. USA. 88, 7204-7208.

Dorokhov, Y. L., Skulachev, M. V., Ivanov, P. A., Zvereva, S. D., Tjulkina, L. G., Merits, A., Gleba, Y. Y., Hohn, T., Atabekov, J. G., 2002. Polypurine (A)-rich sequences promote cross-kingdom conservation of internal ribosome entry. Proc. Natl. Acad. Sci. USA. 99, 5301-5306.

Edelstein, M. L., Abedi, M. R. Wixon, J., 2007. Gene therapy clinical trials worldwide to 2007—an update. J. Gene Med. 9, 833-842.

Fernandez-Miragall, O., Lopez de Quinto, S., Martinez-Salas, E., 2009. Relevance of RNA structure for the activity of picornavirus IRES elements. Virus Res. 139, 172-182.

Fitzgerald, K. D., Semler, B. L., 2009. Bridging IRES elements in mRNAs to the eukaryotic translation apparatus. Biochim. Biophys. Acta 1789, 518-528.

Folimonov, A. S., Folimonova, S. Y., Bar-Joseph, M., Dawson, W. O., 2007. A stable RNA virus-based vector for citrus trees. Virology 368, 205-216.

Folimonova, S. Y., Folimonov, A. S., Tatineni, S., Dawson, W. O., 2008. Citrus tristeza virus: survival at the edge of the movement continuum. J. Virol. 82, 6546-6556.

Folimonova, S. Y., Robertson, C. J., Shilts, T., Folimonov, A. S., Hilf, M. E., Garnsey, S. M. Dawson, W. O., 2010. Infection with strains of Citrus tristeza virus does not exclude super infection by other strains of the virus. J. Virol. 84, 1314-1325.

French, R., Janda, M., Ahlquist, P., 1986. Bacterial gene inserted in an engineered RNA virus: efficient expression in monocotyledonous plant cells. Science 231, 1294-97

Fütterer, J., Bonneville, J. M., Hohn, T., 1990. Cauliflower mosaic virus as a gene expression vector for plants. Physiol. Plant. 79, 154-157.

Gallie, D. R. 2001. Cap-independent translation conferred by the 5' leader of tobacco etch virus is eukaryotic initiation factor 4G dependent. J. Virol. 75, 12141-12152.

Gallie, D. R., Tanguay, R. L., Leathers, V., 1995. The tobacco etch viral 5' leader and poly(A) tail are functionally synergistic regulators of translation. Gene 165, 233-238.

Garnsey, S. M., Gonsalves, D., Purcifull, D. E., 1977. Mechanical transmission of citrus tristeza virus. Phytopathology 67, 965-968.

Garnsey, S. M., Cambra, M., 1991. Enzyme-linked immunosorbent assay (ELISA) for citrus pathogens. In: Roistacher, C. N. (Ed.), Graft-Transmissible Diseases of Citrus, Handbook for Detection and Diagnosis. FAO, Rome, pp. 193-216.

Garnsey, S. M., Henderson C. T., 1982. Extraction, centrifugation, and assay techniques for purification of intact citrus tristeza virus. Workshop on Plant Virus Detection, Agric. Exp. Stn., University of Puerto Rico, Rio Piedras, Mar. 29-Apr. 2, 1982, 106-112.

Giritch, A., Marillonnet, S., Engler, C., van Eldik, G., Botterman, J., Klimyuk, V., Gleba, Y., 2006. Rapid high-yield expression of full-size IgG antibodies in plants coinfected with noncompeting viral vectors. Proc. Natl. Acad. Sci. USA 103, 14701-14706.

Gleba, Y., Klimyuk, V., Marillonnet, S., 2007. Viral vectors for the expression of proteins in plants. Curr. Opin. Biotechnol. 18, 134-141.

Gopinath, K., Wellink, J., Porta, C., Taylor, K. M., Lomonossoff, G. P., van Kammen, A., 2000. Engineering cowpea mosaic virus RNA-2 into a vector to express heterologous proteins in plants. Virology 267, 159-173.

Gowda, S., Satyanarayana, T., Ayllon, M. A., Albiach-Marti, M. R., Mawassi, M., Rabindran, S., Garnsey, S. M., Dawson, W. O., 2001. Characterization of the cis-acting elements controlling subgenomic mRNAs of citrus tristeza virus: production of positive- and negative-stranded 3'-terminal and positive-stranded 5'-terminal RNAs. Virology 286 1, 134-151.

Gowda, S., Satyanarayana, T., Davis, C. L., Navas-Castillo, J., Albiach-Marti, M. R., Mawassi, M., Valkov, N., Bar-Joseph, M., Moreno, P., Dawson, W. O., 2000. The p20 gene product of Citrus tristeza virus accumulates in the amorphous inclusion bodies. Virology 274, 246-254.

Gowda, S., Satyanarayana, T., Robertson, C. J., Garnsey, S. M., Dawson, W. O., 2005. Infection of citrus plants with virions generated in Nicotiana benthamiana plants agroinfiltrated with a binary vector based Citrus tristeza virus, p. 23-33. In M. E. Hilf, N. Duran-Vila, and M. A. Rocha-Peña (eds.), Proceedings of the 16th Conference of the International Organization of Citrus Virologists. IOCV, Riverside, Calif., 728 USA.

Grdzelishvili, V. Z., Chapman, S. N., Dawson, W. O., Lewandowski, D. J., 2000. Mapping of the Tobacco mosaic virus movement protein and coat protein subgenomic RNA promoters in vivo. Virology 275, 177-192.

Gronenborn, B., Gardner, R. C., Schaefer, S., Shepherd, R. J., 1981. Propagation of foreign DNA in plants using cauliflower mosaic virus as vector. Nature 294, 773-76.

Hagiwara, Y., Peremyslov, V. V., Dolja, V. V., 1999. Regulation of closterovirus gene expression examined by insertion of a self-processing reporter and by northern hybridization. J. Virol. 73, 7988-7993.

Hilf, M. E., Karasev, A. V., Pappu, H. R., Gumpf, D. J., Niblett, C. L., Garnsey, S. M., 1995. Characterization of citrus tristeza virus subgenomic RNAs in infected tissue. Virology 208, 576-582.

Horton, R. M., Hunt, H. D., Ho, S. N., Pullen, J. R., Pease, L. B., 1989. Engineering hybrid genes without the use of restriction enzymes: gene splicing by overlap extension. Gene 77, 61-68.

Hu, C. D., Chinenov, Y., Kerppola, T. K., 2002. Visualization of interactions among bZIP and Rel family proteins in living cells using bimolecular fluorescence complementation. Molecular Cell 9, 789-798.

Ion-Nagy, L., Lansac, M., Eyquard, J. P., Salvador, B., Garcia, J. A., Le Gall, O., Hernould, M., Schurdi-Levraud, V., Decroocq, V., 2006. PPV long-distance movement is occasionally permitted in resistant apricot hosts. Virus Res. 120, 70-78.

Ivanov, P. A., Karpova, O. V., Skulachev, M. V., Tomashevskaya, O. L., Rodionova, N. P., Dorokhov, Y. L., Atabekov, J. G., 1997. A tobamovirus genome that contains an internal ribosome entry site functional in vitro. Virology 232, 32-43.

Karasev, A. V., 2000. Genetic diversity and evolution of closteroviruses. Annu. Rev. Phytopathol. 38, 293-324.

Karasev, A. V., Boyko, V. P., Gowda, S., Nikolaeva, O. V., Hilf, M. E., Koonin, E. V., Niblett, C. L., Cline, K., Gumpf, D. J., Lee, R. F., Garnsey, S. M., Lewandowski, D. J., Dawson, W. O., 1995. Complete sequence of the citrus tristeza virus RNA genome. Virology 208, 511-520.

Karasev, A. V., Nikolaeva, O. V., Mushegian, A. R., Lee, R. F. Dawson, W. O., 1996. Organization of the 3'-terminal half of beet yellow stunt virus genome and implications for the evolution of closteroviruses. J. Virol. 221, 199-207.

Kasschau, K. D., Xie, Z., Allen, E., Llave, C., Chapman, E. J., Krizan, K. A., and Carrington, J. C., 2003. P1/HC-Pro, a viral suppressor of RNA silencing, interferes with *Arabidopsis* development and miRNA function. Dev. Cell 4, 205-217.

Kawakami, S., Watanabe, Y., Beachy, R. N., 2004. Tobacco mosaic virus infection spreads cell to cell as intact replication complexes. Proc. Natl. Acad. Sci. USA 101, 6291-6296.

Kelloniemi, J., Mäkinen, K., Valkonen, J. P. T., 2008. Three heterologous proteins simultaneously expressed from a chimeric potyvirus: infectivity, stability and the correlation of genome and virion lengths. Virus Res. 135, 282-291.

Kneller, E. L., Rakotondrafara, A. M., Miller, W. A., 2006. Cap independent translation of plant viral RNAs. Virus Res. 119, 63-75.

Koh, D. C., Wong, S. M., Liu, D. X., 2003. Synergism of the 3'-untranslated region and an internal ribosome entry site differentially enhances the translation of a plant virus coat protein. J. Biol. Chem. 278, 20565-20573.

Lehto, K., and Dawson, W. O., 1990. Replication, stability, and gene expression of tobacco mosaic virus mutants with a second 30K ORF. Virology 175, 30-40.

Lewandowski, D. J. and Dawson, W. O., 1998. Deletion of internal sequences results in Tobacco mosaic virus defective RNAs that accumulate to high levels without interfering with replication of the helper virus. Virology 251, 427-437.

Lico, C., Chen, Q., Santi, L., 2008. Viral vectors for production of recombinant proteins in plants. J. Cell Physiol. 216, 366-377.

Liu, Y. P., Peremyslov, V. V., Medina, V., Dolja, V. V. 2009. Tandem leader proteases of Grapevine leafroll-associated virus 2: host-specific functions in the infection cycle. Virology 383, 291-299.

López, C., Navas-Castillo, J., Gowda, S., Moreno, P., Flores R., 2000. The 23-kDa protein coded by the 3'-terminal gene of citrus tristeza virus is an RNA-binding protein. Virology 269, 462-470.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc. Natl. Acad. Sci. USA 101, 15742-15747.

Lucy, A. P., Guo, H. S., Li, W. X., Ding, S. W., 2000. Suppression of post-transcriptional gene silencing by a plant viral protein localized in the nucleus. EMBO J. 19, 1672-1680.

Marton, I., Zuker, A., Shklarman, E., Zeevi, V., Tovkach, A., Roffe, S., Ovadis, M., Tzfira, T., Vainstein, A., 2010. Nontransgenic genome modification in plant cells. Plant Physiol. 154, 1079-1087.

Masoumi, A., Hanzlik, T. N., Christian, P. D., 2003. Functionality of the 59- and intergenic IRES elements of cricket paralysis virus in a range of insect cell lines, and its relationship with viral activities. Virus Res. 94, 113-120.

Masuta, C., Yamana, T., Tacahashi, Y., Uyeda, I., Sato, M., Ueda, S., Matsumura, T., 2000. Development of clover yellow vein virus as an efficient, stable gene-expression system for legume species. Plant J. 23, 539-546.

Navas-Castillo, J., Albiach-MartôÂ, M. R., Gowda, S., Hilf, M. E., Garnsey, S. M., Dawson, W. O., 1997. Kinetics of accumulation of citrus tristeza virus RNAs. Virology 228, 92-97.

Niepel, M., Gallie, D. R., 1999. Identification and characterization of the functional elements within the tobacco etch virus 5' leader required for cap-independent translation. J. Virol. 73, 9080-9088.

Padgett, H. S., Epel, B. L., Heinlein, M. H., Watanabe, Y., Beachy, R. N. 1996. Distribution of tobamovirus movement protein in infected cells and implications for cell-to-cell spread of infection. Plant J. 10, 1079-1099.

Pappu, H. R., Karasev, A. V., Anderson, E. J., Pappu, S. S., Hilf, M. E., Febres, V. J., Eckloff, R. M. G., McCaffery, M., Boyko, V., Gowda, S., Dolia, V. V., Koonin, E. V., Gumpf, D. J., Cline, K. C., Garnsey, S. M., Dawson, W. O., Lee, R. F., Niblett, C. L., 1994. Nucleotide sequence and organization of eight 3' open reading frames of the Citrus tristeza closterovirus genome. Virology 199, 35-46.

Peremyslov, V. V., Hagiwara, Y., Dolja, V. V., 1999. HSP70 homolog functions in cell-to-cell movement of a plant virus. Proc. Natl. Acad. Sci. U.S.A. 96, 14771-14776.

Prokhnevsky, A. I., V. V. Peremyslov, V. V., Napuli, A. J., Dolja, V. V., 2002. Interaction between long-distance transport factor and Hsp70-related movement protein of beet yellows virus. J. Virol. 76, 11003-11011.

Ratcliff, F., MacFarlane, S., Baulcombe, D. C., 1999. Gene silencing without DNA: RNA-mediated cross protection between viruses. Plant Cell, 11, 1207-1215.

Roberts, A. G., Santa Cruz, S., Roberts, I. M., Prior, D. A. M., Turgeon, R., Oparka, K. J., 1997. Phloem unloading in sink leaves of *Nicotiana benthamiana*: comparison of a fluorescent solute with a fluorescent virus. Plant Cell 9, 1381-1396.

Roberts, L. O., Groppelli, E., 2009. An atypical IRES within the 50 UTR of a dicistrovirus genome. Virus Res. 139, 157-165.

Robertson, C. J., Garnsey, S. M., Satyanarayana, T., Folimonova, S., Dawson, W. O., 2005. Efficient infection of citrus plants with different cloned constructs of Citrus tristeza virus amplified in *Nicotiana benthamiana* protoplasts. Proc. 16th Conf. IOCV. IOCV, Riverside, Calif., pp. 187-195.

Roy, G., Weisburg, S., Rabindran, S., Yusibov, V., 2010. A novel two-component Tobacco mosaic virus-based vector system for high-level expression of multiple therapeutic proteins including a human monoclonal antibody in plants. Virology 405, 93-99.

Sánchez-Navarro, J. A., Miglino, R., Ragozzino, A., and Bol, J. F., 2001. Engineering of Alfalfa mosaic virus RNA 3 into an expression vector. Arch. Virol. 146, 923-939.

Sato, M., Masuta, C., Uyeda, I., 2003. Natural resistance to Clover yellow vein virus in beans controlled by a single recessive locus. Mol. Plant Microbe Interact. 16, 994-1002.

Satyanarayana, T., Bar-Joseph, M., Mawassi, M., Albiach-Martí, M. R., Ayllón, M. A., Gowda, S., Hilf, M. E., Moreno, P., Garnsey, S. M., Dawson, W. O., 2001. Amplification of Citrus tristeza virus from a cDNA clone and infection of citrus trees. Virology 280, 87-96.

Satyanarayana, T., Gowda, S., Ayllón, M. A., Albiach-Martí, M. R., Dawson, W. O., 2002a. Mutational analysis of the replication signals in the 3'-non translated region of Citrus tristeza virus. Virology 300, 140-152.

Satyanarayana, T., Gowda, S., Ayllón, M. A., Albiach-Marti, M. R., Rabindram, R., Dawson, W. O. 2002b. The p23 protein of Citrus tristeza virus controls asymmetrical RNA accumulation. J. Virol. 76, 473-483.

Satyanarayana, T., Gowda, S., Ayllón, M. A., Dawson, W. O., 2003. Frame shift mutations in infectious cDNA clones of Citrus tristeza virus: a strategy to minimize the toxicity of viral sequences to *Escherichia coli*. Virology 313, 481-491.

Satyanarayana, T., Gowda, S., Ayllón, M. A., Dawson, W. O., 2004. Closterovirus bipolar virion: evidence for initiation of assembly by minor coat protein and its restriction to the genomic RNA 5' region. Proc. Natl. Acad. Sci. USA 101, 799-804.

Satyanarayana, T., Gowda, S., Boyko, V. P., Albiach-Marti, M. R., Mawassi, M., Navas-Castillo, J., Karasev, A. V., Dolja, V., Hilf, M. E., Lewandowski, D. J., Moreno, P., Bar-Joseph, M., Garnsey, S. M., Dawson, W. O., 1999. An engineered closterovirus RNA replicon and analysis of heterologous terminal sequences for replication. Proc. Natl. Acad. Sci. USA 96, 7433-7438.

Satyanarayana, T., Gowda, S., Mawassi, M., Albiach-Marti, M. R., Ayllón, M. A., Robertson, C., Garnsey, S. M., Dawson, W. O., 2000. Closterovirus encoded HSP70 homolog and p61 in addition to both coat proteins function in efficient virion assembly. Virology 278, 253-265.

Shivprasad, S., Pogue, G. P., Lewandowski, D. J., Hidalgo, J., Donson, J., Grill, L. K., Dawson, W. O., 1999. Heterologous sequences greatly affect foreign gene expression in tobacco mosaic virus-based vectors. Virology 255, 312-323.

Siegel, A., 1983. RNA viruses as cloning vehicles. Phytopathology 73, 775.

Siegel, A., 1985. Plant-virus-based vectors for gene transfer may be of considerable use despite a presumed high error frequency during RNA synthesis. Plant Mol. Biol. 4, 327-29.

Takahashi, T., Sugawara, T., Yamatsuta, T., Isogai, M., Natsuaki, T., Yoshikawa, N., 2007. Analysis of the spatial distribution of identical and two distinct virus populations differently labeled with cyan and yellow fluorescent proteins in coinfected plants. Phytopathology 97, 1200-1206

Takamatsu, N., Ishikawa, M., Meshi, T., Okada, Y., 1987. Expression of bacterial chloramphenicol acetyl transferase gene in tobacco plants mediated by TMV-RNA. EMBO J. 6, 307-311.

Tatineni, S., Gowda, S., Dawson W. O., 2010. Heterologous minor coat proteins of Citrus tristeza virus strains affect encapsidation, but the coexpression of HSP70h and p61 restores encapsidation to wild-type levels. Virology 402, 262-270.

Tatineni, S., McMechan A. J., Hein G. L., French R., 2011. Efficient and stable expression of GFP through Wheat streak mosaic virus-based vectors in cereal hosts using a range of cleavage sites: Formation of dense fluorescent aggregates for sensitive virus tracking. Virology 410, 268-281.

Tatineni, S., Robertson, C. J., Garnsey, S. M., Bar-Joseph, M., Gowda, S., Dawson, W. O., 2008. Three genes of Citrus tristeza virus are dispensable for infection and movement throughout some varieties of citrus trees. Virology 376, 297-307.

Toth, R. L., Chapman, S., Carr, F., Santa Cruz, S., 2001. A novel strategy for the expression of foreign genes from plant virus vectors. FEBS Lett. 489, 215-219.

Turpen, T. H., Turpen, A. M., Weinzettl, N., Kumagai, M. H., Dawson, W. O., 1993. Transfection of whole plants from wounds inoculated with *Agrobacterium tumefaciens* containing cDNA of tobacco mosaic virus. J. Virol. Meth. 42, 227-239.

Van Vloten-Doting, L., 1983. Advantages of multiple partite genomes of single-stranded RNA plant viruses in nature, for research and genetic engineering. Plant Mol. Biol. 1, 55-60.

Van Vloten-Doting, L., Bol, J. F., Cornelissen, B., 1985. Plant virus-based vectors for gene transfer will be of limited use because of the high error frequency during viral RNA synthesis. Plant Mol. Biol. 4, 323-326.

Verch, T., Yusibov, V., Koprowski, H., 1998. Expression and assembly of a full-length monoclonal antibody in plants using a plant virus vector. J. Immunol. Methods 220, 69-75.

Verver, J., Wellink, J, Van Lent, J., Gopinath, K., and Van Kammen, A., 1998. Studies on the movement of cowpea mosaic virus using the jellyfish green fluorescent protein. Virology 242, 22-27.

Woolaway, K. E., Lazaridis, K., Belsham, G. J., Carter, M. J., Robert, L. O., 2001. The 5' untranslated region of rhopalosiphum padi virus contains an internal ribosome entry site which functions efficiently in mammalian, plant, and insect translation system. J. Virol. 75, 10244-10249.

Example 9

1. Introduction

Virus-based vectors for expressing foreign genes in plants are routine laboratory tools (Porta and Lomonossoff, 2002 and Gleba et al., 2007), generally developed for short term laboratory experiments in herbaceous plants or for making specialty products in these plants. However, the development of vectors that stably express foreign genes for years has opened up new opportunities in perennial plants (Folimonov et al., 2007, Kurth et al., 2012, Dawson and Folimanova, 2013 and Dolja and Koonin, 2013). Virus-based vectors can be used to modify the existing generation of trees. One such opportunity is the use for field application to protect against disease or to treat infected plants. For example, the rapid spread of devastating disease of citrus, citrus greening also known as huanglongbing (HLB), which is threatening the survival of the citrus industry has changed the Citrus tristeza virus (CTV) vector from a laboratory tool to a potential management strategy for citrus groves (Hodges and Spreen, 2012 and National Research Council, 2010). At this time, the one of the hopes for survival of the Florida citrus industry is the production of resistant or tolerant trees via transgene (http://www.nytimes.com/2013/07/28/science/a-race-to-save-the-orange-by-altering-its-dna.html?pagewanted=all&_r=0). But the time to make, evaluate, and amplify transgenic citrus trees is too long to save the industry. The viral vector can be deployed more quickly and is being considered as an interim approach (National Research Council, 2010).

The HLB disease manifestation requires both the phloem-limited pathogenic bacterium, Candidatus Liberibacter asiaticus (CLas), and phloem feeding Asian citrus psyllid insect vector, Diaphorina citri (Halbert and Manjunath, 2004). The disease can be controlled by suppressing either. Initial efforts have been to control the bacterium, but recent progresses in RNA interference (RNAi) in psyllids provide another possible approach (El-Shesheny et al., 2013, Wuriyanghan and Falk, 2013 and Khan et al., 2013). It is now well-established that double-stranded RNA (dsRNA)-mediated gene silencing mechanism is conserved in many eukaryotes (Geley and Müller, 2004, Gordon and Waterhouse, 2007, Fire, 2007 and Price and Gatehouse, 2008). Plant viral vectors have been utilized in virus-induced gene silencing (VIGS) by exploiting antiviral defense mechanism of the host plants (Ratcliff et al., 1997, Waterhouse et al., 2001 and Lu et al., 2003). The dsRNAs generated by viral RNA polymerases as intermediates during replication specifically are targeted by host defense machinery (Tenllado and Díaz-Ruíz, 2001 and Weber et al., 2006) thus, RNA viruses are inducers as-well-as targets of inherent RNA silencing machinery (Waterhouse et al., 2001). With VIGS vector carrying sequences of host gene, the defense machinery is targeted against the corresponding host mRNAs.

CTV is a member of the genus Closterovirus of the family Closteroviridae, the largest and the most complex plant viral family. Single-stranded RNA genome of ~19.3 kb is encapsidated by two coat proteins (CP) making a long flexuous virions (2000 nm by 10-12 nm) (Bar-Joseph et al., 1979 and Karasev et al., 1995). CTV vector has been shown to be an efficient expression vector capable of expressing more than one foreign gene engineered at different positions in its genome either as extra gene or substitution of some non-essential genes using homologous and heterologous sub-genomic RNA (sgRNA) controller elements (Dawson and Folimanova, 2013 and El-Mohtar and Dawson, 2014). However, plant virus-based vectors are notoriously unstable and tend to revert to wild type, with notable exception of CTV vector which has stably retained a foreign gene for more than a decade in citrus plants (Dawson and Folimanova, 2013). Many of the plant and animal viruses encode one silencing suppressor whereas CTV has been shown to encode three distinct suppressors of RNA silencing (Lu et al., 2004), which potentially protect CTV with such a large RNA genome from antiviral silencing machinery of the perennial woody citrus host. CTV open reading frames (ORFs) p23 and coat protein (CP) suppress the silencing pathway at intra- and inter-cellular level, respectively, while ORF p20, exhibits both at intra- and inter-cellular level silencing (Lu et al., 2004). There were serious concerns whether the CTV-based vector could effectively induce gene silencing. Yet, expression of sequences targeting citrus endogenous phytoene desaturase (PDS) gene by CTV-based vector resulted in photo-bleaching phenotype in citrus, thus demonstrating CTV as a gene silencing vector.

CTV is limited to phloem and phloem-associated cells in citrus trees like CLas bacterium. Since D. citri are phloem feeders, they probe and suck phloem sap and existent alongside including CLas (when feeding on a diseased plant) and there by succor CLas transmission. This coincident cohabitation in the phloem tissue could be exploited to develop a method to combat HLB disease. In our previous study, in vitro topical application of dsRNAs of truncated abnormal wing disc (tAwd) gene to nymphs of D. citri induced wing deformation and reduced survivability in adults, both positively correlated with Awd gene down regulation (El-Shesheny et al., 2013). We hypothesized that; if D. citri could acquire the CLas bacteria from citrus phloem during feeding, it would acquire other components as well present in the phloem sap, such as virions (like virions of phloem limited CTV), virion RNAs, dsRNAs, small RNAs, etc. The objective of this study was to develop a novel method to mitigate HLB disease by controlling its insect vector, D. citri, through CTV-based plant-mediated RNA interference (RNAi). In the present study, gene silencing capabilities of CTV was exploited to express silencing triggers such as dsRNAs (replicative intermediates of both genomic and subgenomic RNAs) and small-interfering RNAs (siRNAs) specific to D. citri endogenous Awd gene in citrus phloem and associated cells. Silencing the Awd gene increased adult mortality and induced malformed wing phenotype which potentially would affect ability of psyllids to vector CLas. CTV-RNAi vector would therefore be relevant for fast-track screening of candidate sequences for RNAi-mediated pest control. By virtue of time, labor and cost, CTV-RNAi could be answer to the slow and difficult citrus transgenic approach in mitigating HLB. Besides it could be a valuable tool in functional genomics studies on citrus.

2. Materials and Methods 2.1. Plant Material

Nicotiana benthamiana plants were grown under controlled growth-room with temperature of 22-24° C., 16/8 h daylight cycle and 60% humidity. One year old seedlings (approximately two feet tall & stem of a pencil thickness) of Alemow (Citrus macrophylla), Duncan grapefruit (C. paradisi) and Sour orange (C. aurantium) were maintained under a controlled greenhouse conditions at Citrus Research and Education Centre, Lake Alfred, Fla.

2.2. Citrus Tristeza Virus (CTV)-Based Vectors

The infectious cDNA clone of Citrus tristeza virus (CTV isolate T36; GenBank accession no. AY170468) in the binary vector pCAMBIA-1380 was used as base plasmid for engineering all the constructs used in this study (Satyanarayana et al., 1999, Satyanayanana et al., 2001, Gowda et al., 2005 and El-Mohtar and Dawson, 2014). This plasmid referred to as wild type, CTV-wt, contained CTV genomic RNA between the duplicated 35S promoter of Cauliflower mosaic virus in the 5' end, a ribozyme sequence of Subterranean clover mottle virus satellite RNA at the 3' end. Unique restriction sites, PacI and StuI were engineered at 5' and 3' end, respectively, to ligate the inserts under coat protein (CP) sub-genomic RNA controller element (CE) between ORF-p23 and 3'-untranslated region.

To clone truncated fragment of green fluorescent protein (GFP) and generate CTV-tGFP, GFP gene coding fragment corresponding to the nts 4-443 of the 30B-GFP-Cycle 3 (Shivprasad et al., 1999) was amplified by SpeedSTAR HS DNA polymerase (Takara Bio. Inc.) using primers GFP-PacI
(5'-CGAGTTAATTAAGCTAGCAAAGGAGAAGAACTTTTCACTG-3')
and GFP-StuI
(5'-GACAAGGCCTGAGTTATAGTTGTACTCGAGTTTGTGTC-3')
&

CTV-GFP (Satyanayanana et al., 2001)

as a template. The PCR product was digested with PacI and StuI restriction enzymes and cloned into similarly digested CTV-wt engineered with CTV CP CE and unique PacI and StuI sites to enable ligation of similarly digested tGFP product.

To clone truncated PDS gene (tPDS) and generate CTV-tPDS vector, primers were designed based on *C. sinensis* PDS gene (Genbank accession no. DQ235261.1). The truncated fragment corresponding to the nucleotides 4-395 of the PDS gene was amplified using total RNA from *C. macrophylla* as a template by SuperScript® III One-Step RT-PCR System with Platinum® Taq DNA Polymerase (Life Technologies Corp.) and primers PDS-PacI
(5'-CGAGTTAATTAAAGCCTTTGCTTCAGCGTTTCTGAAAGTGCTTTC-3')
and PDS-StuI
(5'-GACAAGGCCTGTCTCATACCAGTTCCCGTCCCCATCTTTCC-3').

The PCR product was digested with PacI and StuI restriction enzymes and cloned into similarly digested CTV-tGFP by replacing tGFP with tPDS fragment.

The truncated fragment corresponding to the nucleotides 4-462 of putative abnormal wing disc-like protein (Awd) gene (Genbank accession no. DQ673407.1) of *D. citri* was amplified from the total RNA isolated from the *D. citri* by SuperScript® III One-Step RT-PCR System with Platinum® Taq DNA Polymerase (Life Technologies Corp.) using the primers Awd-PacI
(5'-CGAGTTAATTAAGCCGAACCCAAGGAAAGAACTTTTCTCATG-3')
and Awd-StuI
(5'-GACAAGGCCTTTATTCATAGATCCAGGATTCACTGGCATTTG-3').

The PCR product was digested with PacI and StuI restriction enzymes and cloned into similarly digested CTV-tPDS vector plasmid by replacing tPDS with tAwd fragment.

2.3. Agroinfiltration of CTV Constructs into *N. benthamiana*

Procedures for agroinfiltration of CTV constructs into *N. benthamiana* was followed as described previously (Gowda et al., 2005, Ambrós et al., 2011 and El-Mohtar and Dawson, 2014). ORF p22 silencing suppressor from Tomato chlorosis Crinivirus (ToCV) ligated in place of hygromycin gene was used in the binary vector pCAMBIA1380 to help establish the CTV infection in the infiltrated leaves (El-Mohtar and Dawson, 2014).

2.4. CTV Virion Isolation and Inoculation to Citrus

Systemic leaves from *N. benthamiana* that tested positive for CTV by ELISA, were harvested after 4-6 weeks post infiltration and used to isolate CTV virions for bark-flap inoculation of *C. macrophylla* as described previously (Gowda et al., 2005 and Robertson et al., 2005). An additional ultracentrifugation step at 50,000 rpm for 60 min at 4° C. was carried out in Beckman Optima™ TL 100 to further concentrate the virions.

2.5. Large RNA Northern Blot Hybridization

Total RNA was extracted from 100 mg of *C. macrophylla* tissues using RNeasy Mini Kit (Qiagen) and used in large RNAs Northern hybridizations as described previously (Satyanarayana et al., 1999). The negative-stranded riboprobe with digoxigenin-labeled UTP specific to 3'-untranslated region of CTV genomic RNA (273 nucleotide long) was used for hybridization.

2.6. Small RNA Isolation

Total RNAs were extracted from 1 g of *C. macrophylla* tissue using TRIzol® Reagent (Life Technologies Corp.) and was further purified by extracting 1-2 times with Phenol:Chloroform:IsoAmylAlcohol (25:24:1) (Chomczynski and Sacchi, 1987) and separated into large and small RNA fractions by following mirVana™ miRNA Isolation Kit (Life Technologies Corp.). To enrich small RNAs, the RNA sample was brought to 25% ethanol concentration. The lysate/ethanol mixture was passed through a glass-fiber filter to immobilize large RNAs and the ethanol concentration of the filtrate was increased to 55%, and passed through a second glass-fiber filter to immobilize small RNAs. Both glass-fiber filters were washed to elute small and large RNAs separately.

2.7. Small RNA Northern Blot Hybridization

Detection of small interfering RNAs (siRNAs) by Northern blot was followed as described in the manual of mirVana™ miRNA Isolation Kit (Life Technologies Corp.) with few modifications. One μg small RNA enriched sample was run on a 15% denaturing polyacrylamide gel (urea/TBE) at 150 volts for 90-120 min or until the dye front reaches bottom of the gel. Semi-dry method was employed to transfer small RNAs to positively charged nylon membrane at 100 mA for 60 min and the RNA was immobilized on membrane by UV crosslinking. Full-length cDNA sequence of GFP (720 bp), PDS (1662 bp) and Awd (462 bp) genes were cloned into pGEM®-T Easy Vector (Promega) and negative-stranded DIG-labeled riboprobes were generated using DIG RNA labeling mix (Roche Applied Science) and T7 RNA polymerase. These probes were further hydrolyzed into 50-100 nt long RNA pieces by treating with sodium carbonate buffer as described (Dalmay et al., 2000) and used for hybridization. Prehybridization and hybridization were done at 41° C. using ULTRAhyb™ solution (Life Technologies Corp.) of 10 mL per 100 cm² of membrane. The rest of the Northern protocol was followed as described previously (Satyanarayana et al., 1999) except the high stringency wash at 41° C. Synthetic 5'-DIG-labeled oligonucleotide of 18 and 21 mer, which ran as 20 and 22 nucleotides respectively, were used as siRNA size markers in small RNA Northern blot hybridizations.

2.8. Reverse Transcription Quantitative PCR (RT-qPCR) for Plant Tissue

The large RNA isolated from mirVana™ miRNA Isolation Kit was used in SYBR Green-I based RT-qPCR to measure the level of down-regulation of PDS mRNAs due to gene silencing by CTV-based silencing vector in comparison to CTV-wt control plants. Citrus actin (ACT) gene expression was used as an internal control to normalize gene expressions among treatments for RT-qPCR reactions. The level of PDS mRNA from control plants infected with CTV-wt was arbitrarily set to a value of one (1) and the level of the PDS mRNA from plants infected with CTV-tPDS was estimated as a relative number to this reference value (Hajeri et al., 2011). Similar procedures were followed to measure the level of down-regulation of GFP mRNAs from *N. benthamiana* line 16c due to gene silencing by CTV-tGFP vector.

2.9. Insect Bioassay

Asian citrus psyllid, *D. citri* used in this study were collected from citrus groves, Polk Co., Fla. and maintained on Valencia sweet orange, *C. sinensis* (L.) (Osbeck), at 28±1° C., 60±2% RH and 16/8 h photoperiod. One year old *C. macrophylla* seedlings (approximately two feet tall & stem of a pencil thickness) were used for insect bioassay. In feeding experiments, each of the *C. macrophylla* seedling infected with either CTV-tAwd or CTV-wt control was exposed to 100 *D. citri* adults caged in insect rearing cages (30 in.×15.5 in.×15 in.) and kept in growth rooms in conditions as described above. One-month post exposure, all adults and nymphs were removed and egg masses were left. Two weeks later, newly emerged adults were counted, collected and examined for wing malformation and photographed using a Canon Power Shot S3IS digital camera, Leica M3Z stereomicroscope. Five replicative treatments for each experiment were used and compared statistically by the use of t test the number of adults with malformed wings to total adults.

2.10. Gene Expression Analysis in *D. citri*

Total RNA was isolated using TRIzol® Reagent (Life Technologies Corp.) from total of 10 *D. citri* for each treatment. Single-stranded RNA was purified from the total RNA by ssDNA/RNA Clean & Concentrator™ (Zymo Research) and expression levels of Awd was determined using SYBR Green-I based RT-qPCR in triplicate for each biological replicate. Alpha-tubulin (TubA) was used as a non-target gene control and we normalized gene expression of actin (Act) to compare the relative gene expression levels among treatments. The level of Awd transcripts in *D. citri* adults exposed to CTV-wt plants was arbitrarily set to the value one and the level of Awd transcripts in CTV-tAwd were presented as relative value to this reference value (Hajeri et al., 2011). Means and standard deviation of experiments in triplicate are presented.

3. Results 3.1. CTV-Induced Gene Silencing in *N. benthamiana* Line 16c

*N. benthamiana* is a non-natural host of CTV. To demonstrate the gene silencing capabilities of CTV, transgene green fluorescent protein (GFP) of *N. benthamiana* line 16c was silenced by CTV-VIGS vector carrying truncated GFP (tGFP; Supplementary data 1a). We engineered tGFP into CTV to express 400 nucleotides of GFP under CTV CP sgRNA controller element (CE) using unique PacI and StuI restriction sites (FIG. 30). *N. benthamiana* plants were inoculated with a binary plasmid vector carrying CTV-tGFP through agro-infiltration of fully expanded true leaves. Wild type CTV (CTV-wt) was used as a control. Progression of GFP silencing was monitored in the leaves, stems and flowers by fluorescence observation under long wave UV (FIG. 31a). Northern blot analysis of total RNA from the systemic leaves showed accumulation of the extra sgRNA in CTV-tGFP plants compared to CTV-wt plants. The tGFP sgRNA was the most abundantly accumulated sgRNA and the tGFP sequence was present as a component of all sub-genomic and genomic RNAs (FIG. 31b). The GFP silencing was further confirmed by reverse transcription quantitative PCR (RT-qPCR) showing 4-5-fold down-regulation of GFP mRNA (data not shown), the extent of GFP-mRNA down regulation does not represent a true value because the total RNA isolated for RT-qPCR represents a mixture from silenced and non-silenced regions. Further, Northern blots hybridization showed accumulation of GFP-specific ~21 nucleotide small interfering RNAs (siRNAs) from plants infected with CTV-tGFP compared to CTV-wt control plants (FIG. 31c).

3.2. CTV-Induced Gene Silencing in Citrus

To test the silencing induced by CTV in citrus, its natural host, citrus endogenous gene, phytoene desaturase (PDS) was targeted by CTV-VIGS vector carrying truncated PDS (tPDS; below). We engineered tPDS into CTV to express 392 nucleotides of PDS under CTV CP sgRNA CE using unique PacI and StuI restriction sites (FIG. 30). *N. benthamiana* plants were inoculated with a binary plasmid vector carrying CTV-tPDS through agro-infiltration of fully expanded true leaves and wild type CTV (CTV-wt) was used as a control. CTV virions were isolated from symptomatic systemic leaves of *N. benthamiana* four weeks post infiltration. *C. macrophylla* plants inoculated with CTV-tPDS virions showed a photo-bleaching phenotype in the newly emerging leaves, stems and thorns (FIG. 32a) compared to control CTV-wt plants. Northern blot analysis of RNA showed accumulation of the extra sgRNA in CTV-tPDS plants compared to CTV-wt plants (FIG. 32b). Further, RT-qPCR showed a 2.5-3-fold down-regulation of PDS mRNA in infected leaves (data not shown). Additionally PDS-specific siRNAs were detected from plants infected with CTV-tPDS compared to CTV-wt (FIG. 32c).

Graft-transmissibility of CTV-VIGS vector and photo-bleaching phenotype to other citrus cultivars was tested. Source plant, *C. macrophylla*, harboring CTV-tPDS vector, used for side and leaf graft inoculations to Duncan grapefruit (*C. paradisi*) and Sour orange (*C. aurantium*), which induced photo-bleaching phenotype in the newly emerged systemic leaves (FIG. 33).

3.3. CTV-Based Citrus Plant-Mediated RNAi in Phloem-Sap Sucking Insect *D. citri*

The results presented above suggested that CTV vector could be successfully used as an efficient silencing vector. We designed CTV-RNAi vector, CTV-tAwd, to express 459 nucleotides sequence of *D. citri* Awd gene (tAwd; below) in citrus similar to CTV-tPDS (FIG. 30). CTV-tAwd virions were isolated from symptomatic systemic leaves of *N. benthamiana* and inoculated to *C. macrophylla* plants similar to CTV-tPDS. Northern analysis of the total RNA isolated from newly emerged systemic leaves of *C. macrophylla* plants, which were inoculated with CTV-tAwd, showed the accumulation of an extra sgRNA for tAwd compared to CTV-wt (FIG. 34a). Awd-specific siRNAs were detected in CTV-tAwd plants compared to CTV-wt (FIG. 34b). One hundred adult *D. citri* (per plant) were allowed to feed on five individually caged *C. macrophylla* infected with CTV-tAwd. One-month post exposure, all *D. citri* adults and nymphs were removed and egg masses were left. Two weeks later, we calculated the total number of resulting *D. citri* adults in the new generation. Statistically significant differences (t test and evaluated at $P<0.05$) were observed in number of newly emerged adults between CTV-tAwd and CTV-wt plants (FIG. 34c). Among the new generation of *D. citri* adults that emerged from nymphs, some displayed wing-malformed phenotype. Nearly 15% of the nymphs fed on CTV-tAwd plants developed into severe wing-malformed adults (FIGS. 34d and f-ii) and another 30% of nymphs developed varying degrees of wing-malformation.

Alpha-tubulin (TubA) and actin (Act) were used as a non-target control gene and internal control gene, respectively to quantify Awd expression level between the treatments by t-test analysis. TubA expression did not change between treatments while Awd gene expression was downregulated approximately 1.5-2-fold in wing-malformed adults of *D. citri* compared to control *D. citri* (FIG. 34*e*). Acquisition of CTV-specific dsRNAs by *D. citri* was confirmed by conventional two-step RT-PCR using sense or antisense primer generated cDNAs from RNAs isolated from *D. citri* fed on CTV-tPDS and CTV-tAwd plants (unpublished data).

4. Discussion

During replication, CTV accumulates abundant amounts of genomic and sub-genomic (sg) replicative intermediates as double-stranded RNAs (Dodds and Bar-Joseph, 1983 and Hilf et al., 1995) and copious amounts of siRNAs (Scott and Dawson, unpublished), the latter possibly the consequence of antiviral silencing activity. The sgRNAs for ORFs closer to the 3'-ends accumulated in abundance compared to ORFs away from the 3'-end (Navas-Castillo et al., 1997). Additionally, the sgRNAs for p23, p20 and CP with dedicated sgRNA controller elements are produced in higher abundance compared to other sgRNAs (Hilf et al., 1995). It is thus possible to augment the abundance of silencing triggers, such as dsRNAs and siRNAs, by engineering sequence of interest at the 3' end and foster CTV as a gene silencing vector. We have demonstrated the gene silencing capabilities of CTV vectors by silencing transgene GFP in *N. benthamiana* line 16c and endogenous gene PDS in citrus. Thus, CTV-based VIGS vector could be a useful tool for reverse genetics to study the functions of citrus genes involved in basic cellular functions, metabolic pathways, developmental biology, and plant-microbe interactions.

The observations that the three RNA silencing suppressors do not prevent CTV-induced gene silencing, that CTV accumulates to high levels in phloem and phloem-associated cells, that CTV produces large amounts of dsRNAs, and that *D. citri* nymphs suck large amounts of fluid from the phloem of young shoots encouraged us to target psyllid genes using CTV-based RNAi vector.

Bt (*Bacillus thuringiensis*) toxin expressing transgenic plants have been effectively controlling chewing insects such as lepidopteran and coleopteran pests (Naranjo, 2011 and Shelton et al., 2002). However, for phloem sap-sucking insects, such as psyllids, aphids, whiteflies, planthoppers and plant bugs, pesticides are still the major method to control (Walker and Allen, 2010 and Gatehouse and Price, 2011). Therefore, in order to control phloem sap-sucking insects, novel methodologies such as RNAi-based technology must be considered in order to rein in economic and environmental damage (Zhang et al., 2013).

The two major challenges in deploying RNAi-based technology for pest control are effective target gene selection and reliable dsRNA delivery. We targeted *D. citri* endogenous Awd gene for silencing; because, inhibition of the Awd gene would induce altered wing development, a visible phenotype and down regulation of wing development of *D. citri* would impair its ability to fly and potentially limit the successful vectoring of the bacterial pathogen between citrus trees in the grove. Once the target gene is identified, the reliable and convenient dsRNA delivery system is prerequisite for pest control at field level. Delivery of dsRNA could be achieved by micro-injection, micro-application (topical application), soaking or by feeding as a dietary component (El-Shesheny et al., 2013 and Zhang et al., 2013). However, these methods can only be used in laboratory experiments. Spraying dsRNA targeting specific insect pest could be a viable approach at the field level (Gan et al., 2010), if dsRNA can be cheaply mass produced. Expression of dsRNAs in transgenic plants has been shown to induce RNAi effects on target insects (Huang et al., 2006, Baum et al., 2007, Mao et al., 2007 and Gottula and Fuchs, 2009). However, transgenic approach in citrus is slow and difficult. By virtue of its time, labor and cost efficiency, transient expression system of CTV-based plant-mediated RNAi provides major advantage over stable transformation in citrus since the CTV vector has been shown to be stable for several years in trees. This remarkable stability of CTV vector could be used in silencing insect genes or other pest genes directly in the field as an integrated pest management practice. Graft-transmissibility of CTV-tPDS vector and its silencing triggers to other citrus cultivars suggested that the silencing trait against insect pests induced by CTV-RNAi vector could also be transferable to other commercial cultivars of citrus through vegetative grafting which is not possible with transgenic lines with such traits.

Even in case of preference of transgenic approach over CTV-based RNAi, the CTV vector would act as a tool in fast-track screening of candidate genes/sequences related to insect's survivability, flight, or reproduction and ultimately affect the vectoring potential of insect vector in developing transgenic citrus. Thus CTV-based silencing vector would hasten the process of selecting right candidate sequences for stable transformation. On the other hand, CTV-based silencing vector could be used as an interim solution in mitigating the HLB disease manifestation at present in the field. The species specificity is the critical issue that needs to be addressed before using RNAi-based pest control measures in the field. But RNAi technology has the potential to address this problem by producing sequence specific and species specific RNAi pesticide (Whyard et al., 2009).

5. Conclusions

Three RNA silencing suppressors of CTV do not prevent CTV from inducing gene silencing in *Citrus* and *N. benthamiana* transgenic line 16c. CTV-based plant-mediated RNAi induces gene silencing in phloem-sap sucking insect *D. citri*, which vectors bacterial disease HLB. Thus CTV-based RNAi vector could be a valuable tool for fast-track screening candidate sequences in developing transgenic citrus against citrus pest and diseases. Because of the slow and difficult transgenic methodology in citrus, CTV-RNAi vector could be an interim solution in mitigating the spread of HLB disease in the field.

Genes Related to Example 9

```
(a) tGFP
GCTAGCAAAGGAGAAGAACTTTTCACTGGAGTTGTCCCAATTCTTGTTGA

ATTAGATGGTGATGTTAATGGGCACAAATTTTCTGTCAGTGGAGAGGGTG

AAGGTGATGCTACATACGGAAAGCTTACCCTTAAATTTATTTGCACTACT

GGAAAACTACCTGTTCCATGGCCAACACTTGTCACTACTTTCTCTTATGG

TGTTCAATGCTTTTCCCGTTATCCGGATCATATGAAACGGCATGACTTTT

TCAAGAGTGCCATGCCCGAAGGTTATGTACAGGAAAGAACTATATTTTTC

AAAGATGACGGGAACTACAAGACGCGTGCTGAAGTCAAGTTTGAAGGTGA

TACCCTTGTTAATCGTATCGAGTTAAAAGGTATTGATTTTAAAGAAGATG

GAAACATTCTCGGACACAAACTCGAGTACAACTATAACTC (b) tPDS
AGCCTTTGCTTCAGCGTTTCTGAAAGTGCTTTCAACTTGCGATATGGTTT

CCGAGATAGTGAACCGATGGGTCAGAGCCTGAAAATTCGAGTTAAAACGA
```

-continued

```
GGACAAGGAAGGGTTTCTGTCCTTCGAAGGCGGTTTGTGTGGACTACCCA

AGACCAGATATTGATAATACATCTAATTTCTTGGAAGCTGCTTACTTATC

TTCGTCATTTCGTACTTCTCCTCGTCCTTCTAAGCCGTTGAAAGTTGTAA

TTGCTGGTGCAGGTTTGGCTGGTTTATCAACTGCAAAATATTTGGCAGAT

GCAGGCCACAAGCCTTTGTTACTGGAAGCAAGAGATGTTCTAGGTGGAAA

GATAGCTGCCTGGAAAGATGGGACGGGAACTGGTAGAGAC (c) tAwd
GCCGAACCCAAGGAAAGAACTTTTCTCATGATCAAGCCCGATGGCGTTCA

AAGAGGACTTGTGGGAAACATCATCAAACGCTTTGAAGACAAAGGCTTCA

AATTGGTGGCCATGAAATTCGTTTGGCCATCCGAAGAACTTCTGAAGCAA

CACTACTCAGATTTGGCCACCAAACCTTTCTTCCCTGGTCTTGTCAAATA

CATGTCATCTGGACCTGTTGTTCCTATGGTGTGGGAAGGATTGAACATTG

TCAAAACTGGACGTGTGATGCTTGGAGCCACCAACCCTGCTGACTCTGCC

CCAGGAACTGTCAGAGGAGACCTCTGCATCCAAGTTGGAAGAAACATCAT

GCATGGATCAGACTCTGTTGAATCTGCAAAGAAAGAAATTGCCTTATGGT

TCACTGAGAAAGAAGTCATTGGATGGACAAATGCCAGTGAATCCTGGATC

TATGAATAA
```

REFERENCES

Ambrós, S., El-Mohtar, C., Ruiz-Ruiz, S., Pe~na, L., Guerri, J., Dawson, W. O., Moreno, P., 2011. Agroinoculation of Citrus tristeza virus causes systemic infection and symptoms in the presumed nonhost *Nicotiana benthamiana*. Mol. Plant-MicrobeInteract. 24, 1119-1131.

Bar-Joseph, M., Garnsey, S. M., Gonsalves, D., 1979. The closteroviruses. A distinctgroup of elongated plant viruses. Adv. Virus Res. 25, 93-168.

Baum, J. A., Bogaert, T., Clinton, W., Heck, G. R., Feldmann, P., Ilagan, O., Johnson, S., Plaetinck, G., Munyikwa, T., Pleau, M., Vaughn, T., Roberts, J., 2007. Con-trol of coleopteran insect pests through RNA interference. Nat. Biotechnol. 25, 1322-1326.

Chomczynski, P., Sacchi, N., 1987. Single-step method of RNA isolation by acidguanidinium thiocyanate-phenol-chloroform extraction. Anal. Biochem. 162, 156-159.

Dalmay, T., Hamilton, A. J., Mueller, E., Baulcombe, D. C., 2000. Potato virus X ampli-cons in *Arabidopsis* mediate genetic and epigenetic gene silencing. Plant Cell 12, 369-380.

Dawson, W. O., Folimanova, S., 2013. Virus-based transient expression vectors forwoody crops: a new frontier for vector design and use. Ann. Rev. Phytopathol. 51, 321-337.

Dodds, J. A., Bar-Joseph, M., 1983. Double-stranded RNA from plants infected with closteroviruses. Phytopathology 73, 419-423.

Dolja, V. V., Koonin, E. V., 2013. The closterovirus-derived gene expression and RNA interference vectors as tools for research and plant biotechnology. Front. Micro-biol. 4, 83.

El-Mohtar, C., Dawson, W. O., 2014. Exploring the limits of vector construction based on Citrus tristeza virus. Virology 448, 274-283.

El-Shesheny, I., Hajeri, S., El-Hawary, I., Gowda, S., Killiny, N., 2013. Silencing abnor-mal wing disc gene of the Asian Citrus Psyllid, *Diaphorina citri* disrupts adultwing development and increases nymph mortality. PLoS ONE 8 (5), e65392.

Fire, A. Z., 2007. Gene silencing by double-stranded RNA (Nobel lecture). Cell DeathDiffer. 14, 1998-2012.

Folimonov, A. S., Folimonova, S. Y., Bar-Joseph, M., Dawson, W. O., 2007. A stable RNAvirus-based vector for citrus trees. Virology 368, 205-216.

Gan, D., Zhang, J., Jiang, H., Jiang, T., Zhu, S., Cheng, B., 2010. Bacterially expressed dsRNA protects maize against SCMV infection. Plant Cell Rep. 29, 1261-1268.

Gatehouse, J. A., Price, D. R. G., 2011. Protection of crops against insect pests using RNA interference. Insect Biotechnol. 2, 145-168.

Geley, S., Müller, C., 2004. RNAi: ancient mechanism with a promising future. Exp. Gerontol. 39, 985-998.

Gleba, Y., Klimyuk, V., Marillonnet, S., 2007. Viral vectors for the expression of pro-teins in plants. Curr. Opin. Biotechnol. 18, 134-141.

Gordon, K. H. J., Waterhouse, P. M., 2007. RNAi for insect-proof plants. Nat. Biotechnol. 25, 1231-1232.

Gottula, J., Fuchs, M., 2009. Toward a quarter century of pathogen-derived resis-tance and practical approaches to plant virus disease control. Adv. Virus Res. 75, 161-183.

Gowda, S., Satyanarayana, T., Robertson, C. J., Garnsey, S. M., Dawson, W. O., 2005. Infection of citrus plants with virions generated in *Nicotiana benthamiana* plantsagroin-filtrated with binary vector based Citrus tristeza virus. In: Hilf, M. E., Duran-Vila, N., Rocha-Pena, M. A. (Eds.), Proceedings of the 16th Conference of the International Organization of Citrus Virologists. IOCV, Riverside, Calif., pp. 23-33.

Hajeri, S., Ramadugu, C., Manjunath, K., Ng, J., Lee, R., Vidalakis, G., 2011. In vivo generated Citrus exocortis viroid progeny variants display a range of phenotypes with altered levels of replication, systemic accumulation and pathogenicity. Virology 417, 400-409.

Halbert, S. E., Manjunath, K. L., 2004. Asian citrus psyllid (Sternorrhyncha: Psyllidae) and greening disease of citrus: a literature review and assessment of risk in Florida. Fla. Entomol. 87, 330-353.

Hilf, M. E., Karasev, A. V., Pappu, H. R., Gumpf, D. J., Niblett, C. L., Garnsey, S. M., 1995. Characterization of citrus tristeza virus subgenomic RNAs in infected tissue. Virology 208, 576-582.

Hodges, A. W., Spreen, T. H., 2012. EDIS document FE903, a publication of the Food and Resource Economics Department, Florida Cooperative Extension Service, Institute of Food and Agricultural Sciences. University of Florida, Gainesville, Fla. http://edis.ifas.ufl.edu/fe903

Huang, G., Allen, R., Davis, E. L., Baum, T. J., Hussey, R. S., 2006. Engineering broadroot-knot resistance in transgenic plants by RNAi silencing of a conserved and essential root-knot nematode parasitism gene. Proc. Natl. Acad. Sci. U.S.A. 103, 14302-14306.

Karasev, A. V., Boyko, V. P., Gowda, S., Nikolaeva, O. V., Hilf, M. E., Koonin, E. V., Niblett, C. L., Cline, K., Gumpf, D. J., Lee, R. F., Garnsey, S. M., Lewandowski, D. J., Dawson, W. O., 1995. Complete sequence of the citrus tristeza virus RNA genome. Virology 208, 511-520.

Khan, A. M., Ashfaq, M., Kiss, Z., Khan, A. A., Mansoor, S., Falk, B. W., 2013. Use of recombinant tobacco mosaic virus to achieve RNA interference in plants against the citrus mealybug, *Planococcus citri* (Hemiptera: Pseudococcidae). PLoS ONE 8(9), e73657.

Kurth, E. G., Peremyslov, V. V., Prokhnevsky, A. I., Kasschau, K. D., Miller, M., Carrington, J. C., Dolja, V. V., 2012. Virus-derived gene expression and RNA interference vector for grapevine. J. Virol. 86, 6002-6009.

Lu, R., Folimonov, A., Shintaku, M., Li, W. X., Falk, B. W., Dawson, W. O., Ding, S. W., 2004. Three distinct suppressors of RNA silencing encoded by a 20-kb viral RNA genome. Proc. Natl. Acad. Sci. U.S.A. 101, 15742-15747.

Lu, R., Martin-Hernandez, A. M., Peart, J. R., Malcuit, I., Baulcombe, D. C., 2003. Virus-induced gene silencing in plants. Methods 30, 296-303.

Mao, Y. B., Cai, W. J., Wang, J. W., Hong, G. J., Tao, X. Y., Wang, L. J., Huang, Y. P., Chen, X. Y., 2007. Silencing a cotton bollworm P450 monooxygenase gene by plant-mediated RNAi impairs larval tolerance of gossypol. Nat. Biotechnol. 25, 1307-1313.

Naranjo, S. E., 2011. Impacts of Bt transgenic cotton on integrated pest management. J. Agric. Food Chem. 59, 5842-5851. National Research Council, 2010. Strategic Planning for the Florida Citrus Industry: Addressing Citrus Greening Disease. The National Academic Press, Washington, D.C., pp. 84-86 (Chapter 3).

Navas-Castillo, J., Albiach-Martí, M. R., Gowda, S., Hilf, M. E., Garnsey, S. M., Dawson, W. O., 1997. Kinetics of accumulation of Citrus tristeza virus RNAs. Virology 228, 92-97.

Porta, C., Lomonossoff, G. P., 2002. Viruses as vectors for the expression of foreign sequences in plants. Biotechnol. Genet. Eng. Rev. 19, 245-291.

Price, D. R., Gatehouse, J. A., 2008. RNAi-mediated crop protection against insects. Trends Biotechnol. 26, 393-400.

Ratcliff, F., Harrison, B. D., Baulcombe, D. C., 1997. A similarity between viral defense and gene silencing in plants. Science 276, 1558-1560.

Robertson, C. J., Garnsey, S. M., Satyanarayana, T., Folimonova, S., Dawson, W. O., 2005. Efficient infection of citrus plants with different cloned constructs of Cit-rus tristeza virus amplified in *Nicotiana benthamiana* protoplasts. In: Hilf, M. E., Duran-Vila, N., Rocha-Pena, M. A. (Eds.), Proceedings of the 16th Conference of the International Organization of *Citrus* Virologists. IOCV, Riverside, Calif., pp. 187-195.

Satyanarayana, T., Gowda, S., Boyko, V. P., Albiach-Martí, M. R., Mawassi, M., Navas-Castillo, J., Karasev, A. V., Dolja, V., Hilf, M. E., Lewandowski, D. J., Moreno, P., Bar-Joseph, M., Garnsey, S. M., Dawson, W. O., 1999. An engineered closterovirus RNA replicon and analysis of heterologous terminal sequences for replication. Proc. Natl. Acad. Sci. U.S.A. 96, 7433-7438.

Satyanayanana, T., Bar-Joseph, M., Mawassi, M., Albiach-Martí, M. R., Ayllón, M. A., Gowda, S., Hilf, M. E., Moreno, P., Garnsey, S. M., Dawson, W. O., 2001. Amplifica-tion of Citrus tristeza virus from a cDNA clone & infection of citrus trees. Virology 280, 87-96.

Shelton, A. M., Zhao, J. Z., Roush, R. T., 2002. Economic, ecological, food safety, and social consequences of the deployment of Bt transgenic plants. Annu. Rev. Ento-mol. 47, 845-881. Tenllado, F., Díaz-Ruíz, J. R., 2001. Double-stranded RNA-mediated interference with plant virus infection. J. Virol. 75, 12288-12297.

Walker, W. B., Allen, M. L., 2010. Expression and RNA interference of salivary poly-galacturonase genes in the tarnished plant bug, *Lygus lineolaris*. J. Insect Sci. 10, 1-13.

Waterhouse, P. M., Wang, M. B., Lough, T., 2001. Gene silencing as an adaptive defense against viruses. Nature 411, 834-842. Weber, F., Wagner, V., Rasmussen, S. B., Hartmann, R., Paludan, S. R., 2006. Double-stranded RNA is produced by positive-strand RNA viruses and DNA viruses but not in detectable amounts by negative-strand RNA viruses. J. Virol. 80, 5059-5064.

Whyard, S., Singh, A. D., Wong, S., 2009. Ingested double stranded RNAs can act as species-specific insecticides. Insect Biochem. Mol. Biol. 39, 824-832.

Wuriyanghan, H., Falk, B. W., 2013. RNA interference towards the potato psyllid, Bactericera cockerelli, is induced in plants infected with recombinant Tobaccomosaic virus (TMV). PLoS ONE 8 (6), e66050.

Zhang, H., Li, H-C., Miao, X-X., 2013. Feasibility, limitation and possible solutions of RNAi-based technology for insect pest control. Insect Sci. 20, 15-30.

While various disclosed embodiments have been described above, it should be understood that they have been presented by way of example only, and not limitation. Numerous changes to the subject matter disclosed herein can be made in accordance with this Disclosure without departing from the spirit or scope of this Disclosure. In addition, while a particular feature may have been disclosed with respect to only one of several implementations, such feature may be combined with one or more other features of the other implementations as may be desired and advantageous for any given or particular application.

Thus, the breadth and scope of the subject matter provided in this Disclosure should not be limited by any of the above explicitly described embodiments. Rather, the scope of this Disclosure should be defined in accordance with the following claims and their equivalents.

The terminology used herein is for the purpose of describing particular embodiments only and is not intended to be limiting. As used herein, the singular forms "a," "an," and "the" are intended to include the plural forms as well, unless the context clearly indicates otherwise. Furthermore, to the extent that the terms "including," "includes," "having," "has," "with," or variants thereof are used in either the detailed description and/or the claims, such terms are intended to be inclusive in a manner similar to the term "comprising."

Unless otherwise defined, all terms (including technical and scientific terms) used herein have the same meaning as commonly understood by one of ordinary skill in the art to which embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

The teachings of any patents, patent applications, technical or scientific articles or other references are incorporated herein in their entirety to the extent not inconsistent with the teachings herein.

What is claimed is:

1. A Citrus Tristesa Virus (CTV) viral vector engineered to comprise a gene cassette comprising a heterologous nucleic acid, the CTV viral vector engineered such that the gene cassette is inserted 3' behind the p23 gene, wherein the CTV viral vector infects trees.

2. The CTV viral vector of claim 1, wherein said heterologous nucleic acid encodes an RNA interfering molecule.

3. The CTV viral vector of claim 2, wherein said RNA interfering molecule targets a nucleic acid of a plant pathogen, biological vector, or pest.

4. The CTV viral vector of claim 2, wherein said RNA interfering molecule targets a psyllid or endogenous plant mRNA.

5. The CTV viral vector of claim 1, wherein said heterologous nucleic acid encodes a protein.

6. The CTV viral vector of claim 1, wherein said gene cassette lacks a subgenomic controller element for control of said heterologous nucleic acid.

7. The CTV viral vector of claim 3, wherein the pest comprises an arthropod or nematode.

8. The CTV viral vector of claim 4 wherein the RNA interfering molecule targets D. citri Awd.

* * * * *